United States Patent [19]

Anderson et al.

[11] Patent Number: 6,118,047
[45] Date of Patent: Sep. 12, 2000

[54] ANTHRANILATE SYNTHASE GENE AND METHOD OF USE THEREOF FOR CONFERRING TRYPTOPHAN OVERPRODUCTION

[75] Inventors: Paul C. Anderson, West Des Moines, Iowa; Paul S. Chomet, Mystic, Conn.; Matthew C. Griffor, North Stonington, Conn.; Alan L. Kriz, Gales Ferry, Conn.

[73] Assignee: DeKalb Genetic Corporation, DeKalb, Ill.

[21] Appl. No.: 08/604,789

[22] Filed: Jan. 19, 1996

Related U.S. Application Data

[63] Continuation-in-part of application No. 08/113,561, Aug. 25, 1993.

[51] Int. Cl.⁷ ............................. C12N 5/04; C12N 15/82; C12N 15/29; A01H 5/00
[52] U.S. Cl. ............... 800/278; 800/298; 800/320.1; 435/419; 435/183; 435/252.3; 435/320.1; 435/108; 536/23.2
[58] Field of Search .................... 435/419, 183, 435/69.1, 252.3, 320.1; 536/23.2; 800/278

[56] References Cited

U.S. PATENT DOCUMENTS

| | | | |
|---|---|---|---|
| 4,370,160 | 1/1983 | Ziemelis | 71/117 |
| 4,399,216 | 8/1983 | Axel et al. | 435/6 |
| 4,535,060 | 8/1985 | Comai | 435/172.3 |
| 4,559,301 | 12/1985 | Turner | 435/76 |
| 4,559,302 | 12/1985 | Ingolia | 435/172.3 |
| 4,581,847 | 4/1986 | Hibberd et al. | 47/58 |
| 4,634,665 | 1/1987 | Axel et al. | 435/68 |
| 4,642,411 | 2/1987 | Hibberd et al. | 800/1 |
| 4,665,030 | 5/1987 | Close | 435/240 |
| 4,666,844 | 5/1987 | Cheng | 435/240 |
| 4,683,202 | 7/1987 | Mullis | 435/91 |
| 4,727,028 | 2/1988 | Santerre et al. | 435/240.2 |
| 4,743,548 | 5/1988 | Crossway et al. | 435/172.3 |
| 4,761,373 | 8/1988 | Anderson et al. | 435/172.3 |
| 4,806,483 | 2/1989 | Wang | 435/240.49 |
| 4,885,357 | 12/1989 | Larkins et al. | 530/373 |
| 4,886,878 | 12/1989 | Larkins et al. | 536/26 |
| 4,940,835 | 7/1990 | Shah et al. | 800/205 |
| 4,971,908 | 11/1990 | Kishore et al. | 435/172.1 |
| 5,001,060 | 3/1991 | Peacock et al. | 435/172.3 |
| 5,004,863 | 4/1991 | Umbeck | 800/205 |
| 5,013,658 | 5/1991 | Dooner et al. | 435/172.3 |
| 5,015,580 | 5/1991 | Christou et al. | 435/172.3 |
| 5,034,322 | 7/1991 | Rogers et al. | 435/172.3 |
| 5,049,500 | 9/1991 | Arnizen et al. | 435/172.3 |
| 5,094,945 | 3/1992 | Comai | 435/172.3 |
| 5,110,732 | 5/1992 | Benfey et al. | 435/172.3 |
| 5,134,074 | 7/1992 | Gordon et al. | 435/240.4 |
| 5,145,777 | 9/1992 | Goodman et al. | 435/172.3 |
| 5,164,310 | 11/1992 | Smith et al. | 435/172.3 |
| 5,177,010 | 1/1993 | Goldman et al. | 435/172.3 |
| 5,187,073 | 2/1993 | Goldman et al. | 435/172.3 |
| 5,187,267 | 2/1993 | Comai et al. | 536/23.1 |
| 5,188,642 | 2/1993 | Shah et al. | 47/58 |
| 5,188,958 | 2/1993 | Moloney et al. | 435/240.4 |
| 5,215,912 | 6/1993 | Hoffman | 435/240.4 |
| 5,250,515 | 10/1993 | Fuchs et al. | 514/12 |
| 5,254,799 | 10/1993 | DeGrave et al. | 800/205 |
| 5,258,300 | 11/1993 | Glassman et al. | 435/240.4 |
| 5,268,463 | 12/1993 | Jefferson | 536/23.7 |
| 5,272,072 | 12/1993 | Kaneko et al. | 435/172.3 |
| 5,273,894 | 12/1993 | Strauch et al. | 435/129 |
| 5,276,268 | 1/1994 | Strauch et al. | 800/205 |
| 5,278,325 | 1/1994 | Strop et al. | 554/12 |
| 5,290,924 | 3/1994 | Last et al. | 536/24.1 |

(List continued on next page.)

FOREIGN PATENT DOCUMENTS

| | | |
|---|---|---|
| B-80893/87 | 12/1988 | Australia . |
| 2032443 | 12/1990 | Canada . |
| 0 126 537 A2 | 4/1983 | European Pat. Off. . |
| 0 131 623 B1 | 1/1984 | European Pat. Off. . |
| 0 141 373 A3 | 5/1985 | European Pat. Off. . |
| 0 154 204 A2 | 9/1985 | European Pat. Off. . |
| 0 160 390 A2 | 11/1985 | European Pat. Off. . |
| 0174791 | 3/1986 | European Pat. Off. . |
| 0 189 707 A2 | 8/1986 | European Pat. Off. . |
| 0 193 259 A1 | 9/1986 | European Pat. Off. . |
| 0 204 549 A2 | 10/1986 | European Pat. Off. . |
| 0 202 668 A2 | 11/1986 | European Pat. Off. . |
| 0 242 236 A1 | 10/1987 | European Pat. Off. . |
| 0 242 246 A1 | 11/1987 | European Pat. Off. . |
| 0 299 552 A1 | 1/1988 | European Pat. Off. . |
| 0 257 472 A2 | 3/1988 | European Pat. Off. . |
| 0 262 971 A2 | 5/1988 | European Pat. Off. . |
| 0 270 356 A2 | 6/1988 | European Pat. Off. . |
| 0 271 408 | 6/1988 | European Pat. Off. . |
| 0 275 069 A2 | 7/1988 | European Pat. Off. . |
| 0 280 400 A2 | 8/1988 | European Pat. Off. . |
| 0 282 164 A2 | 9/1988 | European Pat. Off. . |
| 0 289 479 A2 | 11/1988 | European Pat. Off. . |

(List continued on next page.)

OTHER PUBLICATIONS

Specification of U.S. Patent Application, Serial No. 07/205,155, entitled "Stable Transformation of Plant Cells," pp. 1–29 (Filed Jun. 10, 1988).

Niyogi et al. The Plant Cell. 4: 721–33, 1992.

(List continued on next page.)

*Primary Examiner*—Robert A. Wax
*Assistant Examiner*—Tekchand Saidha
*Attorney, Agent, or Firm*—Schwegman, Lundberg, Woessner and Kluth, P.A.

[57] ABSTRACT

The present invention provides a method for conferring tolerance to an amino acid analog of tryptophan to a plant and/or altering the tryptophan content of a plant by introducing and expressing an isolated DNA segment encoding an anthranilate synthase in the cells of the plant. Transgenic plants transformed with an isolated DNA segment encoding an anthranilate synthase, as well as seeds and progeny derived from these plants, are also provided. The present invention also provides a cDNA sequence of an alpha and a beta subunit of a maize anthranilate synthase.

18 Claims, 7 Drawing Sheets

U.S. PATENT DOCUMENTS

| | | | |
|---|---|---|---|
| 5,302,523 | 4/1994 | Coffee et al. | 435/172.1 |
| 5,350,689 | 9/1994 | Shillito et al. | 435/240.47 |
| 5,352,605 | 10/1994 | Fraley et al. | 435/240.4 |
| 5,371,003 | 12/1994 | Murry et al. | 435/172.3 |
| 5,380,831 | 1/1995 | Adang et al. | 536/23.71 |
| 5,384,253 | 1/1995 | Krzyzek et al. | 435/172.3 |
| 5,405,765 | 4/1995 | Vasil et al. | 435/172.3 |
| 5,436,389 | 7/1995 | Pfund | 800/200 |
| 5,436,393 | 7/1995 | Rocha-Sosa et al. | 800/205 |
| 5,472,869 | 12/1995 | Krzyzek et al. | 435/240.4 |
| 5,484,956 | 1/1996 | Lundquist et al. | 800/205 |
| 5,489,520 | 2/1996 | Adams et al. | 435/172.3 |
| 5,491,288 | 2/1996 | Chaubet et al. | 800/205 |
| 5,500,365 | 3/1996 | Fischhoff et al. | 435/240.4 |
| 5,508,468 | 4/1996 | Lundquist et al. | 800/205 |
| 5,545,545 | 8/1996 | Gengenbach et al. | 435/172.3 |
| 5,550,318 | 8/1996 | Adams et al. | 800/205 |
| 5,554,798 | 9/1996 | Lundquist et al. | 800/205 |
| 5,559,223 | 9/1996 | Falco et al. | 536/23.1 |
| 5,561,236 | 10/1996 | Leemans et al. | 800/205 |
| 5,563,324 | 10/1996 | Tarczynski et al. | 800/205 |
| 5,565,347 | 10/1996 | Fillatti et al. | 435/172.3 |
| 5,567,600 | 10/1996 | Adang et al. | 536/23.71 |
| 5,567,862 | 10/1996 | Adang et al. | 800/205 |
| 5,576,203 | 11/1996 | Hoffman | 435/172.3 |
| 5,578,702 | 11/1996 | Adang et al. | 530/350 |
| 5,589,615 | 12/1996 | De Clercq et al. | 800/205 |
| 5,589,616 | 12/1996 | Hoffman et al. | 800/205 |
| 5,591,616 | 1/1997 | Hiei et al. | 435/172.3 |
| 5,595,733 | 1/1997 | Carswell et al. | 424/93.21 |
| 5,596,131 | 1/1997 | Horn et al. | 800/205 |
| 5,623,067 | 4/1997 | Vanderkerckhove et al. | 536/24.1 |
| 5,625,136 | 4/1997 | Koziel et al. | 800/205 |
| 5,641,664 | 6/1997 | D'Halluin et al. | 435/172.3 |
| 5,641,876 | 6/1997 | McElroy et al. | 536/24.1 |
| 5,743,477 | 4/1998 | Walsh et al. | 424/94.6 |
| 5,773,691 | 6/1998 | Falco et al. | 800/205 |

FOREIGN PATENT DOCUMENTS

| | | |
|---|---|---|
| 0 290 395 A2 | 11/1988 | European Pat. Off. . |
| 0 292 435 A1 | 11/1988 | European Pat. Off. . |
| 0 301 749 A2 | 2/1989 | European Pat. Off. . |
| 0 353 908 A2 | 7/1989 | European Pat. Off. . |
| 0 331 855 A2 | 9/1989 | European Pat. Off. . |
| 0 334 539 A2 | 9/1989 | European Pat. Off. . |
| 0 335 528 A2 | 10/1989 | European Pat. Off. . |
| 0 348 348 A2 | 12/1989 | European Pat. Off. . |
| 0 385 962 A1 | 2/1990 | European Pat. Off. . |
| 0 359 617 A2 | 3/1990 | European Pat. Off. . |
| 0 360 750 A2 | 3/1990 | European Pat. Off. . |
| 0 408 403 A1 | 5/1990 | European Pat. Off. . |
| 0 420 358 A1 | 4/1991 | European Pat. Off. . |
| 0 424 047 A1 | 4/1991 | European Pat. Off. . |
| 0 442 174 A1 | 4/1991 | European Pat. Off. . |
| 0 459 643 A2 | 5/1991 | European Pat. Off. . |
| 0 442 175 A1 | 8/1991 | European Pat. Off. . |
| 0 452 269 A2 | 11/1991 | European Pat. Off. . |
| 0 469 273 A1 | 2/1992 | European Pat. Off. . |
| 0 485 970 A3 | 5/1992 | European Pat. Off. . |
| 0 589 110 A1 | 3/1994 | European Pat. Off. . |
| 0 620 281 A2 | 10/1994 | European Pat. Off. . |
| 2 661 421 | 11/1991 | France . |
| 37 38 874 A1 | 11/1988 | Germany . |
| 40 13 099 A1 | 10/1991 | Germany . |
| 61-134343 | 5/1984 | Japan . |
| 8801444 | 1/1990 | Netherlands . |
| 2 159 173 | 11/1985 | United Kingdom . |
| WO 85/01856 | 5/1985 | WIPO . |
| WO 85/02972 | 7/1985 | WIPO . |
| WO 87/04181 | 7/1987 | WIPO . |
| WO 87/05629 | 9/1987 | WIPO . |
| WO 89/04371 | 5/1989 | WIPO . |
| 89/10396 | 11/1989 | WIPO . |
| WO 89/11789 | 12/1989 | WIPO . |
| WO 89/12102 | 12/1989 | WIPO . |
| WO 90/01869 | 3/1990 | WIPO . |
| WO 90/02801 | 3/1990 | WIPO . |
| WO 90/10691 | 8/1990 | WIPO . |
| WO 91/02071 | 2/1991 | WIPO . |
| 91/04270 | 4/1991 | WIPO . |
| WO 91/04323 | 4/1991 | WIPO . |
| WO 91/00183 | 5/1991 | WIPO . |
| WO 91/10725 | 7/1991 | WIPO . |
| WO 91/16432 | 10/1991 | WIPO . |
| WO 92/06205 | 4/1992 | WIPO . |
| WO 92/09696 | 6/1992 | WIPO . |
| WO 92/12250 | 7/1992 | WIPO . |
| 92/14822 | 9/1992 | WIPO . |
| 92/17580 | 10/1992 | WIPO . |
| WO 92/19731 | 11/1992 | WIPO . |
| 93/06220 | 4/1993 | WIPO . |
| WO 93/07278 | 4/1993 | WIPO . |
| 93/09237 | 5/1993 | WIPO . |
| WO 93/08682 | 5/1993 | WIPO . |
| WO 93/14210 | 7/1993 | WIPO . |
| WO 93/19190 | 9/1993 | WIPO . |
| WO 93/21335 | 10/1993 | WIPO . |
| 94/08031 | 4/1994 | WIPO . |
| 94/10315 | 5/1994 | WIPO . |
| 94/14970 | 7/1994 | WIPO . |
| 94/20628 | 9/1994 | WIPO . |
| 95/06128 | 3/1995 | WIPO . |
| 95/13389 | 5/1995 | WIPO . |
| 95/30005 | 11/1995 | WIPO . |
| 96/00789 | 1/1996 | WIPO . |

OTHER PUBLICATIONS

Bernasconi et al. Plant Physiol. Sep. 1994. 106(1): 353–358.

Armstrong, C.L., et al., "Genetic and Cytogenetic Variation in Plants Regenerated from Organogenic and Friable, Embryogenic Tissue Cultures in Maize", *Crop Science,* 28, 363–369 (1988).

Beauregard, M., et al., "Design, Expression, and Initial Characterization of MB1, a De Novo Protein Enriched in Essential Amino Acids", *Bio/Technology,* 13, 974–981 (Sep. 1995).

Casas, A.M., et al., "Transgenic Sorghum Plants via Microprojectile Bombardment", *Proc. Natl. Acad. Sci. USA,* 90, 11212–11216 (Dec. 1993).

Dure III, L., et al., "Common Amino Acid Sequence Domains Among the LEA Proteins of Higher Plants", *Plant Molecular Biology,* 12, 475–486 (1989).

Falco, S.C., et al., "Transgenic Canola and Soybean Seeds with Increased Lysine", *Bio/Technology,* 13, 577–582 (Jun. 1995).

Hong, B., et al., "Cloning and Characterization of cDNA Encoding a mRNA Rapidly–Induced by ABA in Barley Aleurone Layers", *Plant Molecular Biology,* 11, 495–506 (1988).

Lemaux, P.G., et al., "Selection of Stable Transformants from Maize Suspension Cultures Using the Herbicide Bialaphos", *J. Cell. Biochem.,* 14e, Abstract R230, 304 (Mar. 31, 1990).

Mundy, J., et al., "Abscisic Acid and Water–Stress Induce the Expression of a Novel Rice Gene", *The EMBO Journal,* 7, 2279–2286 (1988).

Piatkowski, D., et al., "Characterization of Five Abscisic Acid–Responsive cDNA Clones Isolated from the Desiccation–Tolerant Plant *Craterostigma plantagineum* and Their Relationship to Other Water–Stress Genes", *Plant Physiology*, 94, 1682–1688 (1990).

Somers, D.A., et al., "Fertile, Transgenic Oat Plants", *Bio/Technology*, 10, 1589–1594 (Dec. 1992).

Yamaguchi–Shinozaki, K., et al., "Molecular Cloning and Characterization of 9 cDNAs for Genes that are Responsive to Desiccation in *Arabidopsis thaliana:* Sequence Analysis of One cDNA Clone that Encodes a Putative Transmembrane Channel Protein", *Plant Cell Physiol.*, 33, 217–224 (1992).

Caliguri, M. G., et al., "Identification of Amino Acid Residues Involved in Feedback Regulation of the Anthranilate Synthase Complex from *Salmonella typhimurium,"* *J. Biol. Chem.*, 266, 8328–8335 (1991).

Niyogi, K. K., et al., "Suppressors of trp1 Fluorescence Identify a New Arabidopsis Gene, TRP4, Encoding the Anthranilate Synthase beta Gene," *The Plant Cell*, 5, 1011–1027 (1993).

Niyogi, K. K., et al., "Two Anthranilate Synthase Genes in Arabidopsis: Defense–Related Regulation of the Tryptophan Pathway," *The Plant Cell*, 4, 721–733 (1992).

Flavell, R., et al., "Prospects for Transforming Monocot Crop Plants", *Nature*, 307, 108–109 (Jan. 12, 1984).

Goodman, R.M., et al., "Gene Transfer in Crop Improvement", *Science*, 236, 48–54 (Apr. 3, 1987).

Jahne, A., et al., "Genetic Engineering of Cereal Crop Plants: A Review", *Euphytica*, 85, 35–44 (1995).

Paszkowski, J., et al., "Direct Gene Transfer to Plants", *The EMBO Journal*, 3, 2717–2722 (1984).

Poehlman, J.M., "Backcross Breeding", In: *Breeding Field Crops*, 3rd Edition, AVI Publishing Company, Inc., Westport, CT, 203–206 (1988).

Potrykus, I., et al., "Direct Gene Transfer to Cells of a Graminaceous Monocot", *Mol. Gen. Genet.*, 199, 184–188 (1985).

Andrews, D.L., et al., "Characterization of the Lipid Acyl Hydrolase Activity of the Major Potato (*Solanum tuberosum*) Tuber Protein, Patatin, by Cloning and Abundant Expression in a Baculovirus Vector", *Biochem. J.*, 252, 199–206 (1988).

Atanassova, R., et al., "A 126 bp Fragment of Plant Histone Gene Promoter Confers Preferential Expression in Meristems of Transgenic Arabidopsis", *The Plant J.*, 2, 291–300 (1992).

Botterman, J., et al., "Engineering Herbicide Resistance in Plants", *Trends in Genet.*, 4, 219–222 (Aug. 1988).

Brignon, P., et al., "Nuclease Sensitivity and Functional Analysis of a Maize Histone H3 Gene Promoter", *Plant Mol. Biol.*, 22, 1007–1015 (1993).

Datta, S.K., et al., "Genetically Engineered Fertile Indica–Rice Recovered from Protoplasts", *Bio/Technology*, 8, 736–740 (Aug. 1990).

Holmstrom, K.–O., et al., "Production of the *Escherichia coli* Betaine–Aldehyde Dehydrogenase, an Enzyme Required for the Synthesis of the Osmoprotectant Glycine Betaine, in Transgenic Plants", *The Plant J.*, 6, 749–758 (1994).

Hooykaas–Van Slogteren, G.M.S., et al., "Expression of Ti Plasmid Genes in Monocotyledonous Plants Infected with *Agrobacterium tumefaciens"*, *Nature*, 311, 763–764 (Oct. 25, 1984).

Jaynes, J.M., et al., "Plant Protein Improvement by Genetic Engineering: Use of Synthetic Genes", *Trends Biotech.*, 4, 314–320 (Dec. 1986).

Kavi Kishor, P.B., et al., "Overexpression of Delta$^1$–Pyrroline–5–Carboxylate Synthetase Increases Proline Production and Confers Osmotolerance in Transgenic Plants", *Plant Physiol.*, 108, 1387–1394 (1995).

Mariani, C., et al., "Engineered Male Sterility in Plants", Symposia of the Society for Experimental Biology, No. XLV, Proceedings of a Meeting Held at the University of Glasgow, Scotland, pp. 271–279 (1991).

McCue, K.F., et al., "Drought and Salt Tolerance: Towards Understanding and Application", *TIBTECH*, 8, 358–362 (Dec. 1990).

Ranch, J.P., et al., "Expression of 5–Methyltryptophan Resistance in Plants Regenerated from Resistant Cell Lines of *Datura innoxia"*, *Plant Physiol.*, 71, 136–140 (1983).

Rathinasabapathi, B., et al., "Metabolic Engineering of Glycine Betaine Synthesis: Plant Betaine Aldehyde Dehydrogenases Lacking Typical Transit Peptides are Targeted to Tobacco Chloroplasts Where They Confer Betaine Aldehyde Resistance", *Planta*, 193, 155–162 (1994).

Saneoka, H., et al., "Salt Tolerance of Glycinebetaine–Deficient and –Containing Maize Lines", *Plant Physiol.*, 107, 631–638 (1995).

Shen, B., et al., "Partial Sequencing and Mapping of Clones from Two Maize cDNA Libraries", *EMBL Sequence Data Library*, Heidelberg, Germany (Oct. 1, 1994).

Vasil, V., et al., "Regeneration of Plants from Embryogenic Suspension Culture Protoplasts of Wheat (*Triticum aestivum* L.)", *Bio/Technology*, 8, 429–434 (May 1990).

Xu, D., et al., "Expression of a Late Embryogenesis Abundant Protein Gene, HVA1, from Barley Confers Tolerance to Water Deficit and Salt Stress in Transgenic Rice", *Plant Physiol.*, 110, 249–257 (1996).

Bohlmann, J., et al., "Purification and cDNA cloning of anthranilate synthase from *Ruta graveolens:* modes of expression and properties of native and recombinant enzymes", *The Plant Journal*, 7(3), pp. 491–501, (1995).

Li, J., et al., "The *arabidopsis thaliana* trp5 Mutant has a feedback–resistant anthranilate synthase and elevated soluble tryptophan", *Plant Physiol.*, 110, pp. 51–59, (1996).

Shen, B., et al., "Partial sequencing and mapping of clones from two maize cDNA libraries", *Plant Molecular Biology*, vol. 26, pp. 1085–1101, (1994).

International Search Report for (Application No. PCT/US 97/00983), completed Jun. 12, 1997 by Examiner Holtorf (3 pages).

Abstracts, 35th Annual Maize Genetics Conference, In Vitro Cellular Devel. Biol., 28:(3) (1992).

"'Bullets" Transform Plant Cells," *Agricell Report*, 9, 5, (Jul. 1987).

"BioTechnica Applies for Field Test of Genetically Engineered Corn," *Genetic Technology News*, 10(3), (Mar. 1990).

Catalog, *Handbook of Fine Chemicals*, Aldrich Chem. Co., p. 508 (1988).

"Chipping Away at Old Weed Enemies," Farm Science Outlook, *Prairie Farmer 162*, 34 (Feb. 20 1990).

"Corn Transformers Multiply," *Bio/Technol.*, 8, 490 (Jun. 1990).

"Cornell U. Gene Gun Hits Biotech Bullseye," *Agriculture Technology*, p. 13.

"Dalapon," Merck Index, 11th edition, S. Budavae, (ed.), Merck and Co., pp. 405–406 (1989).

"DeKalb Researchers Produce Fertile Corn Plants with Foreign Genes," *ARI Newsletter* (Oct./Nov. 1990).

Dialog Search of Japanese Patent No. 61–134343 (1986).

EPO Notice Regarding Publication of Bibliographic Data for EPO 0485506 (1992).

"Gene Guns Succeed in Altering Corn," *Biotechnology News*, p. 2 (Apr. 1990).

"Genetic Engineering Advance Announced for Corn Plants," *Investor's Daily*, (Apr. 19, 1990).

"Genetically Engineered Corn: Breakthrough Brings Market Closer," *Genetic Technology News*, 8–11 (Oct. 1990).

"Herbicide–Resistant Corn" CT Academy of Science and Engineering, Case Reports, 5(4), 6 (1990).

International Search Report, PCT/US 90/04462, mailed Jan. 15, 1991.

International Search Report, PCT/US 90/09699, mailed Aug. 16, 1995.

International Society for Plant Molecular Biology, Program and Abstracts, Molecular Biology of Plant Growth and Development, Tuson, Arizona, Oct. 6–11 (1991).

"Keystone Crops," *Agricultural Genetics Report*, (Mar./Apr. 1990).

Patent Family Record for Australian Patent 87 80 893.

"Plant Science Research, Inc. Achieves Successful Transformation of Corn," *Genetic Engineering News*, 10(3), 3 (Mar. 1990).

"Shotgunning DNA into Cells," *Genetic Engineering News*, (Jul./Aug. 1987).

"Sticky Ends," Genetic Engineering News, 10(5), 1 (May 1990).

"Teams from USDA/Monsanto and DeKalb Genetically Engineer Corn," *Genetic Technology News*, 10(5) (May 1990).

"Two Teams Succeed in Putting Foreign Genes in Corn Plants," *Genetic Engineering Letter*, 10(8), 3 (Apr. 24, 1990).

"USDA Approves More Field Tests," *Genetic Technololgy News*, 11(7), 12 (Jul. 1991).

"USDA Approves Field Test for BioTechnica's Genetically Engineered Corn," *Genetic Technology News*, 10(7), 6 (Jul. 1990).

Adang, M. J., et al., "Characterized Full–Length and Truncated Plasmid Clones of the Crystal Protein of *Bacillus thuringiensis* subsp. *kurstaki* HD–73 and Their Toxicity to *Manduca sexta*," *Gene*, 36, 289–300 (1985).

Ahokas, H. "Transfection of Germinating Barley Seed Electrophoretically with Exogenous DNA," *Theor. Appl. Genet.*, 77, 469–472 (1989).

Ahokes, H. "Electrophoretic transfection of cereal grains with exogenous nucleic acid," Soc. Biochem. Biophys. Microbio. Fen., Biotieteen Paivat (Bioscience Days), Abstracts, Technical University of Helsinki, Espoo, p. 2 (1989).

Akella, V., et al., "Expression in Cowpea Seedings of Chimeric Transgenes after Electroporation into Seed–Derived Embryos," *Plant Cell Rep.*, 12, 110–117 (1993).

Altenbach, S. B., et al., "Enhancement of the Methionine Content of Seed Proteins by the Expression of a Chimeric Gene Encoding a Methionine–Rich Protein in Transgenic Plants," *Plant Mol. Biol.*, 13, 513–522 (1989).

Altenbach, S. B., et al., "Cloning and Sequence Analysis of a cDNA Encoding a Brazil Nut Protein Exceptionally Rich in Methionine," *Plant Mol. Biol.*, 8, 239–250 (1987).

Ampe, C., et al., "The Amino–Acid Sequence of the 2S Sulphur–Rich from Seed of Brazil Nut (*Bertholletia excelsa* H.B.K.)," *Eur. J. Biochem.*, 159, 597–604 (1986).

Armstrong, C. L., et al., "Establishment and Maintenance of Friable, Embryogenic Maize Callus and the Involvement of L–Proline," *Planta*, 164, 207–214 (1985).

Armstrong, C. L., et al., "Genetic and cytogenetic variation in plants regenerated from organogenic and friable, embryonic tissue cultures of maize," *Biological Abstracts*, vol. 85, Abstract No. 117662 (1988).

Aves, K., et al., Transformation of an Elite Maize Inbred Through Microprojectile Bombardment of Regenerable Embryonic Callus, *In Vitro Cell. Develop. Biol.*, 28A, p. 124A, Abstract No. P–1134 (1992).

Bao–Jian, L., et al., "Introduction of Foreign Genes into the Seed Embryo Cells of Rice by Electroinjection and the Regeneration of Transgenic Rice Plants," *Science in China*, 34, 925–931 (1991).

Barker, R. F., et al., "Nucleotide Sequence of the T–DNA Region from the *Agrobacterium tumefaciens* Octopone Ti Plasmid pTil5955," *Plant Mol. Biol.*, 2, 335–350 (1983).

Belanger, F. C., et al., "Molecular Basis for Allelic Polymorphism of the Maize Globulin–1 Gene" *Genetics*, 129, 863–872 (1991).

Benner, M. S., et al., "Genetic Analsis of Methionine–Rich Storage Protein Accumulation in Maize," *Theor. Appl. Genet.*, 78, 761–767 (1989).

Bevan, M., et al., "A Chimaeric Antibiotic Resistance Gene as a Selectable Marker for Plant Cell Transformation," *Nature*, 304, 184–187 (1983).

Bevan, M., et al., "Structure and Transcription of the Nopaline Synthase Gene Region of T–DNA," *Nuc. Acids Res.*, 11, 369–385 (1983).

Binns, A N.,"Agrobacterium–mediated gene delivery and the biology of host range limitations," *Physiologia Plantarum*, 79, 135–139 (1990).

Bishop, J. E., "Two Teams Plane Genes into Corn," *The Wall Street Journal*, B1 (Apr. 1990).

Bohnert, H. J., "Coping with Water Deficit—Application of Biochemical Principles," 1995 Plant Physiology Meeting, Abstract No. 20003 (1995).

Bohnert, H. J., et al., "Adaptations to Environmental Stresses," *The Plant Cell*, 7, 1099–1111 (1995).

Booy, G., et al., "Attempted Pollen–Mediated Transformation of Maize," *J. Plant Physiol.*, 135, 319–324 (1989).

Boulton, M. I., et al., "Specificity of Agrobacterium–mediated delivery of maize streak virus DNA to members of the Gramineae," *Plant Molecular Biology*, 12, 31–40 (1989).

Boyer, J. S., "Water Deficits and Photosynthesis," In: *Water Deficits and Plant Growth*, vol. IV, Kozlowski, T. T., (ed.), Academic Press, New York, pp. 153–190 (1976).

Brill, W. J., "Agricultural Microbiology," *Scientific American*, 245(3), 199–215 (Sep. 1981).

Brunke, K. J., et al., "Insect Control with Genetically Engineered Crops," *Trends in Biotechnol.*, 9, 197–200 (1991).

Buchanan–Wollaston, V., et al., "Detoxification of the Herbicide Dalapon by Transformed Plants," *J. of Cell. Biochem.*, 13D, p. 330, Abstract No. M503 (1989).

Callis, J., et al., "Introns Increase Gene Expression in Cultures Maize Cells," *Genes and Development*, 1, 1183–1200 (1987).

Cao, J., et al., "Transformation of Rice and Maize Using the Biolistic Process," In:*Plant Gene Transfer*, Alan R. Liss, Inc., pp. 21–33 (1990).

Carpita, N. C., "The Biochemistry of "Growing" Cell Walls," In: *Physiology of Cell Expansion During Plant Growth,* Cosgrove, D. J., et al., (eds.) Am. Soc. Plant Physiol., pp. 28–100 (1987).

Chan, M.-T., et al., "Agrobacterium–Mediated Production of Transgenic Rice Plants Expressing a Chimeric α–Amylase Promoter/β–Glucuronidase Gene," *Plant Mol. Biol.,* 22, 491–506 (1993).

Chandler, V. L., et al., "Two Regulatory Genes of the Maize Anthocyanin Pathway are Homologous: Isolation of B Utilizing R Genomic Sequences," *The Plant Cell,* 1, 1175–1183 (1989).

Charest, P. J., et al., "Factors Affecting the Use of Chloramphenical Acetyltransferase as a Marker for Brassica Genetic Transformation", *Plant Cell Reports,* 7, 628–631 (1989).

Chasan, R., "Transforming Maize Transformation," *The Plant Cell,* 4, 1463–1464 (1992).

Chourey, P. S., et al., "Callus Formation from Protoplasts of a Maize Cell Culture," *Theor. Appl. Genet.,* 59, 341–344 (1981).

Christou, P., et al., "Opine Synthesis in Wild–Type Plant Tissue," *Plant Physiol.,* 82, 218–221 (1986).

Christou, P., et al., "Soybean Genetic Engineering—Commercial Production of Transgenic Plants," *Trends Biotechnol.,* 8, 145–151 (1990).

Christou, P., et al., "Cotransformation Frequencies of Foreign Genes in Soybean Cell Cultures," *Theor. Appl. Genet.,* 79, 337–341 (1990).

Christou, P., et al., "Genetic Transformation of Crop Plants Using Microprojectile Bombardment," *The Plant Journal,* 2, 275–281 (1992).

Christou, P., et al., "Stable Transformation of Soybean Callus by DNA–Coated Gold Particles," *Plant Physiol.,* 87, 671–674 (1988).

Chu, C.-C., et al., "Establishment of an Efficient Medium for Anther Culture of Rice Through Comparative Experiments on the Nitrogen Sources," *Sci. Sin. (Peking),* 13, 659–668 (1975).

Clark, B., "Biotech Advance in Corn: Gunslinging Researchers Fire Marker Genes in to Corn," *AG Consultant,* 46(7), 12 (Jul. 1990).

Cocking, F., et al., "Gene Transfer in Cereals," *Science,* 236, 1259–1262 (1987).

Coe et al., "The Genetics of Corn" In: *Corn and Corn Improvement,* 2nd edition, Sprague, G. F., (ed.), American Soc. Agronomy, Inc, Madison, WI, p. 138 (1977).

Comai, L., et al., "Expression in Plants of a Mutant aroA Gene from *Salmonella typhimurium* Confers Tolerance to Glyphosate," *Nature,* 317, 741–744 (Oct., 1985).

Creissen, G., et al., "Agrobacterium– and Microprojectile–Mediated Viral DNA Delivery into Barley Microspore Derived–Cultures," *Plant Cell Rep.,* 8, 680–683 (Apr. 1990).

Crossway, A., et al., "Integration of foreign DNA following microinjection of tobacco mesophyll protoplasts," *Mol. Gen. Genet.,* 202, 179–185 (1986).

D'Halluin, K., et al., "Transgenic Maize Plants by Tissue Electroporation," *The Plant Cell,* 4, 1495–1505 (1992).

Darvill, A., et al., "The Primary Cell Walls of Flowering Plants," In: *The Biochemistry of Plants,* vol. 1, pp. 91–162 (1980).

Dauce–LeReverand, B., et al., "Improvement of *Escherichia coli* Strains Overproducing Lysine Using Recombinant DNA Techniques," *Eur. J. Appl. Microbiol. Biotechnol.,* 15, 227–231 (1982).

De Block, M., et al., "Engineering herbicide resistance on plants by expression of a detoxifying enzyme," *EMBO J.,* 6, 2513–2518 (1987).

De Greef, W., et al., "Evaluation of herbicide resistance in transgenic crops under field conditions," *Bio/Technol.,* 7, 61–64 (1989).

DeKeyser, R. A., et al., "Evaluation of Selectable Markers for Rice Transformation," *Plant Physiol.,* 90, 217–223 (1989).

Dekeyser, R. A., et al., "Transient Gene Expression in Intact and Organized Rice Tissues," *The Plant Cell,* 2, 591–602, (1990).

DeWald et al., "Plant regeneration from inbred maize suspensions," VIIth International Congress on Plant Tissue and Cell Culture, p. 12, Abstract No. A1–36 (Jun. 24–29, 1990).

DeWet, J. M. J.,et al.; "Exogenous gene transfer in maize (*Zea mays*) using DNA–treated pollen;" In: *The experimental manipulation of ovule tissues.* Chapman, G. P., et al., (eds.), Longman, New York, pp. 197–209 (1985).

DeWet, J. R. et al., "Cloning of Firefly Luciferase cDNA and the Expression of Active Luciferase in *Escherichia coli,*" *Proc. Nat. Acad. Sci. USA,* 82, 7870–7873 (1985).

Donn, G., et al., "Stable Transformation of Maize with a Chimaeric, Modified Phosphinothricin–Acetyltransferase Gene from *Streptomyces viridochromogenes,*" Abstracts, VIIth International Congress Plant Tissue Cell Culture, p. 53, Abstract No. A2–38 (Jun. 24–29, 1990).

Dupuis, I., et al., "Gene Transfer to Maize Male Reproductive Structure by Particle Bombardment of Tassel Primordia," *Plant Cell Rep.,* 12, 607 (1993).

Ellis, J. G., et al., "Does the OCS–Element Occur as a Functional Component of the Promotors of Plant Genes?" *EMBO J.,* 6, 3203–3208 (1987).

Evans, D. A., et al., "Somaclonal Variation—Genetic Basis and Breeding Applications," *Trends Genet.,* 5, 46–50 (1989).

Fennel, A., et al., "Electroporation and PEG Delivery of DNA into Maize Microspores," *Plant Cell Reports,* 11, 567–570 (1992).

Finnegan, J., et al., "Transgene Inactivation: Plants Fight Back!" *Bio/Technol.,* 12, 883–888 (Sep., 1994).

Fitzpatrick, T., "Pleiotrophic Gene Found in Barley Plant," *Genetic Engineering News,* 13, 1 (1993).

Fransz, P., et al., "Cytodifferentiation during callus initiation and somatic embryogenesis in *Zea mays* L.," Ph.D. thesis, U. of Wageningen Press, The Netherlands (1988).

Freeling, J.C., et al., "Developmental Potentials of Maize Tissue Cultures," *Maydica,* XXL, 97–112 (Jul. 1977).

Freiberg, "More Researchers Discover Corn Transformation Technology," *AG Biotechnology News,* p. 26 (1990).

Fromm, M. E., et al., "Inheritance and Expression of Chimeric Genes in the Progeny of Transgenic Maize Plants," *Bio/Technol.,* 8, 833–839 (1990).

Fromm, M. E., et al., "Stable Transformation of Maize after Gene Transfer by Electroporation," *Nature,* 319, 791–793 (1986).

Fromm, M., et al., "Expression of Genes Transfected into Monocot and Dicot Plant Cells by Electroporation," *Proc. Nat. Acad. Sci. USA,* 82, 5824–5828 (1985).

Fry, S.C., "Introduction to the Growing Cell Wall," In: *The Growing Plant Cell Wall: Chemical and Metabolic Analysis,* Longman Scientific and Technical, New York, pp. 1–5, 102–109 (1988).

Geiser, M., et al., "Hypervariable Region on the Genes Coding for Entomopathogenic Crystal Proteins of *Bacillus thuringiensis:* Nucleotide Sequence of the kurhd1 gene of subsp. *kurstaki* HD1," *Gene,* 48, 109–118 (1986).

Goff, S. A., et al., "Plant Regeneration of Anthocyanin Biosynthetic Genes Following Transfer of B Regulatory Genes into Maize Tissues," *EMBO J.,* 9, 2517–2522 (1990).

Gordon–Kamm, W. J., et al., "Stable Transformation of Embryonic Maize Cultures by Microprojectile Bombardment," *J. Cellular Biochem.,* 13D, p. 259, Abstract No. M122 (1989).

Gordon–Kamm, W. J., et al., "Transformation of Maize Cells and Regeneration of Fertile Transgenic Plants," *The Plant Cell,* 2, 603–618 (1990).

Gould, J., et al., "Transformation of the Graminae by *Agrobacterium tumefaciens,*" Int. Soc. Plant Mol. Biol. 3rd Int. Congress, Abstract No. 1277 (1991).

Gould, O., et al., "Shoot Tip Culture as a Potential Transformation System," Abstracts, Beltwide cotton production research conferences, New Orleans, LA, p. 91 (1988).

Gould, J., et al., "Transformation of *Zea mays* L. Using *Agrobacterium tumefaciens* and the Shoot Apex," *Plant Physiol.,* 95, 426–434 (1991).

Graves, A., et al., "The transformation of *Zea mays* seedlings with *Agrobacterium tumefacians,*" *Plant Mol. Biol.* 7, 43–50 (1986).

Green, C., et al., "Plant Regeneration from Tissue Cultures of Maize," *Crop. Sci.,* 15, 417–421 (1975).

Green, C., et al., "Plant Regeneration in Tissue Cultures of Maize," In: *Maize for Biological Research,* Sheridan, W. F., (ed.) Plant Mol. Biol. Assoc., pp. 367–372 (1982).

Green, C., et al., "Somatic Cell Genetic Systems in Corn," In: *Advances in Gene Technology: Molecular Genetics of Plant and Animals,* Academic Press, Inc., pp. 147–157 (1983).

Grimsley, N., et al., "DNA Transfer from Agrobacterium to *Zea mays* or Brassica by Agroinfection is Dependent on Bacterial Virulence Functions," *Mol. Gen. Genet.,* 217, 309–316 (1989).

Gritz, L., et al., "Plasmid–Encoded Hygromycin B Resistance: The Sequence of Hygromycin B Phosphotransferase Gene and Its Expression in *Escherichia coli* and *Saccharomyces cerevisiae,*" *Gene,* 25, 179–188 (1983).

Guerineau, F., et al., "Sulfonamide Resistance Gene for Plant Transformation," *Plant Molecular Biology,* 15, 127–136 (1990).

Guilley, H., et al., "Transcription of Cauliflower Mosaic Virus DNA: Detection of Promoter Sequences, and Characterization of Transcripts," *Cell,* 30, 763–773 (Oct. 1982).

Gunset, G., "Genetic Advance May Transform Corn," *Chicago Tribune* (Apr. 19, 1990).

Gunset, G., "Corn Farmers See Economic, Environmental Gold in Designer Genes," *Chicago Tribune* (Jan. 21, 1991).

Hallauer, A. R., et al., "Corn Breeding," In: *Corn and Corn Improvement,* 3rd edition, Sprague, G. F., et al., (eds.), Agronomy Soc. Amer., pp. 463–564 (1988).

Haughn, G. W., "Transformation with a Mutant Arabidopsis Acetolactate Synthase Gene Renders Tobacco Resistant to Sulfonylurea Herbicides," *Mol. Gen. Genet.,* 211, 266–271 (1988).

Hauptman, R. M., et al., "Evaluation of Selectable Markers for Obtaining Stable Transformants on the Gramineae," *Plant Physiol.,* 86, 602–607 (1988).

Herrera–Estrella, L., et al., "Use of Reporter Genes to Study Gene Expression in Plant Cells", In: Plant Molecular Biology Manual B1, Kluwer Academic Publishers, Dordrecht, pp. 1–22 (1988).

Hiel, Y., et al., "Efficient Transformation of Rice (*Oryza sativa* L.) Mediated by Agrobacterium and Sequence Analysis of the Boundaries of the T–DNA," The Plant J., 6, 271–282 (1994).

Hoffman, L. M., et al., "A Modified Storage Protein is Synthesized, Processed, and Degraded in the Seeds of Transgenic Plants," *Plant Mol. Biol.,* 11, 717–729 (1988).

Hoffman, L. M., et al., "Synthesis and Protein Body Deposition of Maize 15kD Zein in Transgenic Tobacco Seeds," *EMBO J.,* 6, 3213–3221 (1987).

Hofte, H., et al., "Insecticidal Crystal Proteins of *Bacillus thuringiensis,*" *Microbiol. Rev.,* 53, 242–255 (1989).

Hong, B., et al., "Developmental and Organ–Specific Expression of an ABA– and Stress–Induced Protein in Barley," *Plant Mol. Biol.,* 18, 663–674 (1992).

Hooykaas, P. J. J., "Transformation of plant cell via Agrobacterium," *Plant Mol. Biol.,* 13, 327–336 (1989).

Horn, M., et al., "Transgenic Plants of Orchard Grass (*Dactylis glomerata* L.) from Protoplasts," *Chem. Abstracts,* 110, p. 208, Abstract No. 89869a (1989).

Horn, M., et al., "Transgenic Plants of Orchardgrass (*Dactylis glomerata* L.) from Protoplasts," *Plant Cell Reports,* 7, 469 (1988).

Howe, A., et al., "Development of Glyphosphate as a Selectable Marker for the Production of Fertile Transgenic Corn Plants," *In Vitro Cell. Develop. Biol.,* 28A, p. 124A, Abstract No. P–1136 (Jul.–Aug. 1992).

Huang, Y., et al., "Factors Influencing Stable Transformation of Maize Protoplasts by Electroporation," *Plant Cell. Tissue and Organ Culture,* 18, 281 (1989).

Imbrie–Milligan, C., et al., "Microcallus Growth from Maize Protoplasts," *Planta,* 171, 58–64 (1987).

Jahne, A., et al., "Regeneration of Fertile Plants from Protoplasts Derived From Embryogenic Cell Suspensions of Barley (*Hordeum vulgare* L.)," *Plant Cell Rep.,* 10, 1–6 (1991).

Jayne, S., et al., "Analysis of Elite Transgenic Maize Plants Produced by Microprojectile Bombardment," Program and Abstracts, Int. Soc. for Plant Mol. Biol., 3rd Int. Cong., Abstract No. 338 (Oct. 6–11, 1991).

Jefferson, R,. et al., "β–Glucuronidase from *Escherichia coli* as a Gene–Fusion Marker," *Proc. Nat. Acad. Sci. USA,* 83, 8447–8451 (1986).

Jefferson, R., et al., "GUS Fusions: β–Glucuronidase as a Sensitive and Versatile Gene Fusion Marker in Higher Plants," *EMBO J.,* 6, 3901–3907 (1987).

Jefferson, R., "Assaying chimeric genes in plants: the GUS gene fusion system," *Plant Mol. Biol. Rep.,* 5, 387–405 (1987).

Jones, H., et al., "Recent Advances in Plant Electroporation," *Oxford Surveys of Plant Molecular and Cell Biol.,* 4, 347–357 (1987).

Jones, H., et al., "Transient Gene Expression in Electroporated Solanum Protoplasts," *Plant Mol. Biol.,* 13, 503–511 (1989).

Johri, M. M. et al., "Genetic Approaches to Meristem Organization", In: *Maize for Biological Research,* W. F. Sheridan, (ed.), Plant Molecular Biology Association, pp. 301–310 (1982).

Kaeppler, H. F., et al., "Silicon Carbine Fiber–Mediated DNA Delivery into Plant Cells," *Plant Cell Rep.*, 9, 415–418 (1990).

Kamo, K., et al., "Establishment and Characterization of Long–Term Embryonic Maize Callus and Cell Suspension Cultures," *Plant Sci.*, 45, 111–117 (1986).

Kamo, K, et al., "Regeneration of *Zea mays* L. from Embryogenic Callus," *Bot. Gaz.*, 146, 327–334 (1985).

Kao, K. N., et al., "Nutritional Requirements for Growth of *Vicia hajastana* Cells and Protoplasts at a Very Low Population Density in Liquid Media," *Planta*, 126, 105–110 (1978).

Kartha, K., et al., "Transient Expression of Chloramphenicol Acetyl Transferase (CAT) Gene in Barley Cell Cultures and Immature Embryos Through Microprojectile Bombardment," *Plant Cell Rep.*, 8, 429–432 (1989).

Kay, R., et al., "Duplication of CaMV 35S Promoter Sequences Creates a Strong Enhancer for Plant Genes," *Science*, 236, 1299–1302 (Jun. 5, 1987).

Kirihara, J., et al., "Differential Expression of a Gene for a Methionine–Rich Storage Protein in Maize," *Mol. Gen. Genet.*, 211, 477–484 (1988).

Kirihara, J., et al., "Isolation and Sequence of a Gene Encoding a Methionine–Rich 10–kD Zein Protein from Maize," *Gene*, 71, 359–370 (1988).

Klein, T., et al., "Transfer of Foreign Genes into Intact Maize Cells with High–Velocity Microprojectiles," *Proc. Nat. Acad. Sci. USA*, 85, 4305–4309 (1988).

Klein, T. M., et al., "Factors Influencing Gene Delivery into *Zea mays* Cells by High Velocity Microprojectiles," *Bio/Technol.*, 6, 559–563 (1988).

Klein, T. M., et al., "High–Velocity Microprojectiles for Delivering Nucleic Acids to Living Cells," *Nature*, 327, 70–73 (1987).

Klein, T., et al., "Genetic Transformation of Maize Cell by Particle Bombardment and the Influence of Methylation on Foreign Gene Expression," In: *Gene Manipulation in Plant Improvement II*, Gustafson, J. P., (ed.), Plenum Press, NY, pp. 265–266 (1990).

Klein, T., et al., "Genetic transformation of Maize Cells by Particle Bombardment," *Plant Physiol.*, 91, 440–444 (1989).

Klein, T., et al., "Regulation of Anthocyanin Biosynthetic Genes Introduced into Intact Maize Tissue by Microprojectiles," *Proc. Nat. Acad. Sci. USA*, 86, 6682–6685 (1989).

Kozak, M., "Compilation and Analysis of Sequence from the Translational Start Site in Eukaryotic mRNAs" *Nuc. Acids. Res.*, 12, 857–871 (1984).

Kozak, M., "Point Mutations Define a Sequence Flanking the AUG Initiator Codon that Modulates Translation by Eukaryotic Ribonsomes," *Cell*, 44, 283–292 (1986).

Koziel, M. G., et al., "Field Performance of Elite Transgenic Maize Plants Expressing an Insecticidal Protein Derived from *Bacillus thuringenesis*," *Bio/Technol.*, 11, 194–200 (1993).

Kreitlow, B., "Genetic Engineering 'Breakthrough' Disputed," Cedar Rapids Gazette (Apr. 20, 1990).

Kriz, A. L., et al., "Characterization of the Maize Globulin–2 Gene and Analysis of Two Null Alleles," *Biochemical Genetics*, 29, 241–254 (1991).

Kuhlemeier, C., et al., "Regulation of Gene Expression in Higher Plants," *Ann. Rev. Plant Physiol.*, 38, 234–239 (1987).

Landi, P., et al., "Genetic Analysis of Leaf ABA Concentration and of Agronomic Traits in Maize Hybrids Grown Under Different Water Regimes," *Maydica*, 40, 179–186 (1995).

Langridge, et al., "Transformation of Cereals via Agrobacterium and the Pollen Pathway: A Critical Assessment," *The Plant J.*, 2, 613–638 (1992).

Laursen, C. M., et al., "Production of Fertile Transgenic Maize by Electorporation of Suspension Culture Cells," *Plant Mol. Biol.*, 24, 51–61 (1994).

Lazzeri, P., et al., "In Vitro Genetic Manipulation of Cereals and Grasses," *Ad. Cell Culture*, 6, 291–293 (1988).

Lee, J. S., et al., "Gene Transfer into Intact Cells of Tobacco by Electroporation," *Korean J. Gent.*, 11, 65–72 (1989).

Leemans, J., "Genetic Engineering for Fertility Control," Keystone Symposium on Crop Improvement via Biotechnology: An International Perspective, Abstract No. Y016 (Apr. 10–26, 1992).

Levitt, J., "Growth Regulators" In: *Introduction to Plant Physiology*, The C. V. Mosby Company, St. Louis, p. 241 (1969).

Li, X.–Q., et al., "GUS Expression in Rice Tissues Using Agrobacterium–Mediated Transformation," Program and Abstracts, Int. Soc. for Plant Mol. Biol., 3rd Int. Cong., Abstract No. 385 (Oct. 6–11, 1991).

Lindsey, K., et al., "Electroporation of Cells," *Physiologia Plantarum*, 79, 168–172 (1990).

Lindsey, K., et al., "The Permeability of Electroporated Cells and Protoplasts of Sugar Beet," *Planta*, 172, 346–355 (1987).

Lindsey, K., et al., "Transient Gene Expression in Electroporated Protoplasts and Intact Cells of Sugar Beet," *Plant Mol. Biol.*, 10, 43–52 (1987).

Lindsey, K. et al., "Stable Transformation of Sugarbeet Protoplasts by Electroporation," *Plant Cell Rep.*, 8, 71–74 (1989).

Looker, D., "Dekalb Claims Success in Effort to Alter Genetic Makeup of Corn," *Des Moines Register* (Apr. 19, 1990).

Lopes, M. A., et al., "Endosperm Origin, Development, and Function," *The Plant Cell*, 5, 1383–1399 (1993).

Lorz, H., et al., "Advances in Tissue Culture and Progress Towards Genetic Transformation of Cereals," *Plant Breeding*, 100, 1–25 (1988).

Lu, C., et al., "Somatic Embryogenesis in *Zea mays* L.," *Theor. Appl. Genet.*, 62, 109–112 (1982).

Lu, C., et al., "Improved Efficiency of Somatic Embryogenesis and Plant Regeneration on Tissue Cultures of Maize (*Zea mays* L.)," *Theor. Appl. Genet.*, 66, 285–289 (1983).

Ludwig, S., et al., "A Regulatory Gene as a Novel Visible Marker for Maize Transformation," *Science*, 247, 449–450 (1990).

Ludwig, S., et al., "High Frequency Callus Formation from Maize Protoplasts," *Theor. Appl. Genet.*, 71, 344–350 (1985).

Ludwig, S., et al., "Lc, a Member of the Maize R Gene Family Responsible for Tissue–Specific Anthocyanin Production, Encodes a Protein Similar to Transcriptional Activators and Contains the myc–Homology Region," *Proc. Nat. Acad. Sci. USA*, 86, 7092–7096 (1989).

Ludwig, S., et al., "Maize R Gene Family: Tissue–Specific Helix–Loop–Helix Proteins," *Cell*, 62, 849–851 (1990).

Lutchke, H., et al., "Selection of AUG Initiation Codons Differs in Plants and Animals," *EMBO J.*, 6, 43–48 (1987).

Maas, C., et al., "A Highly Optimized Monocot Expression Cassette: Application for Barley Transformation and Barley Virus Research," Program and Abstracts, Int. Soc. Plant Mol. Biol., Abstract No. 386 (Oct. 6–11, 1991).

Maddock, S. E., et al., "Expression in Maize Plants of Wheat Germ Agglutinin, a Novel Source of Insect Resistance," Program and Abstracts, Int. Soc. Plant Mol. Biol., 3rd Int. Cong., Abstract No. 372 (Oct. 6–11, 1991).

Masumura, T., et al., "cDNA Cloning of an mRNA Encoding a Sulfur–Rich 10 kDa Prolamin Polypeptide in Rice Seeds," *Plant Mol. Biol.*, 12, 123–130 (1989).

McCabe et al., "Stable Transformation of Soybean (*Glycine max*) by Particle Acceleration," *Bio/Technol.*, 6, 923–926 (1988).

McDaniel, C., et al., "Cell–Lineage Patterns in the Shoot Apical Meristem of the Germinating Maize Embryo," *Planta*, 175, 13–22 (1988).

Meadows, M., "Characterization of Cells and Protoplasts of the B73 Maize Cell Line," *Plant Sci. Lett.*, 28, 337–348 (1982/83).

Mendel, R., et al., "Delivery of Foreign Genes to Intact Barley Cell by High–Velocity Microprojectiles," *Theor. Appl. Genet.*, 78, 31–34 (1989).

Messing, J., "Corn Storage Protein: A Molecular Genetic Model," Division of Energy BioSciences—Summaries of FY 1990 Activities, p. 70, Abstract No. 135 (1990).

Milborrow, B. V., "Abscisic Acid and Other Hormones," In: *The Physiology and Biochemistry of Drought Resistance in Plants*, Paleg, L. G., et al., (eds.), Academic Press, New York, pp. 347–388 (1981).

Moffat, A. S., "Corn Transformed," *Science*, 249, 630 (Aug. 10, 1990).

Morikawa, et al.,"Gene Transfer into Intact Plant Cells by Electroporation Through Cell Walls and Membranes," *Gene*, 41, 121 (1986).

Morocz, S. et al., "An Improved System to Obtain Fertile Regenerants via Maize Protoplasts Isolated From a Highly Embryonic Suspension Culture," *Theor. Appl. Genet.*, 80, 721–726 (1990).

Morocz, S., et al., "Two Approaches to Rendering *Zea mays* L. Applicable to Tissue Culture Manipulations," Abstracts, VIIth Int. Cong. on Plant Tissue and Cell Culture,Amsterdam A1–102, Abstract No. 209, p. 190 (1990).

Murakami, T., et al., "The Bialaphos Biosynthetic Genes of *Streptomyces hygroscopicus*: Molecular Cloning and Characterization of the Gene Cluster," *Mol. Gen. Genet.*, 205, 42–50 (1986).

Murashige, T., et al., A Revised Medium for Rapid Growth and Bio Assays with Tobacco Tissue Cultures, *Physiol. Plant.*, 15, 473–497 (1962).

Murphy, H. L., "New Dekalb–Pfizer Seed Chief to Harvest R & D Breakthroughs," *Crain's Business Weekly*, pp. 38–39 (1990).

Murray, E. E., et al., "Codon usage in plant genes," *Nuc. Acids Res.*, 17, 477–498 (1989).

Murry, L. E., et al., "Transgenic Corn Plants Expressing MDMV Strain B Coat Protein are Resistant to Mixed Infections of Maize Dwarf Mosaic Virus and Maize Chlorotic Mottle Virus," *Bio/Technol.*, 11, 1559–1564 (1993).

Nelson, R. S., "Virus Tolerance, Plant Growth, and Field Performance of Transgenic Tomato Plants Expressing Coat Protein from Tobacco Mosaic Virus," et al., *Bio/Technol.*, 6, 403–409 (1988).

Nelson, T., "New Horses for Monocot Gene Jockeys," *The Plant Cell*, 2, 589 (1990).

Neuffer, "Growing Maize for Genetic Purposes," Maize for Biological Research, Plant Mol. Biol. Assoc., (1988).

Odell, J,. et al., "Identification of DNA Sequences Required for Activity of the Cauliflower Mosaic Virus 35S Promoter," *Nature*, 313, 810–811 (1985).

Office Action dated May 30, 1989, Goldman et al., U.S. application No. 06/880,271, filed Jun. 30, 1986.

Office Action dated Mar. 8, 1990, Goldman, U.S. application No. 06/880,271, filed Jun. 30, 1986.

Ohta, Y., "High–Efficiency Genetic Transformation of Maize by a Mixture of Pollen and Exogenous DNA," *Proc. Nat. Acad. Sci. USA*, 83, 715–719 (1986).

Okta, Y., et al., "Gene Manifestation of Exogenous DNA Applied to Self Propagating Stigma (Gene Action Revealed in the $M_1$ and $M_2$ Generations from Self–Pollination Applying Exogenous DNA)," *Jap. J. Breed.*, 30, 184–185 (1980).

Omirullen, S., et al., "Activity of a Chimeric Promoter with the Doubled CaMV 35S Enhancer in Protoplast–Derived Cells and Transgenic Plants in Maize," *Plant Mol. Biol.*, 21, 415–428 (1993).

Ozias–Akins, P., et al., "In vitro regeneration and genetic manipulation of grasses," *Physiol. Plant.*, 565–569 (1988).

Ozias–Akins, P., et al., "Progress and Limitations in the Culture of Cereal Protoplasts," *Trends in Biotechnol.*, 2, 119–123 (1984).

Park, S. H., et al., "Selection of Maize Transformants form Shoot Apex Cultures Cocultivated with Agrobacterium Containing the Bar Gene," *In Vitro Cell. Develop. Biol.*, 29A, p. 85A, Abstract No. P–1102 (1993).

Parker, W. B., et al., "Selection and Characterization of Sethoxydim–Tolerant Maize Tissue Cultures," *Plant Physiol.*, 92, 1220–1225 (1990).

Pederson, K., et al., "Sequence Analysis and Characterization of a Maize Gene Encoding a High–Sulphur Zein Protein of $M_r$ 15,000," *J. Biol. Chem.*, 261, 6279–6284 (1986).

Perl, A., et al., "Bacterial Dihydrodipicolinate Synthase and Desensitized Aspartate Kinase: Two Novel Selectable Markers for Plant Transformation," *Bio/Technol.*, 11, 715–718 (1993).

Perlack, F. J., et al., "Modification of the Coding Sequence Enhances Plant Expression of Insect Control Protein Genes," *Proc. Nat. Acad. Sci. USA*, 88, 3324–3328 (1991).

Phillips, R. L., et al., "Elevated Protein–Bound Methionine in Seeds of a Maize Line Resistant to Lysine Plus Threonine," *Cereal Chem.*, 62, 213–218 (1985).

Phillips, R. L., et al., "Cell/Tissue Culture and In Vitro Manipulation," In: *Corn and Corn Improvement*, 3rd edition, Sprague, G. F., et al., (eds.), Agronomy Soc. Amer., pp. 345–387 (1988).

Pioneer HiBred International, Inc., Application Under 7 CFR 340, Release of Genetically Engineered Corn Plants, Permit No. 92–174–02, No CBI, p. 8 (Nov. 3, 1992). Pioneer HiBred International, Inc., Application Under 7 CFR 340, Release of Genetically Engineered Corn Plants, Permit No. 92–330–01, CBI–Deleted, p. 13 (Apr. 13, 1993). Philips, R. L., et al., "Elevated Protein–Bound Methionine in Seeds of a Maize Line Resistant to Lysine Plus Threonine," *Cereal Chem.*, 62, 213–218 (1985). Pioneer's Application for Release in the Environment Under 7 CFR 340, Corn Plants Genetically Enginerred to Express Wheat Germ Agglutinin (WGA) Genes, in Order to Confer Resistance to the European Corn Borer (*Ostrinia nubilalis*) and Tolerance to Glufosinate Herbicides, 92–022–03, No CBI Copy, p. 11 (May 4, 1992).

Poehlman, J. "Breeding Corn (Maize)," In: *Breeding Field Crops,* 3rd edition, AVI Publishing Co, Westport CN, pp. 452, 469–471, 477–481 (1986).

Potrykus, I., et al., "Callus Formation from Cell Culture Protoplasts of Corn (*Zea mays* L.)," *Theor. Appl. Genet.,* 54, 209–214 (1979).

Potrykus, I., "Gene Transfer to Cereals: An Assessment," *Bio/Technol.,* 8, 535–542 (Jun. 1990).

Potrykus, I., "Gene Transfer to Cereals: An Assessment," *Trends Biotechnol.,* 7, 269–273 (Oct. 1989).

Potrykus, I., "Gene Transfer to Plants: Assessment and Perspectives," *Physiol. Plant.,* 79, 125–134 (1990).

Potrykus, I., et al., "Callus formation from stem protoplasts sof corn (*Zea mays*L.)" *Mol. Gen. Genet.,* 156, 347–350 (1977).

Potter, et al., "Enhancer–Dependent Expression of Human κ Immunoglobulin Genes Introduced into Mouse Pre–B Lymphocytes by Electroporation," *Proc. Natl. Acad. Sci. USA,* 81, 7161 (1984).

Prioli, L. M., et al., "Plant Regeneration and Recovery of Fertile Plants from Protoplasts of Maize (*Zea mays* L.)," *Bio/Technol.* 7, 589–594 (Jun. 1989).

Puite, K. J., et al., "Electrofusion, a Simple and Reproducible Technique in Somatic Hybridization of *Nicotiana plumbaginifolia* mutants," *Plant Cell Rep.,* 4, 274–276 (1985).

Rasmusen, J. L., et al., "Biolistic Transformation of Tobacco and Maize Suspension Cells Using Bacterial Cells as Microprojectiles," *Plant Cell Rep.,* 13, 212–217 (1994).

Rhodes, C. A., et al., "Genetically Transformed Maize Plants from Protoplasts," *Science,* 240, 204–207 (Apr. 8, 1988).

Rhodes, C. A., et al., "Plant Regeneration from Protoplasts Isolated from Embryogenic Maize Cell Cultures," *Bio/Technol.,* 6, 56–60 (Jan. 1988).

Rhodes, C. A., "Corn: From Protoplasts to Fertile Plants," *Bio/Technol.,* 7, 548 (Jun. 1989).

Richaud, F., et al., "Chromosomal Location and Nucleotide Sequence of the *Escherichia coli* dapA Gene," *Biol. Abstracts,* 82, p. AB–391, Abstract No. 3396 (1986).

Richaud, F., et al., "Chromosomal Location and Nucleotide Sequence of the *Escherichia coli* dapA Gene," *J. Bacteriol.,* 166, 297–300 (1986).

Robbins–Roth et al., "They Make it Happen in Biotech," *Bioworld,* pp. 30–36 (Nov./Dec. 1990).

Robertson, D. S., et al., "Loss of Mu Mutator Activity when Active Mu Systems are Transferred to Inbred Lines," *Maize Genetics Coop. Newsletter,* 60, 10 (1986).

Ross, M.C., et al., "Transient and Stable Transgenic Cells and Calli of Tobacco and Maize Following Microprojectile Bombardment,"*J. Cell. Biochem.,* 13D, p. 268, Abstract No. M149 (1989).

Sahi, S. V., et al., "Metabolites in Maize Which Affect Virulence Induction in *Agrobacterium tumefaciens,"* *Plant Physiol.,* Supplement, p. 86, Abstract No. 514, (1989).

Sanford, J. C., "Biolistic Plant Transformation," *Physiol. Plant.,* 79, 206–209 (1990).

Sanford, J. C., "The Biolistic Process," *Trends Biotechnol.,* 6, 299–302 (1988).

Sanford, J. C., et al., "Attempted Pollen–Mediated Plant Transformation Employing Genomic Donor DNA," *Theor. Appl. Genet.,* 69, 571–574 (1985).

Sanford, J. C., et al., "Delivery of Substances into Cells and Tissues Using a Particle Bombardment Process," *Particulate Sci. Technol.,* 5, 27–37 (1987).

Sass, "Morphology: Development of the Caryopsis" In: *Corn and Corn Improvement,* 2nd edition, Sprauge, G. F., (ed.), American Soc. Agronomy, p. 89, 98 (1977).

Schmidt, A., et al., "Media and environmental effects of phenolics production from tobacco cell cultures," *Chem. Abstracts,* 110, p. 514, Abstract No. 230156z (1989).

Shen, W.–H., et al., "Excision of a Transposible Element form a Viral Vector Introduced into Maize Plants by Agroinfection," *The Plant J.,* 2, 35–42 (1992).

Shen, W.–H., et al., "Amplification and expression of the β–glucuronidase gene in maize plants by vectors based on maize streak virus," *The Plant Journal,* 5, 227–236 (1994).

Shigekawa, K., et al., "Electroporation of Eukaryotes and Prokaryotes: A General Approach to the Intoduction of Macromolecules into Cells," *BioTechniques,* 6, 742–751 (1988).

Shillito, R. D., et al., "High Efficiency Direct Gene Transfer to Plants," *Bio/Technol.,* 3, 1099 (1985).

Shillito, R. D., et al., "Regeneration of Fertile Plants From Protoplasts of Elite Inbred Maize," *Bio/Technol.,* 7, 581–587 (Jun. 1989).

Shimamoto, K., et al., "Fertile Transgenic Rice Plants Regenerated from Transformed Protoplasts," *Nature,* 338, 274–278 (1989).

Shotwell, M. A., et al., "The Biochemistry of Plants—A Comprehensive Treatise," In: *The Biochemistry of Plants,* vol. 15, Marcus, A., (ed.), Academic Press, Inc., San Diego, pp. 297–345 (1989).

Smith, R., et al., "Shoot apex explant for transformation," *Plant Physiol.,* 86, p. 108, Abstract No. 646 (1988).

Soberon, X., et al., "Construction and Characterization of New Cloning Vehicles, IV. Deletion Derivatives of pBR322 and pBR325," *Gene,* 9, 287–305 (1980).

Songstad, D. D., et al., "Transient Expression of GUS and Anthocyanin Constructs in Intact Maize Immature Embryos Following Electroporation," *Plant Cell Tissue and Organ Culture,* 33, 195–201 (1993).

Spencer, T. M. et al., "Fertile Transgenic Maize," Abstracts, 7th Annual Meeting, Mid Atlantic Plant Mol. Biol. Soc., p. 30 (1990).

Spencer, et al., "Bialaphos Selection of Stable Transformations from Maize Cell Culture," *Theor. Appl. Genet.,* 79, 625–631 (May 1990).

Spencer, T. M., et al., "Segregation of Transgenes in Maize," *Plant Mol. Biol.,* 18, 201–210 (1992).

Spencer, T.M., et al., "Selection of Stable Transformants from Maize Suspension Cultures using the Herbicide Bialaphos," Poster presentation, FASEB Plant Gene Expression Conference, Copper Mountain, Colorado (Aug. 8 1989).

Sprauge et al., "Corn Breeding," In: *Corn and Corn Improvement,* Sprauge, G. F., (ed.), American Society of Agronomy, Inc, Madison, Wi, pp. 305, 320–323 (1977).

Steimel, D., "Corn Breeders Stalk Perfect Hybrid," *Rockford Register Star,* (Aug. 6, 1990).

Steimel, D., "New Gun Will Custom–Design Corn: Breeding Technique Expected by End of '90's Will Let Crop Grow Without Pesticides or Much Water," (Apr. 1990).

Sugiyama, M., et al., "Use of the Tyrosinase Gene from Streptomyces to Probe Promoter Sequences for *Escherichia coli,"* *Plasmid,* 23, 237–241 (1990).

Suttie, J., et al., "Use of Different Selection Agents to Produce Maize Transformants of an Elite Geneotype Using Microprojectile Bombardment," Program and Abstracts, Int. Soc. Plant Mol. Biol., 3rd Int. Cong., Abstract No. 426 (Oct. 6–11, 1991).

Tarczynski, M. C., et al., "Expression of a Bacterial mtlD Gene in Transgenic Tobacco Leads to Production and Accumulation of Mannitol," *Proc. Nat. Acad. Sci. USA,* 89, 2600–2604 (1992).

Tarczynski, M. C., et al., "Stress Protection of Transgenic Tobacco by Production of the Osmolyte Mannitol," *Science,* 259, 508–510 (1993).

Thompson, C., et al., "Characterization of the Herbicide–Resistance Gene bar from *Streptomyces hygroscopicus,*" *EMBO J.,* 6, 2519–2523 (1987).

Tomes, D. "Status of Corn Transformation," 26th Annual Corn Breeders School, Meeting Proceedings, U. Ilinois, p. 7–8 (Feb. 26–27 1990).

Tomes, D. T., et al., "Transgenic Tobacco Plants and their Progeny Derived by Microprojectile Bombardment of Tobacco Leaves," *Plant Mol. Biol.,* 14, 261–268 (Feb. 1990).

Twell, D., et al., "Transient Expression of Chimeric Genes Delivererd into Pollen by Microprojectile Bombardment," *Plant Physiol.,* 91, 1271–1274 (1989).

Ulian, E., et al., "Transformation of Plants via the Shoot Apex," *In Vitro Cell. Dev. Biol.,* 9, 951–954 (1988).

Usami, S., et al., "Absence in Monocotyledonous Plants of the Diffusible Plant Factors including T–DNA Circularization and vir Gene Expression in Agrobacterium," *Mol. Gen. Genet.,* 209, 221–226 (1987).

Vain, P., et al., "Osmotic Pretreament Enhances Particle Bombardment–Mediated Transient Stable Transformation of Maize," *Plant Cell Rep.,* 12, 84–88 (1993).

Vasil, I. K., "Transgenic Cereals Becoming a Reality," *Bio/Technol.,* 8, 797 (Sep. 1990).

Vasil, I. K., et al., "Culture of Protoplasts Isolated from Embryogenic Cell Suspension Cultures of Sugarcane and Maize," *IAPTC Abstracts,* p. 443 (1986).

Vasil, V., et al., "Isolation and Maintenance of Embryogenic Cell Suspension Cultures of Gramineae," In: *Cell Culture and Somatic Cell Genetics of Plants,* vol. I, Academic Press, pp. 152–158 (1984).

Vasil, V., et al., "Plant Regeneration from Friable Embryonic Callus and Cell Suspension Cultures of Zea mays L.," *J. Plant Physiol.,* 124, 399–408 (1986).

Walbot, V., et al., "Molecular genetics of corn," In: *Corn and Corn Improvement,* 3rd edition, Sprauge, G. F., et al., (eds.), American Soc. Agronomy, Madison, WI, pp. 389–430 (1988).

Waldron, C., et al., "Resistance to Hygromycin B," *Plant Mol. Biol.,* 5, 103–108 (1985).

Walters, D. A., et al., "Transformation and Inheritance of Hygromycin Phosphotransferase Gene in Maize Plants," *Plant Molecular Biol.,* 18, 189–200 (1992).

Wan, Y., et al., "Generation of Large Numbers of Independently Transformed Fertile Barley Plants," *Plant Physiol.,* 104, 37–48 (1994).

Wan, Y., et al., "Maize Transformation and Regeneration of Transgenic Plants by Microprojectile Bombardment of Type I Callus," Abstracts, 35th Annual Maize Genetics Conference, p. 5 (Mar. 18–21, 1993).

Wang, Y., et al., "Characterization of cis–Acting Elements Regulating Transcription from the Promoter of a Constitutively Active Rice Actin Gene," *Mol. Cell. Biol.,* 12, 3399–3406 (1992).

Wang, Y., et al., "Transient Expression of Foreign Genes in Rice, Wheat and Soybean Cells Following Particle Bombardment," *Plant Mol. Biol.,* 11, 433–439 (1988).

Weising, K., et al., "Foreign Genes in Plants: Transfer, Structure, Expression and Applications," *Ann. Rev. Genet.,* 22, 421–478 (1988).

White, J., et al., "A Cassette Containing the bar Gene of *Streptomyces hygroscopicus:* a Selectable Marker for Plant Transformation," *Nuc. Acid. Res.,* 18, 1062 (1989).

Whitely, H.R., et al., The Molecular Biology of Parasporal Crystal Body Formation in *Bacillus thuringienesis, Ann. Rev. Microbiol.,* 40, 549–576 (1986).

Wong, E. Y. et al., "*Arabidopsis thaliana* Small Subunit Leader and Transit Peptide Enhance the Expression of *Bacillus thuringiensis* Proteins in Transgenic Plants," *Plant Mol. Biol.,* 20, 81–93 (1992).

Xue, Q., et al., "Genotypic Variation in Osmotic Adjustment Among Closely Related Wheat Lines," Agronomy Abstracts, p. 78 (1995).

Yang, H., et al. "Production of Kanamycin Resistant Rice Tissues Following DNA Uptake into Protoplasts," *Plant Cell Rep.,* 7, 421 (1988).

Yanisch–Perron, C., et al., "Improved M13 Phage Vectors and Host Strains: Nucleotide Sequences of the M13mp18 and pUC19 Vectors," *Gene,* 33, 103–119 (1985).

Yugari, Y., et al., "Coordinated End–Product Inhibition in Lysine Synthesis in *Escherichia coli,*" *Biochem. Biophys. Acta,* 62, 612–614 (1962).

Abe, K., et al., "Molecular Cloning of a Cysteine Proteinase Inhibitor of Rice (Oryzacystatin)", *The Journal of Biological Chemistry,* 262, 16793–16797 (Dec. 15, 1987).

Al–Feel, W., et al., "Cloning of the Yeast FAS3 Gene and Primary Structure of Yeast Acetyl–CoA Carboxylase", *Proc. Natl. Acad. Sci. USA,* 89, 4534–4538 (May 1992).

Anderson, J.M., et al., "The Encoded Primary Sequence of a Rice Seed ADP–glucose Pyrophosphorylase Subunit and Its Homology to the Bacterial Enzyme", *The Journal of Biological Chemistry,* 264, 12238–12242 (Jul. 25, 1989).

Arondel, V., et al., "Map–Based Cloning of a Gene Controlling Omega–3 Fatty Acid Desaturation in Arabidopsis", *Science,* 258, 1353–1355 (Nov. 20, 1992).

Bagga, S., et al., "Accumulation of 15–kilodalton Zein in Novel Protein Bodies in Transgenic Tobacco", *Plant Physiol.,* 107, 13–23 (1995).

Bartley, G.E., et al., "Molecular Cloning and Expression in Photosynthetic Bacteria of a Soybean cDNA Coding for Phytoene Desaturase, an Enzyme of the Carotenoid Biosynthesis Pathway", *Proc. Natl. Acad. Sci. USA,* 88, 6532–6536 (Aug. 1991).

Bol, J.F., et al., "Plant Pathogenesis–Related Proteins Induced by Virus Infection", *Annu. Rev. Phytopathol.,* 28, 113–138 (1990).

Bowler, C., et al., "Superoxide Dismutase and Stress Tolerance", *Annu. Rev. Plant Physiol. Plant Mol. Biol.,* 43, 83–116 (1992).

Castillo, A.M., et al., "Rapid Production of Fertile Transgenic Plants of Rye (*Secale cereale* L.)", *Bio/Technology,* 12, 1366–1371 (Dec. 1994).

Christou, P., et al., "Production of Transgenic Rice (*Oryza sativa* L.) Plants from Agronomically Important Indica and Japonica Varieties via Electric Discharge Particle Acceleration of Exogenous DNA into Immature Zygotic Embryos", *Bio/technology,* 9, 957–962 (Oct. 1991).

Chui, C.–F., et al., "A New Methionine–Rich Seed Storage Protein from Maize", *Plant Physiol.,* 107, 291 (1995).

Depicker, A.G., et al., "A Negative Selection Scheme for Tobacco Protoplast–Derived Cells Expressing the T–DNA Gene 2", *Plant Cell Reports,* 7, 63–66 (1988).

Domoney, C., et al., "Cloning and Characterization of Complementary DNA for Convicilin, a Major Seed Storage Protein in *Pisum sativum* L.", *Planta,* 159, 446–453 (1983).

Dröge–Laser, W., et al., "The Metabolites of the Herbicide L–Phosphinothricin (Glufosinate)", *Plant Physiol.,* 105, 159–166 (1994).

Dunn, G.M., et al., "Inheritance of Cyclic Hydroxamates in *Zea mays* L.", *Can. J. Plant Sci.,* 61, 583–593 (Jul. 1981).

Fisher, D.K., et al., "Starch Branching Enzyme II from Maize Endosperm", *Plant Physiol.,* 102, 1045–1046 (1993).

Frame, B.R., et al., "Production of Fertile Transgenic Maize Plants by Silicon Carbide Whisker–Mediated Transformation", *The Plant Journal,* 6, 941–948 (1994).

Gepts, P., et al., "Enhanced Available Methionine Concentration Associated with Higher Phaseolin Levels in Common Bean Seeds", *Theor. Appl. Genet.,* 69, 47–53 (1984).

Guerrero, F.D., et al., "Turgor–Responsive Gene Transcription and RNA Levels Increase Rapidly When Pea Shoots are Wilted. Sequence and Expression of Three Inducible Genes", *Plant Mol. Biol.,* 15, 11–26 (1990).

Gupta, A.S., et al., "Increased Resistance to Oxidative Stress in Transgenic Plants that Overexpress Chloroplastic Cu/Zn Superoxide Dismutase", *Proc. Natl. Acad. Sci. USA,* 90, 1629–1633 (Feb. 1993).

Häger, K.–P., et al., "Evolution of Seed Storage Protein Genes: Legumin Genes of *Ginkgo biloba*", *Journal of Molecular Evolution,* 41, 457–466 (1995).

Häger, K.–P., et al., "Seed Storage Proteins of Cupressaceae Are Homologous to Legumins from Angiosperms: Molecular Characterization of cDNAs from Incense Cedar (*Calocedrus decurrens* [Torr.] Florin)", *Plant Science,* 116, 85–96 (May 1996).

Hartman, C.L., et al., "Herbicide Resistant Turfgrass (*Agrostis palustris* Huds.) by Biolistic Transformation", *Bio/Technology,* 12, 919–923 (Sep. 1994).

Hu, N.–T., et al., "Primary Structure of a Genomic Zein Sequence of Maize", *The EMBO Journal,* 1, 1337–1342 (1982).

Jähne, A., et al., "Regeneration of Transgenic, Microspore–Derived, Fertile Barley", *Theor. Appl. Genet.,* 89, 525–533 (1994).

Jaworski, J.G., et al., "A Cerulenin Insensitive Short Chain 3–Ketoacyl–Acyl Carrier Protein Synthase in *Spinacia oleracea* Leaves", *Plant Physiol.,* 90, 41–44 (1989).

Josefsson, L.G., et al., "Structure of a Gene Encoding the 1.7 S Storage Protein, Napin, from *Brassica napus*", *The Journal of Biological Chemistry,* 262, 12196–12201 (Sep. 5, 1987).

Kaasen, I., et al., "Molecular Cloning and Physical Mapping of the otsBA Genes, Which Encode the Osmoregulatory Trehalose Pathway of *Escherichia coli:* Evidence that Transcription is Activated by KatF (AppR)", *Journal of Bacteriology,* 174, 889–898 (Feb. 1992).

Kim, C.S., et al., "Improvement of Nutritional Value and Functional Properties of Soybean Glycinin by Protein Engineering", *Protein Engineering,* 3, 725–731 (1990).

Knight, M.R., et al., "Transgenic Plant Aequorin Reports the Effects of Touch and Cold–Shock and Elicitors on Cytoplasmic Calcium", *Nature,* 352, 524–526 (Aug. 8, 1991).

Kogami, H., et al., "Molecular and Physiological Evaluation of Transgenic Tobacco Plants Expressing a Maize Phosphoenolpyruvate Carboxylase Gene Under the Control of the Cauliflower Mosaic Virus 35S Promoter", *Biol. Abstr.,* 98, Abstract No. 147991, p. AB–596 (1994).

Kohno–Murase, J., et al., "Improvement in the Quality of Seed Storage Protein by Transformation of *Brassica napus* with an Antisense Gene for Cruciferin", *Theor. Appl. Genet.,* 91, 627–631 (1995).

Kononowicz, H., et al., "Subdomains of the Octopine Synthase Upstream Activating Element Direct Cell–Specific Expression in Transgenic Tobacco Plants", *The Plant Cell,* 4, 17–27 (Jan. 1992).

Lamppa, G., et al., "Analysis of Two Linked Genes Coding for the Acyl Carrier Protein (ACP) from *Arabidopsis thaliana* (Columbia)", *Plant Molecular Biology,* 16, 469–474 (1991).

Larkins, B.A., et al., "Modification of Maize–Seed Protein Quality", *Am. J. Clin. Nutr.,* 58, 264S–269S (1993).

Malan, C., et al., "Correlation between CuZn Superoxide Dismutase and Glutathione Reductase, and Environmental and Xenobiotic Stress Tolerance in Maize Inbreds", *Plant Science,* 69, 157–166 (1990).

Marks, M.D., et al., "Nucleotide Sequence Analysis of Zein mRNAs from Maize Endosperm", *The Journal of Biological Chemistry,* 260, 16451–16459 (Dec. 25, 1985).

Matthews, B.F., et al., "Nutritional Improvement of the Aspartate Family of Amino Acids in Edible Crop Plants", *Amino Acids,* 4, 21–34 (1993).

Mehta, A., et al., "A Step Towards Developing Transgenic Plants With High Nutritional Quality", *Proc. Indian Natl. Sci. Acad.,* B60, 375–380 (1994).

Montoliu, L., et al., "A Tandem of α–Tubulin Genes Preferentially Expressed in Radicular Tissues from *Zea mays*", *Plant Molecular Biology,* 14, 1–15 (1989).

Mundy, J., et al., "Selective Expression of a Probable Amylase/Protease Inhibitor in Barley Aleurone Cells: Comparison to the Barley Amylase/Subtilisin Inhibitor", *Planta,* 169, 51–63 (1986).

Nishida, I., et al., "The Gene and the RNA for the Precursor to the Plastid–Located Glycerol–3–phosphate Acyltransferase of *Arabidopsis thaliana*", *Plant Molecular Biology,* 21, 267–277 (1993).

O'Reilly, D.R., et al., "A Baculovirus Blocks Insect Molting by Producing Ecdysteroid UDP–Glucosyl Transferase", *Science,* 245, 1110–1112 (Sep. 8, 1989).

Pioneer Hi–Bred International, Inc., Application Under 7 C.F.R. 340, Release of Genetically Engineered Corn Plants, Permit No. 92–212–01, CBI–Deleted, p. 11 (Nov. 16, 1992).

Rice, J.A., et al., "Expression of Synthetic High Lysine Seed Storage Proteins can Significantly Increase the Accumulated Levels of Lysine in Mature Seeds of Transgenic Crop Plants", *Journal of Cellular Biochemistry,* 18 part A, Abstract No. X1–329, p. 107 (1994).

Shorrosh, B.S., et al., "Molecular Cloning, Characterization, and Elicitation of Acetyl–CoA Carboxylase from Alfalfa", *Proc. Natl. Acad. Sci. USA,* 91, 4323–4327 (May 1994).

Shotwell, M.A., et al., "Analysis of Seed Storage Protein Genes of Oats", *The Journal of Biological Chemistry,* 265, 9652–9658 (Jun. 15, 1990).

Smith, I.K., et al., "Properties and Functions of Glutathione Reductase in Plants", *Physiol. Plant.,* 77, 449–456 (1989).

Stalker, D.M., et al., "Herbicide Resistance in Transgenic Plants Expressing a Bacterial Detoxification Gene", *Science,* 242, 419–422 (Oct. 21, 1988).

Stark, D.M., et al., "Regulation of the Amount of Starch in Plant Tissues by ADP Glucose Pyrophosphorylase", *Science,* 258, 287–291 (Oct. 9, 1992).

Stiefel, V., et al., "Expression of a Maize Cell Wall Hydroxyproline–Rich Glycoprotein Gene in Early Leaf and Root Vascular Differentiation", *The Plant Cell*, 2, 785–793 (Aug. 1990).

Stougaard, J., "Substrate–Dependent Negative Selection in Plants Using a Bacterial Cytosine Deaminase Gene", *The Plant Journal*, 3, 755–761 (1993).

Vernon, D.M., et al., "A Novel Methyl Transferase Induced by Osmotic Stress in the Facultative Halophyte *Mesembryanthemum crystallinum*", *The EMBO Journal*, 11, 2077–2085 (1992).

Viotti, A., et al., "Each Zein Gene Class Can Produce Polypeptides of Different Sizes", *The EMBO Journal*, 4, 1103–1110 (1985).

Weeks, J.T., et al., "Rapid Production of Multiple Independent Lines of Fertile Transgenic Wheat (*Triticum aestivum*)", *Plant Physiol.*, 102, 1077–1084 (1993).

Werr, W., et al., "Structure of the Sucrose Synthase Gene on Chromosome 9 of *Zea mays* L.", *The EMBO Journal*, 4, 1373–1380 (1985).

Wolter, F.P., et al., "Chilling Sensitivity of *Arabidopsis thaliana* with Genetically Engineered Membrane Lipids", *The EMBO Journal*, 11, 4685–4692 (1992).

Xiang, C., et al., "The Anti–nptII Gene—A Potential Negative Selectable Marker for Plants", *Plant Physiol.*, 102, 287–293 (1993).

Yang, N.–S., et al., "Maize Sucrose Synthase–1 Promoter Directs Phloem Cell–Specific Expression of Gus Gene in Transgenic Tobacco Plants", *Proc. Natl. Acad. Sci. USA*, 87, 4144–4148 (Jun. 1990).

Yenofsky, R.L., et al., "Isolation and Characterization of a Soybean (*Glycine max*) Lipoxygenase–3 Gene", *Mol. Gen. Genet.*, 211, 215–222 (1988).

```
zmASA2  MESLAAITSV------------------------------F--------APSRVAVPAARALVRAGIVPTRRISS-RSGTSGVKCSAAVIPQA                                              54
ASA2    MSAVSISAVKSDFFIVEAIAVTHHRTPHPPHFPSLRFPLSLKSPPATSLNLVAGSKLLHFSRRL-PSIKCSY--TPSLDLS-------EEQF          80
ASA1    MS--------------------------------------SSMN-VAIMQALITFSRRLLPSVASRYLSSSSVTVTGYSGRSSAY                  45 zmASA2  SPVISRSZAAAKAAFEDKRRFFEAAARGSGKGNLVFMMECIVSDHLITPVLAYRCLVPEINVDAPSTLFESVEQGPQQTTNMGRYSMGAH              144
ASA2    T-KF-----------KK--ASEKGNLVPLFRCVFSDHITPILAYRCLMEDDRDAPSRLFESVEPGSQ-SSNIGRYSVGFAQ                      149
ASA1    APSFRSIKCVSVSPEASIVSDIKKLADASKSINLIPIYRCIFSDQIIPVLAYRCLVEEDREAPSTLFESVEPGSQ-MSSVGRYSVGAQ                134 zmASA2  PVMEIVAKDHKVTIMDHPKSQVTEQVVLDMQIPRIMVEGWHPQQ--IDELPESFSGGMVGFFSMDIVRYVEKKLPFSSAPQDIRNLPD                 232
ASA2    PTIEIVAKGNVVTMDHFASLRTEEEVLDPMVPQKIMEEWNPQG--IDELPEAFOGGMVGYFSYDIVRAVEKKLPFSNAPEDIRSLPD                 237
ASA1    PAMEIVAKEHNKVIVMDHNETMIEEFVEDRMEIPRKLSEKVNPDQLVQDLPDAFCGGMVGFFSMDIVRYVEKRLPFSKAPFDIRNLPD                224 zmASA2  VHIGLVLDMLVEDNVEKKVVTIHWMMERHASVEFAYQDGFSRSRLNMLSKVHNSNVPTLSPGFVKLHIRKFGTPLNKSTMISDEXKNAVL              322
ASA2    VNLGLVDLMIVEDLAVEKKAYMIHWRIDKFSRSVEEENFRBGWNRFESLTSRIQDQKPKMPTGFTIKRTQLFGPKLFKSTMISEAVKEAVV             327
ASA1    MHLGLVLDLVVFDHVEKKAYVIHWIRLDCSLPYEKAYSNGWQHLENEVAKIHDIHEPPKLAAGNMLQTROFGPSLDNSMVTCEEKEAVV               314 zmASA2  QAKEHIMVAGEIFQIVLSQRFERRTVANFEVYRALRTVNPSPAMAYVQARGCVLVASSPEILIRVSKCKTINRPLAGIVRRGKITEKDQM              412
ASA2    FAKEHII AGEIFQIVLSQRFERRTFADFHEIYRALRTVNPSPAMAYLQVRGCIIVASSPEILLRSKNRKDTINRPLAGIVFRGKITPKEDIM           417
ASA1    KAKEHII AGEIFQIVLSQRFERRTFADPFEVYRALRVVNPSPAMYGLQARGCILVASSPEILLTVKVKQNKIVNRPLAGTSKRGRENEVEDKR          404 zmASA2  QEQQLLSDEKQCAEHIMLMVLDLGRNDVGRVSKPGGSSVAVEKLI-IERYSHAMHITSSTVSGQLDHLQSMDALRAALPAGIVSGAPKVKAME            501
ASA2    LEKELLSDEKQCAEHIMLMVLDLGRNDVGRVSKPG--SVEMKKLKDLEWSEHAMHIISSIVVGEILDHLISMDALRAVRAVLPAGIVSGAPKVKAME        506
ASA1    LEKELLFNEKQCAEHIMLMVLDLGRNDVGRVSKPG--SVAVEKIMNIERYSHAMHIISSTIVIGELLQDGLTQMDVIRAALPGIVSGAPKVKAME          493 zmASA2  LIDKLEVIRRGPYSGGLGGISFDGMQIALSLRTTIVFSTAPSHNIMVSYKDAIRRRFMAHLQAGAGIVADSSPDEQRECENKAAALAR                591
ASA2    LIDELEVIRRGPYSGGFGGISFNGMDIALALRIMVFFINIRVDLLYSYKHPQRRREWIAHIQAGAGIVADSNPDEHRECENKAAALAR                596
ASA1    LIDELEPIRRGPYSGGFQGVSFTGDMIALSLRRTIVFPIPACQVNIMVSKDANKRREMAYLQAGAGVADSDPQDEHCEQQNKAAGLAR                583 zmASA2  AIDLAESAFVN---------KE                                                                                604
ASA2    AIDLAESFLEAPEFTTITHINNI                                                                               621
ASA1    AIDLAESAFV----------KK                                                                                595
```

```
TCTAGATATTTTTGTTGGTTGTGTTACTAGCTAGTTTTTTTTAATATGTCTAATCTATCTTTAACAGTCCCCAC        75
CCACCCCACGAGGACACAATTCACTGTGGCTCCATGCTGTGCCACGGCCCAACGGCCACGGTTGGTGGGTGCCTTGG     150
TGTGGGGACCAGACACCGGGATTTTTCGCTGCAAACAACTTGCAGCTAATTTGGCCCCTGTCTTACTGTCTAAGA       225
TACGATAAGGTTACCACGCAAGCGGTCGACAGACTGTACCTCCCTGTGTCCAGTGTCCAAAAATAAGAATTATTT       300
TTTCAAAAATTTCAATGTTAATATCTTCAATGAAGTTTGTTAGGAAATCATATCCACAAACAATATAATAATACA       375
CATTATTACTATATATATTAGTTGATTTATTTCGAGATGAAAGAGTAATATTATTATATTTTTGACAAGTACTG       450
TCTCGTCAGGCTGGCTCCAGCAAGGTTCGGCAAAGCTTCCTGTACCCTAAATATGAGAATCAAACAATCATCTA        525
TGCTCTCTAGCAGCATTTTCTGAACGGTCCTCTAAATTTAGATGACGCTGCTGATTCTTTATATATAGAATTTC       600
TCTAAATGATCCTCTATCTATTGATACATTTAAATAAATCGGTTTAGCAAAACCTAAATATATAATACATTT         675
GAGGGTATTGATAAATACATAGGTAAAAAAATAAAAAAATATCTTTAATATAAATATTACGTATTAGGA             750
GACGTGATTTAAAGGACGCTGTTGGAGAGAAAGTAGATATAAAGGATAAATTTTTTAGAGAAGATAGTAAAGAA        825
AGTATATAAATGATGATAAATTACATTGATTGAGACAGCCTCACCCATCATCATCAGGAAAGCGACGGTGGC          900
TTCTTCCCTCCCCCCTTCACCGTACCGAGACCCCAAACCAAGCGCCTCGCCAGCACCCAGCAGCCCGCATAACTCGT     975
CTCCATTAAAATCGGTTTCTCCTTGGAAATCTGCTGGCGAGTCCCAGGACCCGAATGCCCCACTCTCTTATTACCT     1050
GCTAAATTTGAATTTCCTAATCGGGTTGCAGCTG                                              1084
```

FIG. 5

TTGCCAAACC CTTTTACTGC TGCGAGGTAC CACAGCTTGG TCATTGAGCA        50

AGAAACCTTC CCACATGATG C<u>TTTGGAGGC TACTGCATGG ACTGAAGATG</u>       100

<u>GACTTATCAT GGCTGCTCGC CACAAGAATA CAAACACATC CAGGGTGTCC</u>       150

<u>AATTCCACCC GGAG</u>AGCA                                         168

```
  1 MESLAATSVF APSRVAVPAA RALVRAGTVV PTRRTSSRSG TSGVKCSAAV TPQASPVISR
 61 SAAAAKAAEE DKRRFFEAAA RGSGKGNLVP MWECIVSDHL TPVLAYRCLV PEDNVDAPSF
121 LFESVEQGPQ GTTNVGRYSM VGAHPVMEIV AKDHKVTIMD HEKSQVTEQV VDDPMQIPRT
181 MMEGWHPQQI DELPESFSGG WVGFFSYDTV RYVEKKKLPF SSAPQDDRNL PDVHLGLYDD
241 VLVFDNVEKK VYVIHWVNVD RHASVEEAYQ DGRSRLNMLL SKVHNSNVPT LSPGFVKLHT
301 RKFGTPLNKS TMTSDEYKNA VLQAKEHIMA GDIFQIVLSQ RFERRTYANP FEVYRALRIV
361 NPSPYKAYVQ ARGCVLVASS PEILTRVSKG KIINRPLAGT VRRGKTEKED QMQEQQLLSD
421 EKQCAEHIML VDLGRNDVGK VSKPGGSVKV EKLIIERYSH VMHISSTVSG QLDDHLQSWD
481 ALRAALPVGT VSGAPKVKAM ELIDKLEVTR RGPYSGGLGG ISFDGDMQIA LSLRTIVFST
541 APSHNTMYSY KDADRRREWV AHLQAGAGIV ADSSPDDEQR ECENKAAALA RAIDLAESAF
601 VNKE
```

ANTHRANILATE SYNTHASE GENE AND METHOD OF USE THEREOF FOR CONFERRING TRYPTOPHAN OVERPRODUCTION

CROSS-REFERENCE TO RELATED APPLICATION

This application is a continuation-in-part of U.S. patent application Ser. No. 08/113,561, filed Aug. 25, 1993, pending.

BACKGROUND OF THE INVENTION

Anthranilate synthase (AS) catalyzes the first reaction branching from the aromatic amino acid pathway to the biosynthesis of tryptophan in plants, fungi, and bacteria. The reaction catalyzed by anthranilate synthase is the conversion of chorismate to anthranilate in a glutamine-dependent reaction. In microorganisms, anthranilate synthase is composed of two non-identical subunits: the alpha subunit binds chorismate and eliminates the enolpyruvate side chain, and the beta subunit transfers an amino group from glutamine to the position vacated by the enolpyruvate moiety.

The next reaction in the synthesis of tryptophan is the transfer of the phosphoribosyl moiety of phosphoribosyl pyrophosphate to anthranilate. The indole ring is formed in two steps involving an isomerization converting the ribose group to a ribulose followed by a cyclization reaction to yield indole glycerol phosphate. The final reaction in the pathway is catalyzed by a single enzyme that may contain either one or two subunits. The reaction accomplishes the cleavage of indole glyceraldehyde-3-phosphate and condensation of the indole group with serine (Umbarger, *Ann. Rev. Biochem*, 47, 555 (1978)).

Metabolite flow in the tryptophan pathway in higher plants and microorganisms is apparently regulated through feedback inhibition of anthranilate synthase by tryptophan. Thus, because anthranilate synthase is feedback inhibited by tryptophan, the overproduction of wild-type anthranilate synthase cannot result in tryptophan overproduction.

While anthranilate synthase has been partially purified from crude extracts of cell cultures of higher plants (Hankins et al., *Plant Physiol.*, 57, 101 (1976); Widholm, *Biochim. Biophys. Acta*, 320, 217 (1973)), it was found to be very unstable. In order to further characterize the anthranilate synthase of plants, Niyogi and Fink (*Plant Cell*, 4, 721 (1992)) and Niyogi et al. (*Plant Cell*, 5, 1011 (1993)) employed a molecular approach. They found that Arabidopsis anthranilate synthase alpha subunits are encoded by two closely related, nonallelic genes which are differentially regulated. One of these alpha subunit genes, ASA1, is induced by wounding and bacterial pathogen infiltration, implicating its involvement in a defense response, whereas the other alpha subunit gene, ASA2, is expressed at constitutive basal levels. Both predicted proteins share regions of homology with bacterial and fungal anthranilate synthase proteins, and contain conserved amino acid residues at positions that have been shown to be involved in tryptophan feedback inhibition in bacteria (Caligiuri et al., *J. Biol. Chem.*, 266, 8328 (1991)).

Amino acid analogs of tryptophan or of intermediates in the tryptophan biosynthetic pathway (e.g., 5-methyltryptophan, 4-methyltryptophan, 5-fluorotryptophan, 5-hydroxytryptophan, 7-azatryptophan, 3β-indoleacrylic acid, 3-methylanthranilic acid) have been shown to inhibit the growth of both prokaryotic and eukaryotic cultures. Plant cell cultures can be selected for resistance to these amino acid analogs. For example, cultured tobacco, carrot, potato, corn and *Datura innoxia* cell lines have been selected which are resistant to growth inhibition by 5-methyltryptophan (5-MT), an amino acid analog of tryptophan, due to expression of an altered anthranilate synthase as described below.

Widholm (*Biochem. Biophys. Acta*, 261, 44 (1972)) demonstrated that the tryptophan analogs 5-MT, 4-methyltryptophan, 5-fluorotryptophan and 6-fluorotryptophan cause growth inhibition of tobacco (*Nicotiana tabacum*) and carrot (*Daucus carota*) cell cultures. This inhibition of growth could be reversed by the addition of anthranilic acid, indole, or L-tryptophan. Anthranilate synthase was determined to be very sensitive to these analogs. The tryptophan analogs inhibited cell growth by limiting tryptophan synthesis through the inhibition of anthranilate synthase.

While growth of many cultured tobacco cell lines was inhibited by 5-MT, some tobacco cell lines were resistant to growth inhibitory concentrations of 5-MT (Widholm, *Biochim. Biophys. Acta*, 261, 52 (1972)). The resistant phenotype was stable for at least 60 cell mass doublings even without selection pressure (i.e., without 5-MT). In addition, 5-MT resistant cells were resistant to growth inhibition by other tryptophan analogs. Free tryptophan levels were increased in 5-MT resistant cells about 10-fold over control tissue. Anthranilate synthase in these 5-MT resistant cells was found to be less sensitive to inhibition by tryptophan or 5-MT.

Carrot cell lines that were resistant to growth inhibition by 5-MT were also selected by Widholm (*Biochim. Biophys. Acta*, 279, 48 (1972)). This phenotype was generally stable in the absence of the tryptophan analog for at least 100 cell doublings. 5-MT resistant cells were also resistant to other tryptophan analogs. Free tryptophan concentrations in 5-MT resistant cells were substantially increased to 2170 $\mu$M as compared to 81 $\mu$M (27-fold) for control tissue. Anthranilate synthase was shown to be altered in the 5-MT resistant cells. The enzyme was about 5-fold less sensitive to inhibition by tryptophan or 5-MT than an unaltered anthranilate synthase.

Singh et al. (*Biochem. Genet.*, 13, 357 (1975)) described a mutant in corn, *Zea mays* L., blue fluorescent-1, that possessed increased anthranilate synthase activity which was less sensitive to feedback inhibition. The mutant also accumulated anthranilic acid. In contrast to previous work in tobacco and carrot, however, the altered anthranilate synthase activity did not lead to significant overproduction of tryptophan in mature corn plants or seed.

Hibberd et al. (U.S. Pat. No. 4,581,847, issued Apr. 15, 1986) described 5-MT resistant maize cell lines that contained an anthranilate synthase that was less sensitive to feedback inhibition than wild-type anthranilate synthase. One 5-MT resistant cell line accumulated free tryptophan at levels almost twenty-fold greater than that of non-transformed cell lines.

Carlson et al. (*Physiol. Plant*, 44, 251 (1978)) obtained potato cell (*Solanum tuberosum*) cultures resistant to 5-MT. Anthranilate synthase in these cultures was shown to be less sensitive to inhibition by tryptophan or by 5-MT, although both 5-MT resistant and sensitive forms of the enzyme were present in the cells of the culture. In the selected cell lines, the level of resistant anthranilate synthase was greatly increased relative to the level of the sensitive form. The range of free tryptophan concentrations in selected cultures was from 970 to 1400 $\mu$M compared to control cultures in which the tryptophan concentrations were about 29 $\mu$M.

Widholm (*Plant Cell Cultures: Results and Perspectives,* F. Sala, B. Parisi, R. Cella, O. Ciferri (eds.), Elsevier/North Holland Biomedical Press, Amsterdam, pp. 157–159 (1980)) described plants regenerated from 5-MT resistant *N. tabacum* suspension cultures. While the cultures expressed an anthranilate synthase enzyme that was less sensitive to feedback inhibition by tryptophan and also exhibited an increased level of free tryptophan (approximately 25-fold), the leaves of the regenerated plants did not express the altered form of the enzyme and did not form roots in medium containing 5-MT. The resistance trait was, however, expressed in callus derived from the regenerated plant. Thus it appears to be difficult to obtain expression of the 5-MT resistance phenotype in tobacco plants derived from 5-MT resistant cells selected in culture.

Finally, Ranch et al. (*Plant Physiol.,* 71, 136 (1983)) selected for 5-MT resistance in cell cultures of *Datura innoxia,* a dicot weed, and reported that the resistant cell cultures contained increased tryptophan levels (8 to 30 times higher than the wild type level) and an anthranilate synthase with less sensitivity to tryptophan feedback inhibition. Regenerated plants were also resistant to 5-MT, contained an altered anthranilate synthase, and had a greater concentration of free tryptophan (4 to 44 times) in the leaves than in the leaves of the control plants. In contrast to the studies with *N. tabacum,* where the altered enzyme was not expressed in plants regenerated from resistant cell lines, these results indicated that the amino acid overproduction phenotype could be selected at the cellular level and expressed in whole plants regenerated from the selected cells in *Datura innoxia.*

Although it is possible to select for 5-MT resistance in certain cell cultures and plants, this characteristic does not necessarily correlate with the overproduction of free tryptophan in whole plants. Additionally, plants regenerated from 5-MT resistant lines frequently do not express an altered form of the enzyme. Nor is it predictable that this characteristic will be stable over a period of time and will be passed along as a heritable trait.

Thus, there is a need to increase the tryptophan content of plants and/or provide plants that are resistant to growth inhibitory amounts of tryptophan or an analog thereof.

SUMMARY OF THE INVENTION

The present invention provides an isolated and purified DNA molecule comprising a DNA segment encoding an anthranilate synthase (AS) substantially resistant to inhibition by free L-tryptophan or an amino acid analog of tryptophan such as those discussed hereinbelow. A preferred embodiment of the invention is a plant anthranilate synthase which is substantially resistant to inhibition by free L-tryptophan or an amino acid analog of tryptophan. Another embodiment of the invention is an isolated and purified DNA molecule comprising a DNA segment encoding a maize anthranilate synthase. A DNA molecule of the invention can further comprise an amino terminal plant chloroplast transit peptide sequence operably linked to the anthranilate synthase coding sequence.

Another embodiment of the invention provides a method for conferring tolerance to an amino acid analog of tryptophan and/or altering the tryptophan content of a plant, plant tissue, plant part, or plant cell by introducing and expressing a DNA segment encoding an anthranilate synthase in a plant cell. Also provided is a method of molecularly detecting an anthranilate synthase that is substantially tolerant to inhibition by an amino acid analog of tryptophan comprising identification of a restriction enzyme site polymorphism in the gene encoding the anthranilate synthase. The method comprises mixing DNA isolated from a culture, organism, or a portion of an organism, with an amount of NlaIII restriction endonuclease, and determining whether the restriction endonuclease cleaves the DNA within a portion of the DNA that encodes an anthranilate synthase.

The method of imparting tolerance to an amino acid analog of tryptophan to a plant, plant cell, plant part or plant tissue includes the steps of introducing a preselected DNA segment encoding an anthranilate synthase that is substantially tolerant to inhibition by the tryptophan analog or free L-tryptophan and that is operably linked to a promoter functional in a plant cell, into cells of a susceptible plant. The transformed plant cells are then regenerated to provide a differentiated fertile plant. The promoter can be an inducible or tissue specific promoter. The functional linkage of a promoter to the DNA segment results in an expression cassette. Other transcription or translation regulatory elements, e.g., enhancers or terminators, can also be functionally linked to the DNA segment. Expression of the DNA segment yields an amount of anthranilate synthase effective to render the plant, plant part, plant cell, or plant tissue substantially tolerant to an amount of an amino acid analog of tryptophan or free L-tryptophan that inhibits the growth of a corresponding plant, plant part, plant cell or plant tissue without the DNA segment ("untransformed" material).

Once transformed plant cells exhibiting tolerance are obtained, transgenic plants can then be regenerated therefrom, and evaluated for stability of the inheritance of the resistance or tolerance trait, that is, whether the resistance or tolerance trait is transmitted to progeny. Thus, another embodiment of the invention is a transformed plant that is substantially tolerant to an amino acid analog of tryptophan. The cells of the transformed plant comprise a native anthranilate synthase gene and a DNA segment encoding an exogenous anthranilate synthase. The expression of the exogenous anthranilate synthase in the cells of the plant confer tolerance to the plant to an amount of an amino acid analog of tryptophan or free L-tryptophan that inhibits the activity of the native anthranilate synthase.

The transmission of the resistance or tolerance trait can be evaluated at a molecular level, e.g., Southern or Northern blot analysis, PCR-based methodologies, or the biochemical or immunological detection of anthranilate synthase, or by phenotypic analyses, i.e., whether transformed progeny can grow in the presence of an amount of an amino acid analog of tryptophan or free L-tryptophan that inhibits the growth of an untransformed plant. Also provided is a transformed plant which is substantially tolerant to growth inhibition by an amino acid analog of tryptophan or free L-tryptophan, as well as a seed therefrom.

The invention also provides a method for altering, preferably increasing, the tryptophan content in a plant. The method comprises introducing a DNA segment comprising a gene encoding an anthranilate synthase substantially resistant to inhibition by free L-tryptophan or an amino acid analog of tryptophan, wherein the segment is operably linked to a promoter functional in a plant cell, into the cells of a plant and then expressing the gene in an amount effective to alter the tryptophan content of the plant cell. Thus, another embodiment of the invention is a transformed plant having an altered cellular tryptophan content.

In a preferred embodiment of the invention, transformed cells exhibiting about a 1.1- to 50-fold increase in total tryptophan content are selected for and used to generate transgenic plants, plant parts and seeds exhibiting a substantial increase in tryptophan content. A substantial increase in tryptophan content is determined with respect to the tryptophan content normally present in the untransformed plant, plant part, e.g., leaves or fruit, or seed, and can range from about a 1.1 to a 50-fold increase over that present in the corresponding untransformed plant.

Also provided is a fertile transgenic *Zea mays* plant comprising a DNA segment encoding an anthranilate synthase that is substantially resistant to inhibition by free L-tryptophan or an amino acid analog of tryptophan, operably linked to a promoter. The expression of this DNA segment in the transgenic *Zea mays* plant results in levels of free L-tryptophan in the cells of the transgenic plant that are substantially increased above the levels of free L-tryptophan in the cells of a *Zea mays* plant which only differ from the cells of the transgenic *Zea mays* plant by the absence of the DNA segment. This DNA segment is transmitted through a complete normal sexual cycle of the plant to its progeny and to further generations.

The invention also provides for a method of producing anthranilate synthase in a host cell. The method includes the steps of introducing an expression cassette comprising a DNA segment encoding an anthranilate synthase into a host cell and expressing the DNA segment in the host cell so as to yield anthranilate synthase. An expression cassette preferably includes transcription and translation regulatory elements, e.g., a promoter, functional in host cell, either of eukaryotic or prokaryotic origin. Preferably, the expression cassette is introduced into a prokaryotic cell, such as *E. coli*, or a eukaryotic cell, such as a yeast or insect cell, that is known to be useful for production of recombinant proteins. Recombinantly produced anthranilate synthase can then be used to identify other agents that bind to and inhibit anthranilate synthase.

The present invention also provides an isolated and purified DNA molecule of at least seven nucleotide bases which hybridizes under high stringency conditions to a DNA molecule comprising a DNA segment encoding an anthranilate synthase substantially resistant to inhibition by free L-tryptophan or an amino acid analog of tryptophan, such as a plant anthranilate synthase. Also provided is a hybridization probe comprising an isolated and purified DNA segment of at least seven nucleotide bases, which is detectably labeled or which can bind to a detectable label, which DNA segment hybridizes under high stringency conditions to the non-coding strand of a DNA molecule comprising a DNA segment encoding an anthranilate synthase, such as a plant anthranilate synthase, substantially resistant to inhibition by free L-tryptophan or an amino acid analog of tryptophan, or a maize anthranilate synthase. High stringency conditions are defined as: hybridization at 65° C. for at least 16 hours in 5×SSC, 1× Denhardt's solution, 50 mM Tris-HCl, pH 8, 0.2% SDS, 10 mM EDTA, 0.1 mg/ml salmon sperm DNA, followed by washing twice for 5 minutes in 2×SSC, 0.5% SDS at 25° C., once for 10 minutes in 0.2×SSC, 0.1% SDS at 25° C. and twice for 30 minutes in 0.2×SSC, 0.1% SDS at 56° C.

The present invention also provides a method of introducing an exogenous anthranilate synthase gene into a host cell comprising transforming host cells in vitro with an expression cassette comprising a DNA segment encoding an anthranilate synthase, operably linked to a promoter functional in the host cell, expanding the transformed host cells in vitro, and identifying a transformed host cell which expresses the anthranilate synthase encoded by the DNA segment. A preferred embodiment of the invention is method of introducing an exogenous anthranilate synthase gene into plant cells. A more preferred embodiment of the invention is a method wherein the transformed plant cells can be regenerated into a differentiated dicot or monocot plant.

Another embodiment of the invention is a method of selecting transformed plant cells. The method comprises introducing a preselected DNA segment into a plant cell to yield a transformed plant cell. The DNA segment encodes an anthranilate synthase which is substantially resistant to inhibition by free L-tryptophan or an amino acid analog of tryptophan. The transformed cell is cultured in an amount of free L-tryptophan or an amino acid analog of tryptophan that inhibits the growth of a plant cell which does not contain the preselected DNA segment. A preferred embodiment of the invention is a DNA segment encoding a plant anthranilate synthase. Another preferred embodiment of the invention is a method of selecting transformed plant cells comprising introducing a preselected DNA segment into a plant cell to yield a transformed plant cell. The DNA segment encodes a chloroplast transit peptide operably linked to an anthranilate synthase which is substantially resistant to inhibition by free L-tryptophan or an amino acid analog of tryptophan.

Also provided is an isolated and purified DNA molecule comprising a DNA segment encoding transcription regulatory elements for a plant anthranilate synthase gene.

Further provided is an isolated and purified DNA molecule comprising a DNA segment encoding a beta subunit of an anthranilate synthase.

The term "consists essentially of" as used with respect to the present DNA molecules, sequences or segments is defined to mean that a major portion of the nucleotide sequence encodes an anthranilate synthase, optionally operably linked to a chloroplast transit peptide, and that nucleotide sequences are not present which encode proteins other than an anthranilate synthase, optionally operably linked to a chloroplast transit peptide.

As used herein, "an amino acid analog of tryptophan" is an amino acid analog of an intermediate in the tryptophan biosynthetic pathway or an amino acid analog of tryptophan. These analogs include, but are not limited to, 6-methylanthranilate, 5-methyltryptophan, 4-methyltryptophan, 5-fluorotryptophan, 5-hydroxytryptophan, 7-azatryptophan, 3β-indoleacrylic acid, 3-methylanthranilic acid, and the like.

As used herein, "substantially increased" or "elevated" levels of free L-tryptophan in a plant cell, plant tissue, or plant are levels that are about 1.1 to 50 times, preferably about 2 to 20 times, and more preferably about 3–10 times, the levels found in an untransformed plant cell, plant tissue, or plant, i.e., one where the genome has not been altered by the presence of an exogenous gene. For example, the levels of free L-tryptophan in a transformed plant are compared with those in an untransformed plant. In the alternative, the levels of free L-tryptophan in a homozygous backcross converted inbred transformed plant are compared to the levels in a recurrent inbred plant. A homozygous backcross converted inbred transformed plant is a transformed plant which has been repeatedly crossed to the recurrent inbred parent until the transformed plant is substantially isogenic with the recurrent inbred parent except for the presence of an introduced transgene, and is then is self-pollinated (selfed) at least once.

As used herein, "substantially isogenic" means that the genomic DNA content of a homozygous backcross converted inbred transformed plant is at least about 92%, preferably at least about 98%, and most preferably at least about 99%, identical to the genomic DNA content of a recurrent inbred parent of the transformed plant.

As used herein, a plant cell, plant tissue or plant that is "substantially resistant or tolerant to inhibition by free L-tryptophan or an amino acid analog of tryptophan" is a plant cell, plant tissue, or plant that grows in an amount of tryptophan or an amino acid analog of tryptophan that normally inhibits growth of the untransformed plant cell, plant tissue, or plant, as determined by methodologies known to the art. For example, a homozygous backcross converted inbred plant transformed with a DNA molecule that encodes an anthranilate synthase that is substantially resistant or tolerant to inhibition by free L-tryptophan or an amino acid analog of tryptophan grows in an amount of tryptophan or an amino acid analog of tryptophan that inhibits the growth of the corresponding, i.e., substantially isogenic, recurrent inbred plant.

As used herein, an anthranilate synthase that is "substantially resistant or tolerant to inhibition by free L-tryptophan or an amino acid analog of tryptophan" is an anthranilate synthase that is not inhibited by an amount of free L-tryptophan or an amino acid analog of tryptophan that normally inhibits the corresponding "wild-type" or native anthranilate synthase of the species.

As used herein, "cells of a susceptible plant" are cells which are sensitive to growth inhibition by free L-tryptophan or to an amino acid analog of tryptophan. For example, plant cells from the C28 maize cell line are not susceptible to growth inhibition by 5-methyltryptophan at levels of 5-methyltryptophan that inhibit the growth of many other maize cell lines, such as those obtained from the inbred line H99 or from hybrids such as A188×B73 (Miao et al., *Plant Cell, Tissue and Organ Culture*, 14, 3 (1988)). Thus, C28 cells are not cells of a susceptible plant.

As used herein, an "exogenous" anthranilate synthase is an anthranilate synthase that is encoded by a DNA sequence that has been isolated from a cell, purified, and amplified.

As used herein, a "native" gene means a gene that has not been manipulated in vitro, i.e., has not been isolated, purified, and amplified.

As used herein, "altered" levels of tryptophan in a transformed plant, plant tissue, or plant cell are levels which are greater than the levels found in the corresponding untransformed plant, plant tissue, or plant cells. In the alternative, altered levels of tryptophan in a backcross converted inbred transformed plant are greater than the levels found in the corresponding recurrent inbred plant.

BRIEF DESCRIPTION OF THE FIGURES

FIG. 2 is the nucleotide sequence of the maize anthranilate synthase alpha subunit gene (SEQ ID NO:1).

FIG. 3 is an alignment of the predicted amino acid sequence of maize ASA2 2-1 (SEQ ID NO:2) with those of the Arabidopsis anthranilate synthase ASA1 alpha subunit (SEQ ID NO:3) and the Arabidopsis anthranilate synthase ASA2 alpha subunit (SEQ ID NO:4). Dots indicate residues implicated in feedback regulation in the Salmonella TrpE gene (Caligiuri and Bauerle, *J. Biol. Chem.*, 266, 8328 (1991)). Arrows indicate position of M→K change in C28 allele.

FIG. 5 is the nucleotide sequence of the region immediately upstream of the maize anthranilate synthase alpha subunit coding region (SEQ ID NO:14). The putative ATG for the anthranilate synthase is approximately 130 nucleotides 3' to the 3' most nucleotide in SEQ ID NO:14.

FIG. 6 is the partial nucleotide sequence of the maize anthranilate synthase beta subunit gene (SEQ ID NO:8). The underlined nucleotides are homologous to nucleotides present in the Arabidopsis anthranilate synthase ASB1 beta subunit.

FIG. 7 is the predicted amino acid sequence of the C28 allele of maize anthranilate synthase (SEQ ID NO:16).

DETAILED DESCRIPTION OF THE INVENTION

Figure 1:
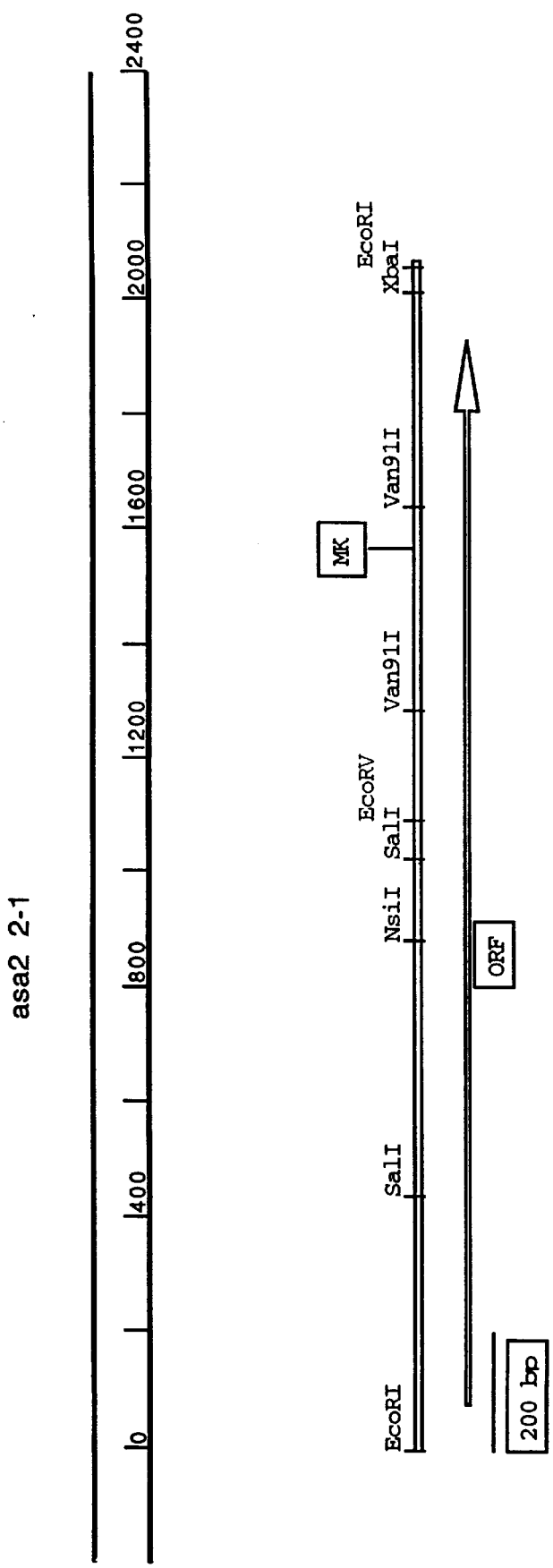
FIG. 1 is a schematic diagram of clone pASA2 2-1.

The present invention provides a DNA molecule encoding an anthranilate synthase substantially resistant to inhibition by free L-tryptophan or an amino acid analog of tryptophan. Also provided are methods for conferring tolerance to an amino acid analog of tryptophan and/or altering the tryptophan content of plant tissues and cells by introducing and expressing an anthranilate synthase gene in the plant cells. Methods and compositions are provided for producing callus cultures, plant tissues, plants and seeds that are tolerant and/or resistant to levels of an amino acid analog of tryptophan or free L-tryptophan that normally inhibit growth. Such plants and seeds genetically can transmit this trait to their progeny.

Methods and compositions are also provided for cloning genes associated with resistance to tryptophan feedback inhibition, and producing callus cultures, plant tissues, plants, plant parts and seeds which overproduce tryptophan and sexually transmit this trait to their progeny. Also described are cell culture selection techniques to select for novel genotypes resistant to tryptophan analogs and which also overproduce tryptophan. For example, to produce resistant maize lines, maize cells that are resistant to a tryptophan analog or free L-tryptophan are isolated and characterized, then regenerated into plants which are resistant to growth inhibition by the analog or by free L-tryptophan. The methods provided in the present invention may also be used to produce increased levels of free tryptophan in monocots and other cereal crops including, but not limited to, rice, rye, millet, wheat, barley, sorghum, and oats.

In accord with the present invention, an anthranilate synthase gene that encodes an enzyme that is resistant to inhibition by free L-tryptophan or an amino acid analog of tryptophan, is identified, isolated, and combined with at least a promoter functional in a plant cell to provide a recombinant expression cassette.

The construction of such expression cassettes which may be employed in conjunction with the present invention will be known to those of skill in the art in light of the present disclosure (see, e.g., Sambrook et al., *Molecular Cloning: A Laboratory Manual*, Cold Spring Harbor, N.Y. (1989); Gelvin et al., *Plant Molecular Biology Manual*, (1990)). Preferred constructs will generally include, but are not limited to, a plant promoter such as the CaMV 35S promoter (Odell et al., *Nature*, 313, 810 (1985)), or others such as CaMV 19S (Lawton et al., *Plant Mol. Biol*, 9, 31F (1987)), nos (Ebert et al., *PNAS USA*, 84, 5745 (1987)), Adh (Walker et al., *PNAS USA*, 84, 6624 (1987)), sucrose synthase (Yang et al., *PNAS USA*, 87, 4144 (1990)), α-tubulin, actin (Wang et al., *Mol. Cell. Biol.*, 12, 3399 (1992)), cab (Sullivan et al., *Mol. Gen. Genet.*, 215, 431 (1989)), PEPCase (Hudspeth et al., *Plant Mol. Biol.*, 12, 579 (1989)) or those associated with the R gene complex (Chandler et al., *The Plant Cell*, 1, 1175 (1989)). It is contemplated that other promoters useful in the practice of the invention are known to those of skill in the art.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924, issued Mar. 1, 1994). For example, it is contemplated that vectors for use in accordance with the present invention may be constructed to include the ocs enhancer element. This element was first identified as a 16 bp palindromic enhancer from the octopine synthase (ocs) gene of Agrobacterium (Ellis et al., *EMBO J.*, 6, 3203 (1987)), and is present in at least 10 other promoters (Bouchez et al., *EMBO J.*, 8, 4197 (1989)). It is proposed that the use of an enhancer element, such as the ocs element and particularly multiple copies of the element, will act to increase the level of transcription from adjacent promoters when applied in the context of monocot transformation. Tissue-specific promoters, including but not limited to, root-cell promoters (Conkling et al., *Plant Physiol.*, 93, 1203 (1990)), and tissue-specific enhancers (Fromm et al., *The Plant Cell*, 1, 977 (1989)) are also contemplated to be particularly useful, as are inducible promoters such as ABA- and turgor-inducible promoters, and the like.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation (Joshi, *Nucl. Acid Res.*, 15, 6643 (1987)). The choice of such sequences will be known to those of skill in the art. Sequences that are derived from genes that are highly expressed in plants, and in maize in particular, will be most preferred.

Constructs will also include the gene of interest along with a 3' end DNA sequence that acts as a signal to terminate transcription and allow for the polyadenylation of the resultant mRNA. The most preferred 3' elements are contemplated to be those from the nopaline synthase gene of *Agrobacterium tumefaciens* (Bevan et al., *Nucl. Acid Res.*, 11, 369 (1983)), the terminator for the T7 transcript from the octopine synthase gene of *Agrobacterium tumefaciens*, and the 3' end of the protease inhibitor I or II genes from potato or tomato, although other 3' elements known to those of skill in the art are also contemplated. Regulatory elements such as Adh intron 1 (Callis et al., *Genes Develop.*, 1, 1183 (1987)), sucrose synthase intron (Vasil et al., *Plant Physiol.*, 91, 5175 (1989)) or TMV omega element (Gallie et al., *The Plant Cell*, 1, 301 (1989)) may further be included where desired. Other such regulatory elements useful in the practice of the invention are known to those of skill in the art.

Additionally, expression cassettes may be constructed and employed to provide targeting of the gene product to an intracellular compartment within plant cells or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences may increase the accumulation of gene product.

A particular example of such a use concerns the direction of an anthranilate synthase to a particular organelle, such as the chloroplast rather than to the cytoplasm. This is exemplified by the use of the rbcS (RUBISCO) transit peptide which confers plastid-specific targeting of proteins.

It is contemplated that targeting of the gene product to an intracellular compartment within plant cells may be achieved by direct delivery of a gene to the intracellular compartment. For example, a gene expression cassette encoding a protein the presence of which is desired in the chloroplast, may be directly introduced into the chloroplast genome using the method described in Maliga et al., U.S. Pat. No. 5,451,513, issued Sep. 19, 1995, incorporated herein by reference.

It is also contemplated that it may be useful to target DNA itself within a cell. For example, it may be useful to target introduced DNA to the nucleus as this may increase the frequency of transformation. Within the nucleus itself, it would be useful to target a gene in order to achieve site-specific integration. For example, it would be useful to have a gene introduced through transformation replace an existing gene in the cell.

After constructing an expression cassette containing an anthranilate synthase gene, the cassette can then be introduced into a plant cell. Depending on the type of plant cell, the level of gene expression, and the activity of the enzyme encoded by the gene, introduction of an anthranilate synthase gene into the plant cell can confer tolerance to an amino acid analog of tryptophan, such as 5-methyltryptophan or 6-methylanthranilate, and/or alter the tryptophan content of the plant cell.

Also in accord with the present invention, an anthranilate synthase gene, such as a plant anthranilate synthase gene, that encodes an enzyme that is sensitive to inhibition by free L-tryptophan or an amino acid analog of tryptophan, is identified and isolated. Such a gene can be used to screen recombinant cDNA or genomic libraries derived from cells that are resistant to inhibition by free L-tryptophan or an amino acid analog of tryptophan to isolate anthranilate synthase mutants or to introduce specific mutations into the anthranilate synthase coding region that result in an enzyme that is resistant to inhibition by free L-tryptophan or an amino acid analog of tryptophan. Further, the gene can be combined with a promoter functional in a host cell to provide a recombinant expression cassette. The expression of the gene in the host cell provides amounts of recombinant anthranilate synthase useful for in vitro screening of agents for their efficacy of enzyme inhibition.

In monocots, an exogenously introduced anthranilate synthase gene that encodes an enzyme that is resistant to inhibition by free L-tryptophan or an analog of tryptophan can be expressed at a level effective to render the cells of the plant tissue substantially tolerant to feedback inhibition by free L-tryptophan at an amount of L-tryptophan that normally inhibits a native or endogenous anthranilate synthase. The tissue can also be rendered resistant to growth inhibition by an amino acid analog of tryptophan at an amount of the analog that normally inhibits the growth of a plant cell or tissue or the activity of a native or endogenous anthranilate synthase. A native or endogenous anthranilate synthase is an enzyme that is normally encoded and expressed in the native plant cell prior to transformation. An exogenously introduced anthranilate synthase gene is a gene which has been isolated from a cell and amplified. Exogenous introduction and expression of an anthranilate synthase gene in both monocots and dicots can result in alteration of the tryptophan content and quality of plant tissue and seeds. Exogenous introduction and expression in a host cell, such as a bacteria, can provide a source for isolating a large quantity of the enzyme. Crystallized anthranilate synthase is useful to identify other agents that bind to and inhibit anthranilate synthase. The isolated enzyme could also be used to screen potential agents for efficacy of enzyme inhibition.

Once an anthranilate synthase gene of interest is isolated, an efficient host vector system is necessary to introduce isolated genes or a group of genes into the genome of plant cells. The foreign genes should be expressed in the transformed plant cells and stably transmitted (somatically and sexually) to the next generation of cells produced. The vector should be capable of introducing, maintaining, and expressing a gene in plant cells, from a variety of sources, including but not limited to plants and animals, bacteria, fungi, yeast or virus. Additionally, it should be possible to introduce the vector into a wide variety of monocot and dicot plants. The new gene is passed on to progeny by normal breeding.

Introduction and expression of foreign genes in dicotyledonous (broad-leafed) plants such as tobacco, potato and alfalfa has been shown to be possible using the T-DNA of the tumor-inducing (Ti) plasmid of *Agrobacterium tumefaciens*. Using recombinant DNA techniques and bacterial genetics, a wide variety of foreign DNAs can be inserted into T-DNA in Agrobacterium. Following infection by the bacterium containing the recombinant Ti plasmid, the foreign DNA is inserted into the host plant chromosomes, thus producing a genetically engineered cell and eventually a genetically engineered plant. A second approach is to introduce root-inducing (Ri) plasmids as the gene vectors.

While Agrobacterium appear to infect only dicots, many important crop plants including corn, wheat, rice, barley, oats, sorghum, millet, and rye are monocots and are not known to be susceptible to transformation by Agrobacterium. The Ti plasmid, however, may be manipulated in the future to act as a vector for monocot plants. Additionally, using the Ti plasmid as a model system, it may be possible to artificially construct gene vectors for monocot plants. Ti-plasmids might also be introduced into monocots by artificial methods such as microinjection, or fusion between monocot protoplasts and bacterial spheroplasts containing the T-region which can then be integrated into the plant nuclear DNA.

Transformation of plants with an anthranilate synthase may also be accomplished by introducing a DNA encoding an anthranilate synthase into other nucleic acid molecules that can transfer the inserted DNA into a plant genome, e.g., plant pathogens such as DNA viruses like CaMV or geminiviruses, RNA viruses, and viroids; DNA molecules derived from unstable plant genome components like extrachromosomal DNA elements in organelles (e.g., chloroplasts or mitochondria), or nuclearly encoded controlling elements; DNA molecules from stable plant genome components (e.g., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of plants) or transposons.

DNA containing an anthranilate synthase gene may be delivered into plant cells or tissues directly by microorganisms with infectious plasmids, infectious viruses, the use of liposomes, microinjection by mechanical or laser beam methods, by whole chromosomes or chromosome fragments, electroporation, and microprojectile bombardment.

A. Strategy for Selection of Tryptophan Overproducer Cell Lines

Efficient selection of a desired tryptophan analog resistant, tryptophan overproducer variant using tissue culture techniques requires careful determination of selection conditions. These conditions are optimized to allow growth and accumulation of tryptophan analog resistant, tryptophan overproducer cells in the culture while inhibiting the growth of the bulk of the cell population. The situation is complicated by the fact that the vitality of individual cells in a population can be highly dependent on the vitality of neighboring cells.

Conditions under which cell cultures are exposed to a tryptophan analog are determined by the characteristics of the interaction of the compound with the tissue. Such factors as the degree of toxicity and the rate of inhibition should be considered. The accumulation of the compounds by cells in culture, and the persistence and stability of the compounds, both in the media and in the cells, also need to be considered. Additionally, it is important to determine whether the effects of the compounds can be readily reversed by the addition of tryptophan.

The effects of the analog on culture viability and morphology is carefully evaluated. It is especially important to choose analog exposure conditions which have no impact on plant regeneration capability of cultures. Choice of analog exposure conditions is also influenced by whether the analog kills cells or simply inhibits cell divisions.

The choice of a selection protocol is dependent upon the considerations described above. The protocols briefly described below may be utilized in the selection procedure. For example, to select for cells that are resistant to growth inhibition by tryptophan or an analog thereof, finely divided cells in liquid suspension culture can be exposed to high tryptophan or analog levels for brief periods of time. Surviving cells are then allowed to recover and accumulate and are then reexposed for subsequently longer periods of time. Alternatively, organized partially differentiated cell cultures are grown and subcultured with continuous exposure to initially low levels of free L-tryptophan or an analog thereof. Concentrations are then gradually increased over several subculture intervals. While these protocols can be utilized in a selection procedure, the present invention is not limited to these procedures.

B. Selection and Characterization of Resistant Cell Lines

Selections are carried out until cells or tissue are recovered which are observed to be growing well in the presence of normally inhibitory levels of tryptophan or an analog thereof. These cell "lines" are subcultured several additional times in the presence of tryptophan or the analog to remove non-resistant cells and then characterized. The amount of resistance which has been obtained is determined by comparing the growth of these cell lines with the growth of unselected cells or tissue in the presence of various analog or free L-tryptophan concentrations. Stability of the resistance trait of the cultured cells may be evaluated by simply growing the selected cell lines in the absence of analog or free L-tryptophan for various periods of time and then analyzing growth after re-exposing the tissue to the analog or free L-tryptophan.

The resistant cell lines may also be evaluated using in vitro chemical studies to verify that the site of action of the analog is altered to a form which is less sensitive to inhibition by tryptophan and/or an analog thereof.

C. Plant Regeneration and Production of Seed

Cell lines exhibiting satisfactory levels of resistance to the tryptophan analog or free L-tryptophan are put through a plant regeneration protocol to obtain mature plants and seed expressing the resistance trait. The plant regeneration protocol allows the development of somatic embryos and the subsequent growth of roots and shoots.

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

D. Development of Tryptophan Overproducer Commercial Hybrid Seed

The commercial value of tryptophan overproducer corn is greatest if many different hybrid combinations are available for sale. The farmer typically grows more than one kind of hybrid based on such differences as maturity, standability or other agronomic traits. Additionally, hybrids adapted to one part of the corn belt are not adapted to another part because of differences in such traits as maturity, disease, and insect resistance. Because of this, it is necessary to breed tryptophan overproduction into a large number of parental lines so that many hybrid combinations can be produced.

A conversion process (backcrossing) is carried out by crossing the original overproducer line to normal elite lines and crossing the progeny back to the normal parent. The progeny from this cross will segregate such that some plants carry the gene responsible for overproduction whereas some do not. Plants carrying such genes will be crossed again to the normal parent resulting in progeny which segregate for overproduction and normal production once more. This is repeated until the original normal parent has been converted to an overproducing line, yet possesses all other important attributes as originally found in the normal parent. A separate backcrossing program is implemented for every elite line that is to be converted to tryptophan overproducer line.

Subsequent to the backcrossing, the new overproducer lines and the appropriate combinations of lines which make good commercial hybrids are evaluated for overproduction as well as a battery of important agronomic traits. Overproducer lines and hybrids are produced which are true to type of the original normal lines and hybrids. This requires evaluation under a range of environmental conditions where the lines or hybrids will generally be grown commercially. For production of high tryptophan corn, it may be necessary that both parents of the hybrid seed corn be homozygous for the high tryptophan character. Parental lines of hybrids that perform satisfactorily are increased and used for hybrid production using standard hybrid seed corn production practices.

E. Alternate Methods of Obtaining Variant Plants that Overproduce Tryptophan Any method which can be utilized to improve the quality and quantity of free tryptophan in plants can be utilized. Generally, biosynthesis of amino acids, including tryptophan, are controlled by feedback regulation. The two major types of feedback regulation are feedback (or end product) inhibition and feedback repression. In feedback inhibition, the final metabolite of the pathway inhibits the activity of an enzyme of the pathway. Feedback repression is the inhibition of formation of one or more enzymes in a pathway by an end product or a derivative of the end product. For many amino acid biosynthetic pathways, the amino acid end product first combines with its transfer RNA (tRNA) to cause repression. Feedback regulation may be circumvented by (a) decrease in the concentration of an inhibitory or repressive end product or (b) mutational alteration of the enzyme or enzyme forming system to a condition less sensitive to feedback effects, i.e., mutation to feedback resistance (For a more complete review of this topic, see Demain, *Advan. Biochem. Eng.*, 1, 113–141 (1971)).

Variants are isolated that may possess an enzyme resistant to feedback inhibition and/or feedback repression by using analogs of the amino acid that exert inhibition and/or repression but cannot be used for protein synthesis. Variants may be resistant to the analog due to an alteration in the structure of the feedback-inhibited enzyme (inhibition resistant) whereas others may have an altered enzyme-forming system (repression resistant). Additionally, these variants overproduce the amino acid due to altered control mechanisms. Mutations to both types of resistance (double mutants) in one line may result in a marked increase in amino acid production.

Any alteration or replacement of anthranilate synthase which leads to deregulation of feedback regulation and overproduction of tryptophan in callus culture, tissue culture, seed and regenerated plants may be utilized in the present invention. Anthranilate synthase may be altered or replaced in any plant species; of especially great importance are the agronomic and horticulture crops which are normally deficient or produce low quantities of tryptophan. The alteration of anthranilate synthase may be accomplished by any of a variety of means, including but not limited to the following methods: (1) spontaneous variation and direct mutant selection in tissue cultures; (2) direct or indirect mutagenesis procedures on tissue cultures of all types, seeds and plants; and (3) isolation of genes, manipulation, modification, or synthesis in whole or part of genes using molecular biology, chemical technologies and state-of-the-art procedures and reintroduction of resistance genes into plants.

Thus, tryptophan overproducer plants may be developed using any of the methods described above including, but not limited to, conventional genetic and plant breeding procedures, whole plant genetic and transgenic methods, and somatic hybridization by protoplast fusion.

F. Formation of an Expression Cassette

An expression cassette of the invention can comprise a DNA molecule encoding an anthranilate synthase gene operably linked to a promoter functional in a host cell. The gene can code for an anthranilate synthase that is substantially tolerant and/or resistant to inhibition by free L-tryptophan or an amino acid analog of tryptophan.

1. Isolation and Identification of a Gene Coding, for an Anthranilate Synthase A gene encoding an anthranilate synthase can be identified and isolated by standard methods, as described by Sambrook et al., *Molecular Cloning: A Laboratory Manual*, Cold Spring Harbor, N.Y. (1989). The gene can also be obtained from tryptophan analog-tolerant cell lines such as plant cell lines, prepared as described in U.S. Pat. No. 4,642,411, which is hereby incorporated by reference.

A gene encoding an anthranilate synthase can be identified by screening of a DNA or cDNA library generated from nucleic acid derived from a particular cell type, cell line, primary cells, or tissue. Examples of libraries to identify and isolate a plant anthranilate synthase include, but are not limited to, a cDNA library derived from inbred line B73 (Stratagene, La Jolla, Calif., Cat. #937005, Clontech, Palo Alto, Calif., Cat. # FL1032a, #FL1032b, and FL1032n), genomic library from inbred line Mo17 (Stratagene, Cat. #946102) or genomic library from inbred line B73 (Clontech, Cat. # FL1032d). Screening for DNA fragments that encode all or a portion of the gene encoding an anthranilate synthase can be accomplished by screening plaques from a genomic or cDNA library for hybridization to a probe of an anthranilate synthase gene from other organisms or by screening plaques from a cDNA expression library for binding to antibodies that specifically recognize anthranilate synthase. DNA fragments that hybridize to anthranilate synthase probes from other organisms and/or plaques carrying DNA fragments that are immunoreactive with antibodies to anthranilate synthase can be subcloned into a vector and sequenced and/or used as probes to identify other cDNA or genomic sequences encoding all or a portion of the desired anthranilate synthase gene. Preferred cDNA probes for screening a maize or plant library can be obtained from plasmid clones pDPG600 or pDPG602.

In a preferred version, a maize anthranilate synthase gene is identified and isolated from a 5-methyltryptophan- or 6-methylanthranilate-tolerant plant cell line prepared as described in Examples 1, 3, and 4. A cDNA library can be prepared by oligo dT priming. Plaques containing DNA fragments can be screened with probes or antibodies specific for anthranilate synthase. DNA fragments encoding a portion of an anthranilate synthase gene can be subcloned and sequenced and used as probes to identify a genomic anthranilate synthase gene. DNA fragments encoding a portion of a maize anthranilate synthase can be verified by determining sequence homology with other known anthranilate synthase genes or by hybridization to anthranilate synthase-specific messenger RNA. Once cDNA fragments encoding portions of the 5', middle and 3' ends of a maize anthranilate synthase are obtained, they can be used as probes to identify and clone a complete genomic copy of a maize anthranilate synthase gene from a maize genomic library.

Portions of the genomic copy or copies of an anthranilate synthase gene can be sequenced and the 5' end of the gene identified by standard methods including either DNA sequence homology to other anthranilate synthase genes or by RNAase protection analysis, as described by Sambrook et al., *Molecular Cloning: A Laboratory Manual,* Cold Spring Harbor Press, Cold Spring Harbor, N.Y. (1989). Once portions of the 5' end of the gene are identified, complete copies of the anthranilate synthase gene can be obtained by standard methods, including cloning or polymerase chain reaction (PCR) synthesis using oligonucleotide primers complementary to the DNA sequence at the 5' end of the gene. The presence of an isolated full-length copy of the anthranilate synthase gene can be verified by hybridization, partial sequence analysis, or by expression of a maize anthranilate synthase enzyme. The anthranilate synthase gene cloned from a 5-MT- or 6-MA-resistant cell line can be assessed for tolerance to 5-MT, 6-MA, or other amino acid analogs of tryptophan by standard methods, as described in U.S. Pat. No. 4,581,847, issued Apr. 15, 1986, the disclosure of which is incorporated by reference herein.

Anthranilate synthase genes resistant and/or tolerant to amino acid analogs of tryptophan can be obtained by several methods. The methods include, but are not limited to:
1. spontaneous variation and direct mutant selection in cultures;
2. direct or indirect mutagenesis procedures on tissue cultures of any cell types or tissue, seeds or plants; and
3. mutation of the cloned anthranilate synthase gene by methods such as site specific mutagenesis (Sambrook et al., cited supra), transposon mediated mutagenesis (Berg et al., *Biotechnology,* 1, 417 (1983)), and deletion mutagenesis (Mitra et al., *Molec. Gen. Genetic.,* 215, 294 (1989)).

Mutants can be identified by a change in a functional activity of the enzyme encoded by the gene in the presence of free L-tryptophan or amino acid analogs of tryptophan, or by detecting a change in the DNA sequence using restriction enzyme mapping or DNA sequence analysis.

In a preferred version, a gene encoding a maize anthranilate synthase substantially tolerant to 5-methyltryptophan is isolated from a maize 5-methyltryptophan tolerant cell line. See U.S. Pat. No. 4,581,847, issued Apr. 15, 1986, the disclosure of which is incorporated by reference herein. Briefly, partially differentiated plant cell cultures are grown and subcultured with continuous exposures to low levels of 5-methyltryptophan. 5-methyltryptophan concentrations are then gradually increased over several subculture intervals. Cells or tissues growing in the presence of normally toxic 5-methyltryptophan levels are repeatedly subcultured in the presence of 5-methyltryptophan and characterized. Stability of the 5-methyltryptophan tolerance trait of the cultured cells may be evaluated by growing the selected cell lines in the absence of 5-methyltryptophan for various periods of time and then analyzing growth after exposing the tissue to 5-methyltryptophan.

Cell lines which are tolerant by virtue of having an altered anthranilate synthase enzyme can be selected by identifying cell lines having enzyme activity in the presence of normally toxic, i.e., growth inhibitor, levels of 5-methyltryptophan.

Cell lines with an anthranilate synthase of reduced sensitivity to 5-methyltryptophan inhibition can be used to isolate a 5-methyltryptophan-resistant anthranilate synthase. A DNA library from a cell line tolerant to 5-methyltryptophan can be generated and DNA fragments encoding all or a portion of an anthranilate synthase gene can be identified by hybridization to a cDNA probe encoding a portion of an anthranilate synthase gene. A complete copy of the altered gene can be obtained either by cloning and ligation or by PCR synthesis using appropriate primers. The isolation of the altered gene coding for anthranilate synthase can be confirmed in transformed plant cells by determining whether the anthranilate synthase being expressed retains enzyme activity when exposed to normally toxic levels of 5-methyltryptophan.

2. Promoters

Once an anthranilate synthase gene is obtained and amplified, it is operably combined with a promoter to form an expression cassette.

Most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous genes, that is a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired.

The promoter in an expression cassette of the invention can provide for expression of anthranilate synthase from an anthranilate synthase gene. Preferably, the gene is expressed so as to result in an increase in tolerance of the plant cells to feedback inhibition by free L-tryptophan or to growth inhibition by an amino acid analog of tryptophan or so as to result in an increase in the total tryptophan content of the cells. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the gene with a promoter that provides tissue specific expression or developmentally regulated gene expression in plants.

Specific promoters functional in plant cells include, but are not limited to, the 35S CaMV promoter, rice actin promoter, ubiquitin, and nopaline synthase (NOS) promoter. Currently, a preferred promoter for expression in monocots is the 35S CaMV promoter.

An anthranilate synthase gene can be combined with the promoter by standard methods as described in Sambrook et al., cited supra. Briefly, a plasmid containing a promoter such as the 35S CaMV promoter can be constructed as described in Jefferson, *Plant Molecular Biology Reporter*, 5, 387 (1987) or obtained from Clontech Lab in Palo Alto, Calif. (e.g., pBI121 or pBI221). Typically, these plasmids are constructed to provide for multiple cloning sites having specificity for different restriction enzymes downstream from the promoter. A gene encoding an anthranilate synthase can be subcloned downstream from the promoter using restriction enzymes to ensure that the gene is inserted in proper orientation with respect to the promoter so that the gene can be expressed. In a preferred version, a plant anthranilate synthase is operably linked to a 35S CaMV promoter in a plasmid. In a more preferred embodiment of the invention, a maize anthranilate synthase gene is operably lined to a 35S CaMV promoter in a plasmid. Once an anthranilate synthase gene is operably linked to a promoter, the expression cassette so formed can be subcloned into a plasmid or other vectors.

3. Optional Sequences in the Expression Cassette

The expression cassette can also optionally contain other DNA sequences. The expression cassette can further be comprised of a chloroplast transit peptide encoding DNA sequence operably linked between a promoter and the DNA sequence encoding an anthranilate synthase (for a review of plastid targeting peptides, see Heijne et al., *Eur. J. Biochem.*, 180, 535 (1989); Keegstra et al., *Ann. Rev. Plant Physiol.*

*Plant Mol. Biol.*, 40, 471 (1989)). If the expression cassette is to be introduced into a plant cell, the expression cassette can also contain plant transcriptional termination and polyadenylation signals and translational signals linked to the 3' terminus of a plant anthranilate synthase gene. The expression cassette can also optionally further comprise plasmid DNA.

An exogenous chloroplast transit peptide can be used which is not encoded within a native plant anthranilate synthase gene. A chloroplast transit peptide is typically 40 to 70 amino acids in length and functions post-translationally to direct a protein to the chloroplast. The transit peptide is cleaved either during or just after import into the chloroplast to yield the mature protein. The complete copy of a gene encoding a plant anthranilate synthase may contain a chloroplast transit peptide sequence. In that case, it may not be necessary to combine an exogenously obtained chloroplast transit peptide sequence into the expression cassette.

Exogenous chloroplast transit peptide encoding sequences can be obtained from a variety of plant nuclear genes, so long as the products of the genes are expressed as preproteins comprising an amino terminal transit peptide and transported into chloroplast. Examples of plant gene products known to include such transit peptide sequences include, but are not limited to, the small subunit of ribulose biphosphate carboxylase, ferredoxin, chlorophyll a/b binding protein, chloroplast ribosomal proteins encoded by nuclear genes, certain heatshock proteins, amino acid biosynthetic enzymes such as acetolactate acid synthase, 3-enolpyruvylphosphoshikimate synthase, dihydrodipicolinate synthase, and the like. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon and an amino acid sequence that is recognized by and will function properly in chloroplasts of the host plant. Attention should also be given to the amino acid sequence at the junction between the transit peptide and the anthranilate synthase enzyme where it is cleaved to yield the mature enzyme. Certain conserved amino acid sequences have been identified and may serve as a guideline. Precise fusion of the transit peptide coding sequence with the anthranilate synthase coding sequence may require manipulation of one or both DNA sequences to introduce, for example, a convenient restriction site. This may be accomplished by methods including site-directed mutagenesis, insertion of chemically synthesized oligonucleotide linkers, and the like.

Once obtained, the chloroplast transit peptide sequence can be appropriately linked to the promoter and an anthranilate synthase gene in an expression cassette using standard methods. Briefly, a plasmid containing a promoter functional in plant cells and having multiple cloning sites downstream can be constructed as described in Jefferson, cited supra. The chloroplast transit peptide sequence can be inserted downstream from the promoter using restriction enzymes. An anthranilate synthase gene can then be inserted immediately downstream from and in frame with the 3' terminus of the chloroplast transit peptide sequence so that the chloroplast transit peptide is linked to the amino terminus of the anthranilate synthase. Once formed, the expression cassette can be subcloned into other plasmids or vectors.

When the expression cassette is to be introduced into a plant cell, the expression cassette can also optionally include 3' nontranslated plant regulatory DNA sequences. The 3' nontranslated regulatory DNA sequence preferably includes from about 300 to 1,000 nucleotide base pairs and contains plant transcriptional and translational termination sequences. Examples of 3' nontranslated regulatory DNA sequences functional in plant cells include, but are not limited to, about 500 base pairs of the 3' flanking DNA sequence of the pea ribulose biphosphate carboxylase small subunit E9 gene, the 3' flanking DNA sequence of the octopine synthase gene, and the 3' flanking DNA sequence of the nopaline synthase gene. These 3' nontranslated regulatory sequences can be obtained as described in An, *Methods in Enzymology,* 153, 292 (1987) or are already present in plasmids available from commercial sources such as Clontech, Palo Alto, Calif. The 3' nontranslated regulatory sequences can be operably linked to the 3' terminus of an anthranilate synthase gene by standard methods.

An expression cassette of the invention can also be further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC 119, and pUC120, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the expression cassette, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA582. This binary Ti plasmid vector has been previously characterized by An, cited supra, and is available from Dr. An. This binary Ti vector can be replicated in prokaryotic bacteria such as *E. coli* and Agrobacterium. The Agrobacterium plasmid vectors can be used to transfer the expression cassette to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform plant cells.

G. Method for Screening for Expression of an Anthranilate Synthase Gene

A method for screening for expression of an anthranilate synthase gene is also provided by the invention. Once formed, an expression cassette comprising an anthranilate synthase gene can be subcloned into a known expression vector. The screening method in the invention includes the steps of introducing an expression vector into a host cell and detecting and/or quantitating expression of an anthranilate synthase gene. This method of screening is useful to identify expression cassettes providing for an expression of an anthranilate synthase gene, and expression of an anthranilate synthase in the chloroplast of a transformed plant cell.

Suitable known expression vectors include plasmids that autonomously replicate in prokaryotic and/or eukaryotic cells. Specific examples include plasmids such as pUC, pSK, pGEM, pBS and pSP-derived vectors described above, the pBI121 or pBI221 plasmid constructed as described by Jefferson, cited supra, or a binary Ti plasmid vector such as pG582 as described by An, cited supra, and the like.

An expression cassette of the invention can be subcloned into an expression vector by standard methods. The expression vector can then be introduced into prokaryotic or eukaryotic cells by currently available methods including, but not limited to, protoplast transformation, Agrobacterium-mediated transformation, electroporation, microprojectile bombardment, tungsten whiskers (Coffee et al., U.S. Pat. No. 5,302,523, issued Apr. 12, 1994) and liposomes. The expression vector can be introduced into plant cells such as maize, tobacco, Brassica, Black Mexican sweet corn, and Arabidopsis cells. Plant cells useful for transformation include callus, embryos, meristematic tissue, gametic tissue, or cultured suspension cells.

The vector can also be introduced into prokaryotic cells such as *E. coli* or Agrobacterium. Transformed cells can be selected typically using a selectable marker encoded on the expression vector.

Marker genes are also useful in the present invention. Marker genes are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the maize HPRG (Steifel et al., *The Plant Cell,* 2, 785 (1990)) is preferred as this molecule is well characterized in terms of molecular biology, expression, and protein structure. However, any one of a variety of extensins and/or glycine-rich wall proteins (Keller et al., *EMBO J.,* 8, 1309 (1989)) could be modified by the addition of an antigenic site to create a screenable marker.

Elements of the present disclosure are exemplified in detail through the use of particular marker genes, however in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed monocot.

Possible selectable markers for use in connection with the present invention include, but are not limited to, a neo gene (Potrykus et al., *Mol. Gen. Genet.,* 199, 183 (1985)) which codes for kanamycin resistance and can be selected for using kanamycin, G418, and the like; a bar gene which codes for bialaphos resistance; a gene which encodes an altered EPSP synthase protein (Hinchee et al., *Biotech.,* 6, 915 (1988)) thus conferring glyphosate resistance; a nitrilase gene such as bxn from *Klebsiella ozaenae* which confers resistance to bromoxynil (Stalker et al., *Science,* 242, 419 (1988)); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., *J. Biol. Chem.,* 263, 12500 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. patent application Ser. No. 07/565,844, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.,* 205, 42 (1986); Twell et al., *Plant Physiol.,* 91, 1270 (1989)) causing rapid accumulation of ammonia and cell death. The success of the inventors of the 07/565,844 application in using this selective system in conjunction with monocots was particularly surprising because of the major difficulties which have been reported in transformation of cereals (Potrykus, *Trends Biotech.,* 7, 269 (1989)).

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in *Chromosome Structure and Function,* pp. 263–282 (1988)); a β-lactamase gene (Sutcliffe, *PNAS USA,* 75, 3737 (1978)), which encodes an enzyme for which various chromogenic substrates are known (e.g., PADAC, a chromogenic cephalosporin); a xylE gene (Zukowsky et al., *PNAS USA,* 80, 1101 (1983)) which encodes a catechol dioxygenase that can convert chromogenic catechols; an α-amylase gene (Ikuta et al., *Biotech.,* 8, 241 (1990)); a tyrosinase gene (Katz et al., *J. Gen. Microbiol.,* 129, 2703 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science,* 234, 856 (1986)), which allows for bioluminescence detection; or even an aequorin gene (Prasher et al., *Biochem. Biophys. Res. Comm.,* 126, 1259 (1985)), which may be employed in calcium-sensitive bioluminescence detection, or a green fluorescent protein gene (Niedz et al., *Plant Cell Reports,* 14, 403 (1995)).

The presence of the lux gene in transformed cells may be detected using, for example, X-ray film, scintillation counting, fluorescent spectrophotometry, low-light video cameras, photon-counting cameras, or multiwell luminometry. It is also envisioned that this system may be developed for populational screening for bioluminescence, such as on tissue culture plates, or even for whole plant screening.

Transient expression of an anthranilate synthase gene can be detected and quantitated in the transformed cells. Gene expression can be quantitated by RT-PCR analysis, a quantitative Western blot using antibodies specific for the cloned anthranilate synthase or by detecting enzyme activity in the presence of tryptophan or an amino acid analog of tryptophan. The tissue and subcellular location of the cloned anthranilate synthase can be determined by immunochemical staining methods using antibodies specific for the cloned anthranilate synthase or subcellular fractionation and subsequent biochemical and/or immunological analyses. Sensitivity of the cloned anthranilate synthase to agents can also be assessed. Expression cassettes providing for expression of an anthranilate synthase or anthranilate synthase tolerant to inhibition by an amino acid analog of tryptophan or free L-tryptophan can then be used to transform monocot and/or dicot plant tissue cells and to regenerate transformed plants and seeds.

H. Method of Imparting Tolerance to an Amino Acid Analog of Tryptophan and/or Altering the Tryptophan Content in a Plant Cell or Tissue The invention provides a method of conferring tolerance to tryptophan or an amino acid analog of tryptophan to a plant cell or tissue. The method includes the steps of introducing an expression cassette comprising a DNA sequence coding for an anthranilate synthase wherein the anthranilate synthase is enzymatically active in the presence of concentrations of the analog or free L-tryptophan that inhibit the endogenous or native anthranilate synthase. The DNA sequence is operably linked to a promoter whereby, in the cells of the plant tissue, the sequence is expressed in an amount effective to render the cells of the plant tissue substantially tolerant to tryptophan or an analog thereof For example, an effective amount of gene expression to render the cells of the plant tissue substantially tolerant to 5-MT or 6-MA is an amount that provides for plant cell growth in about 33 to 300 μM 5-MT or 6-MA, preferably about 75–250 μM 5-MT or 6-MA. These are amounts of 5-MT or 6-MA which normally inhibit a native anthranilate synthase. The amounts of other tryptophan analogs effective to render cells of a plant substantially tolerant to the analog can be determined by methods well known in the art.

An expression cassette of the invention can be introduced by methods of transformation especially effective for monocots, including, but not limited to, microprojectile bombardment of immature embryos (U.S. patent application Ser. No. 08/249,458, filed May 26, 1994, incorporated by reference herein; U.S. patent application Ser. No. 08/112, 245, filed Aug. 25, 1993, incorporated by reference herein) or Type II embryogenic callus cells as described by W. J. Gordon-Kamm et al. (*Plant Cell,* 2, 603 (1990)), M. E. Fromm et al. (*Bio/Technology,* 8, 833 (1990)) and D. A. Walters et al. (*Plant Molecular Biology,* 18, 189 (1992)), or by electroporation of type I embryogenic calluses described by D'Halluin et al. (*The Plant Cell,* 4, 1495 (1992)), or by Krzyzek (U.S. Pat. No. 5,384,253, issued Jan. 24, 1995).

Transformed cells can be selected for the presence of a selectable marker gene. Transient expression of an anthranilate synthase gene can be detected in the transgenic embryogenic calli using antibodies specific for the cloned anthranilate synthase, or by RT-PCR analyses. Transformed embryogenic calli can be used to generate transgenic plants that exhibit stable inheritance of the transformed anthranilate synthase gene. Plant cell lines exhibiting satisfactory levels of tolerance to an amino acid analog of tryptophan or free L-tryptophan are put through a plant regeneration protocol to obtain mature plants and seeds expressing the tolerance traits by methods well known in the art (for example, see U.S. patent application Ser. No. 08/112,245; and Laursen et al., *Plant Mol. Biol.,* 24, 51 (1994)). The plant regeneration protocol allows the development of somatic embryos and the subsequent growth of roots and shoots. To determine that the tolerance trait is expressed in differentiated organs of the plant, and not solely in undifferentiated cell culture, regenerated plants can be assayed for the levels of tryptophan present in various portions of the plant relative to regenerated, non-transformed plants.

The transgenic plants produced herein are expected to be useful for a variety of commercial and research purposes. Transgenic plants can be created for use in traditional agriculture to possess traits beneficial to the consumer of the grain harvested from the plant (e.g., improved nutritive content in human food or animal feed). In such uses, the plants are generally grown for the use of their grain in human or animal foods. However, other parts of the plants, including stalks, husks, vegetative parts, and the like, may also have utility, including use as part of animal silage or for ornamental purposes.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from corn cells to cells of other species, e.g., by protoplast fusion.

The regenerated plants are self-pollinated. Pollen obtained from the regenerated plants is crossed to seed-grown plants of agronomically important inbred lines or regenerated plants are self-pollinated. Conversely, pollen from plants of these inbred lines is used to pollinate regenerated plants. The genetics of the trait are then characterized by evaluating the segregation of the trait in the first and later generation progeny.

Regenerated plants are repeatedly crossed to inbred corn plants in order to introgress the exogenously introduced or preselected anthranilate synthase gene into the genome of the inbred corn plants. This process is referred to as backcross conversion. When a sufficient number of crosses to the recurrent inbred parent have been completed in order to produce a product of the backcross conversion process that is substantially isogenic with the recurrent inbred parent except for the presence of the introduced transgene, the plant is self-pollinated at least once in order to produce a homozygous backcross converted inbred containing the preselected transgene. Progeny of these plants are true breeding and tryptophan analog resistance and concentrations of tryptophan in the backcross converted inbreds are compared to the recurrent parent inbred.

Alternatively, seed from transformed monocot plants regenerated from transformed tissue cultures is grown in the field and self-pollinated to generate true breeding plants. Progenies from these plants become true breeding lines which are evaluated for tryptophan amino acid analog tolerance in the field under a range of environmental conditions. Tryptophan amino acid analog tolerance must be sufficient to protect the monocot plants at the maximum delivery rate under field conditions which causes the amino acid analog to be most active. The determination of appropriate concentrations of these agents and methods of application are well known in the art.

In a preferred version, an expression cassette comprised of a maize anthranilate synthase gene isolated from a maize cell line tolerant to 5-MT and linked to the 35S CaMV promoter is introduced into an 5-MT sensitive monocot tissue using biolistic transformation. Transformed calli are selected and used to generate transgenic plants. Transformed calli and transgenic plants can be evaluated for tolerance to 5-MT or 6-MA and for stable inheritance of the tolerance trait.

The invention also provides a method of altering the tryptophan content in a plant cell or tissue. The method include the steps of introducing an expression cassette comprising a DNA sequence coding for an anthranilate synthase that is resistant to inhibition by free L-tryptophan or an amino acid analog of tryptophan, operably linked to a promoter functional in a plant cell into the cells of plant, and expressing the gene in an amount effective to alter the tryptophan content of the plant cell. An alteration in the tryptophan content of a plant cell can include a change in the total tryptophan content over that normally present in that type of plant cell not transformed with the expression cassette. Expression of an anthranilate synthase gene in an effective amount is that amount that may provide a change in the tryptophan content of the cell from about 1.1- to 50-fold over that normally present in the plant cell, and preferably increases the amount of tryptophan of about 2- to 20-fold over the amount of tryptophan normally present in that plant cell.

To provide for expression of the anthranilate synthase gene, the gene can be combined with a promoter that provides for a high level of gene expression in plant cells, such as the 35S CaMV promoter.

An expression cassette as described above can be introduced into either monocots or dicots. An expression cassette can be introduced by standard methods including protoplast transformation, Agrobacterium-mediated transformation, microprojectile bombardment, electroporation, and the like. Transformed cells or tissues can be selected for the presence of a selectable marker gene.

Transient expression of an anthranilate synthase gene can be detected in transformed cells or tissues by immunoreactivity with antibodies specific for anthranilate synthase. Stable expression of an anthranilate synthase can be detected by quantitative Western blots. A change in specific activity of the enzyme in the presence of inhibitory amounts of tryptophan or an analog thereof can be detected by measuring enzyme activity in the transformed cells as described by Widholm, *Biochimica et Biophysica Acta,* 279, 48 (1972). A change in total tryptophan content can also be examined by standard methods as described by Jones et al., *Analyst,* 106, 968 (1981).

Transgenic plants and seeds can be generated from transformed cells and tissues showing a change in tryptophan content or in resistance to a tryptophan analog using standard methods. It is especially preferred that the tryptophan content of the leaves, seeds, or fruits is increased.

I. Method of Introducing and Producing Anthranilate Synthase

The invention also provides a method of introducing and producing anthranilate synthase in a host cell. The method includes the steps of introducing an expression cassette comprised of a gene encoding an anthranilate synthase into a host cell and identifying a cell with the expression cassette and/or a cell expressing the gene. The availability of large amounts of purified enzyme provides for screening of the efficacy of such agents.

An expression cassette can include a promoter that is functional in either a eukaryotic or prokaryotic cell. The expression cassette can be introduced into a prokaryotic cell such as *E. coli*, or a eukaryotic cell such as a plant or yeast. The preferred cell is a prokaryotic cell used routinely in producing recombinant proteins such as *E. coli*. Prokaryotic or eukaryotic transformed cells can be selected by standard methods.

Anthranilate synthase can be isolated from bacterial cells using standard methods, e.g., see Sambrook et al., *Molecular Cloning: A Laboratory Manual*, (1989). The purified anthranilate synthase can then be characterized by standard methods.

J. Commercial Approaches to Tryptophan Extraction from High Tryptophan Maize Seed Fertile, transgenic plants may then be used in a conventional maize breeding program in order to incorporate the introduced DNA into the desired lines or varieties. Methods and references for convergent improvement of corn are given by Hallauer et al., In: *Corn and Corn Improvement*, Sprague et al. (eds.), pp. 463–564 (1988), incorporated herein by reference. Among the approaches that conventional breeding programs employ is a conversion process (backcrossing). Briefly, conversion is performed by crossing the initial transgenic fertile plant to elite inbred lines. The progeny from this cross will segregate such that some of the plants will carry the recombinant DNA whereas some will not. The plants that do not carry the DNA are then crossed again to the elite inbred lines resulting in progeny which segregate once more. This backcrossing process is repeated until the original elite inbred has been converted to a line containing the recombinant DNA, yet possession all important attributes originally found in the parent. Generally, this will require about 6–8 generations. A separate backcrossing program will be generally used for every elite line that is to be converted to a genetically engineered elite line.

Generally, the commercial value of the transformed corn produced herein will be greatest if the recombinant DNA can be incorporated into many different hybrid combinations. A farmer typically grows several hybrids based on differences in maturity, standability, and other agronomic traits. Also, the farmer must select a hybrid based upon his or her geographic location since hybrids adapted to one region are generally not adapted to another because of differences in such traits as maturity, disease, and insect resistance. As such, it is necessary to incorporate the introduced DNA into a large number of parental lines so that many hybrid combinations can be produced containing the desirable DNA.

Corn breeding and the techniques and skills required to transfer genes from one line or variety to another are well known to those skilled in the art. Thus, introducing recombinant DNA into any other line or variety can be accomplished by these breeding procedures.

There are a number of methods that can be used to extract the free tryptophan from high tryptophan maize, however, the more economical of these would likely involve extracting the tryptophan prior to or following standard wet or dry milling processes (Watson, *Corn and Corn Improvements*, G. F. Sprague, ed., Amer. Soc. of Agronomy, Madison, Wis. (1977)). This permits the value of the tryptophan to be added to the value of milled products.

In the wet milling process, one of the initial steps involves treating the kernels with an acidic aqueous solution and allowing a limited amount of lactic acid fermentation to occur. This treatment conditions and softens the kernel and solubilizes many small molecules in the kernel including free amino acids. This acid environment will, however, result in breakdown of most of the solubilized tryptophan. Thus, to obtain significant amounts of tryptophan, it is preferred to extract the tryptophan prior to the acid treatment step. A method that can be used to carry out this pre-extraction process is described below.

Maize seed can be processed in a series of vats at elevated temperatures (approximately 150° F.) in an aqueous environment at basic/neutral pH (pH$\leq$10). Water is added to the corn that has been extracted the longest in the process and flows in a countercurrent manner towards the newly introduced seed. Following several days of extraction, the corn is then transferred to a standard wet milling plant. The liquid from the extraction process can then be filtered to remove solids then treated by standard chemical means, solvent extraction/phase separation, ion exchange chromatography and crystallization, to concentrate and purify the tryptophan. The degree of purification will depend on the type of product desired—feed supplement, chemical feed stock, reagent chemical, etc.

In the dry milling processes, corn kernels are cleaned, brought to 20–22% moisture then milled, pressed, and sorted to give a variety of fractions—hominy feed, flaking, medium and fine grits, meal, and flour. One or more of these fractions can then be extracted with water under neutral to basic conditions at elevated temperature to obtain the tryptophan. Again, the tryptophan can then be concentrated and purified by standard chemical methods including solvent extraction/phase separation, ion exchange chromatography and crystallization.

Tryptophan may also be recovered by other conventional procedures. For example, a method for recovery is represented in U.S. Pat. No. 3,759,790 which is hereby incorporated by reference into the present specification.

EXAMPLE 1

Identification of Recombinant DNA Clones Corresponding to Genes Encoding Maize Anthranilate Synthase Alpha- and Beta-Subunits To obtain clones corresponding to maize genes encoding the alpha-subunit of anthranilate synthase, gene-specific oligonucleotide primers corresponding to the Arabidopsis ASA2 gene sequence (GenBank Accession M92354) were designed to allow for PCR amplification of a region from exons 10 through 11 of this gene in Arabidopsis. Exons 10 and 11 of the alpha subunit of the Arabidopsis anthranilate synthase have been defined by Niyogi and Fink (supra). These primers, designated ASA2-C (AAGAAGATCTAATGCTGGAAAAA, SEQ ID NO:5) and ASA2-D (GATATTGTTGATGTGAGGTGTGA, SEQ ID NO:6), were used in a PCR amplification of Arabidopsis DNA under the following conditions: 0.5 $\mu$g of DNA was used as template in reactions containing 0.5 $\mu$M each of primer ASA2-C and ASA2-D, 200 $\mu$M each dATP, dCTP, dGTP, and dTTP, 1 mM $MgCl_2$, 50 mM KCl, 10 mM Tris-HCl, pH 8.3, and 2.5U Taq DNA polymerase. Thermal cycling conditions were as follows: initial denaturation at 97° C. for 2 minutes; three cycles of 97° C. for 1 minute, 53° C. for 1 minute, and 72° C. for 1 minute; 33 cycles of 94° C. for 1 minute, 53° C. for 1 minute, and 72° C. for 1 minute; and a final extension of 72° C. for 4 minutes. A PCR-generated amplification product of 1037 base pairs was cleaved with Nco1 to yield two fragments of 685 and 352 base pairs, the latter of which corresponds exclusively to exon 11 of Arabidopsis ASA2, from positions 5362 to 5714 of the M92354 sequence. This fragment was gel-purified and used as a radiolabelled probe for screening a cDNA library constructed in the cloning vector LambdaZAP (Stratagene, La Jolla, Calif.) corresponding to mRNAs obtained from maize embryos (inbred line Va26) at 27 days after pollination (Belanger and Kriz, Plant Physiol., 91, 636 (1989)).

Initial screening of the library was performed under low-stringency hybridization conditions (42° C., 6×SSC, 1× Denhardt's solution, 0.1% SDS, 10 μg/ml sonicated calf thymus DNA). Filters were washed in 3×SSC, 0.1% SDS at room temperature, then in 1×SSC, 0.1% SDS, and finally in 1×SSC at 60° C. Subsequent rounds of screening for plaque purification purposes were performed in a similar manner except that a temperature of 48° C. was used for the hybridization step. A total of five putative anthranilate synthase cDNA clones were identified by this screening protocol.

Each of these clones was subjected to a limited amount of nucleotide sequence analysis using vector-specific primers and standard protocols (see, Sambrook et al., supra). Comparison of these nucleotide sequences indicated that four of the clones (pcASA2 1-1, 2-1, 4-1, and 5-3) were identical in sequence and another (pcASA2 3-1) was similar, but not identical, to the others. These results indicated that cDNA clones corresponding to two distinct genes had been obtained by screening the library with a probe derived from the Arabidopsis anthranilate synthase gene sequence. Comparison of the gene sequences of these clones with the sequences of the Arabidopsis anthranilate synthase genes (GenBankM92354 and M92353) revealed similarity between the maize and Arabidopsis sequences.

To obtain genomic clones corresponding to maize anthranilate synthase alpha subunits, a library of DNA fragments generated by partial digestion of nuclear DNA from the maize inbred line B73 was constructed in the lambda cloning vector EMBL3 using standard protocols. This library was screened with a radiolabelled probe consisting of a 351 base pair Van91I fragment obtained from the clone pcASA2 2-1 (FIG. 1). Hybridization was performed overnight at 68° C. in a solution of 6×SSC, 0.1% SDS, 1× Denhardt's solution, and 10 μg/ml sonicated salmon sperm DNA. Washing of filters was performed at 68° C. in 2×SSC, 0.1% SDS. A single lambda clone was selected for analysis. DNA from this clone was subjected to digestion with a variety of restriction enzymes followed by Southern blot analysis in which a 440 base pair SalI/EcoRI fragment from the 5' region of pcASA2 2-1 (FIG. 1) was used as probe. This analysis identified a 5.9 kilobase pair EcoRI fragment, which was subsequently cloned into the plasmid vector pBSK (Stratagene, La Jolla, Calif.). This clone was designated pDPG668.

To obtain cDNA clones corresponding to the beta-subunit of anthranilate synthase, an oligonucleotide 40 bases in length (ASB-1, TGCATTGGAGAGGCATTTGGATGAAAGATTATCCGTGCTC, SEQ ID NO:7) was designed to match the MZEORFH (GenBank M95067) sequence. The MZEORFH sequence corresponds to a randomly-isolated maize cDNA which was shown to exhibit sequence similarity to the Arabidopsis ASB 1 gene (GenBank L22585; Niyogi et al., Plant Cell, 5, 1011 (1993)). The ASB-1 oligonucleotide was end-labelled with $^{32}$P-ATP using polynucleotide kinase as recommended by the manufacturer (BRL). Screening of the maize embryo cDNA library in the LambdaZAP vector with radiolabelled ASB-1 as probe was performed as described for isolation of genomic clones corresponding to the alpha-subunit of anthranilate synthase. A single clone, designated pcASB1-4, was obtained by this screening protocol. A limited amount of sequence information was obtained from the ends of this clone using vector-specific primers, and an internal portion of the sequence was obtained using the ASB-1 oligonucleotide as a sequencing primer. The internal nucleotide sequence obtained clone ASB1-4 exhibited 71% sequence identity to the Arabidopsis ASB1 gene sequence over a region of 93 nucleotides (positions 670 to 763 of GenBank L22585) (SEQ ID NO:8, FIG. 6).

EXAMPLE 2

Genetic Mapping of the 5-MT Resistance Trait in Maize and of cDNA Sequences Corresponding to Genes Encoding Anthranilate Synthase Sequences The 5-MT resistance trait present in the maize line C28 was localized to the short arm of chromosome 1 using waxy reciprocal translocations. C28 plants homozygous for the 5-MT resistance trait were crossed by a series of waxy translocation stocks obtained from the Maize Genetics Stock Center, Urbana, Ill. F1 plants obtained from these crosses were subsequently crossed to a homozygous waxy tester stock, and progeny from this testcross were separated into starchy [Wx/(?)] and waxy [wx/wx] kernels using routine iodine staining procedures. Kernels of each class were subsequently subjected to a root growth bioassay for 5-methyltryptophan resistance as described by Hibberd et al., U.S. Pat. No. 4,581,847. Linkage between the 5-MT resistance trait and Wx was observed in progeny obtained from initial crosses involving wx stock TI-9c: of 91 Wx kernels analyzed, 77 were resistant to 5-MT and 14 were sensitive to 5-MT; of 104 wx/wx kernels analyzed, 28 were resistant to 5-MT and 76 were sensitive to 5-MT.

Linkage to markers on the short arm of chromosome 1 was established by crossing a tester stock (sr1/sr1zb4/zb4 P1-ww) with a C28 line homozygous for 5-MT resistance, and subsequent testcrossing of the F1 progeny back to the tester stock. The resultant progeny were scored for 5-MT resistance and for the presence of striate leaves. Of 134 individuals examined, 61 were classified as 5-MT resistant, normal leaves; 7 as 5-MT resistant, striate leaves; 9 as 5-MT sensitive, normal leaves, and 57 as 5-MT sensitive, striate leaves. These data indicated that the 5-MT locus defined by the C28 mutation is approximately 12 centimorgans (cm) from the sr1 locus on the short arm of chromosome 1.

The map positions of genes corresponding to the maize anthranilate synthase cDNA clones were determined to ascertain whether any of these loci map near the 5-Mtr locus defined by the C28 mutation. Three different probes which were specific for the three ASA2 cDNA clones (ASA2 1-1, ASA2 2-1, and ASA2 3-1) and the pcASB1-4 clone were mapped using a Recombinant Inbred mapping population of maize plants developed to facilitate placement of genes on the maize genetic map (Burr et al., Genetics, 18, 519 (1988)). The results are as follows:

TABLE 1

| Probe | Location[a] |
| --- | --- |
| ASA2 | 3-11L253 |
| ASA2 | 3-19SASA2 2-11S073.5 |
| ASA2 | 1-11S073.5 |
| ASB1 | 42S087 |
| ASB1 | 410L080 |
| ASB1 | 49L083.6 |
| ASB1 | 42L156 |
| Ts21 | S085 |

[a]Location refers to chromosome number, arm, and map units from the first probe on the short arm as mapped on the 1994 RI map (Maize Genetics Newsletter 68, 198 (1994)).

These data indicate that pcASA2 2-1 and pcASA2 1-1 map approximately 12 cm distal to the Ts2 locus, a locus mapping to the short arm of chromosome 1. Since sr1 and Ts2 are separated by 24 units on the morphological map, the location of anthranilate synthase sequences in this region of the genome is consistent with the location of the 5-Mtr trait. In addition, since nucleotide sequence data of clones pcASA2 2-1 and pcASA2 1-1 indicated that these two clones are identical in sequence, and mapping data indicated they are derived from the same region of the maize genome, it was concluded that these two clones correspond to the same anthranilate synthase gene and that this gene corresponds to the 5-MT locus defined by the C28 mutation. The clone pcASA2 3-1 mapped to loci on two other chromosome arms, and the pcASB1-4 clone mapped to loci on four other chromosome arms. These latter two clones therefore do not correspond to loci that are modified in the C28 line.

EXAMPLE 3

Characterization of DNA Sequences Corresponding, to Maize Genes Encoding Anthranilate Synthase Alpha Subunits Of the four clones (pcASA2 1-1, 2-1, 4-1, 5-3) which exhibited sequence identity for the regions initially analyzed, pcASA2 2-1 was determined to be the longest clone by restriction enzyme mapping analysis of the clones. Thus, pcASA2 2-1 was selected for further analysis. The entire nucleotide sequence of the maize cDNA contained in the clone pcASA2 2-1, designated below as pDPG600 was determined using standard procedures employing the Sequenase system (USB, Cleveland, Ohio). Sequence analysis was performed using oligonucleotide primers specific for the cloning vector, pBSK, to obtain sequence information from the ends of the cDNA fragment, and oligonucleotide primers specific for internal sequences based on internal sequence information from subclones generated from pcASA2 2-1 which were cloned in pBSK with endpoints at the EcoRV site shown in FIG. 1. The sequence information obtained through the use of vector-specific primers was extended by the use of oligonucleotide primers based on the pDPG600 nucleotide sequence and "walking" along the length of the clone in both directions. Sequence analysis and oligonucleotide primer design was performed using the GeneWorks (Intellegenetics, Inc., Mountain View, Calif.) and Oligo (National Biosciences, Plymouth, Minn.) software programs, respectively.

The 5' end of the ASA2 transcript was identified by primer extension reactions in which reverse transcriptase was used to extend the oligonucleotide primer PE-1 (SEQ ID NO:9) using RNA isolated from developing maize embryos as a template, in the presence of a radiolabelled deoxynucleotide triphosphate under standard reaction conditions (Sambrook et al., *Molecular Cloning: A Laboratory Manual*, (1989)). Comparison of the size of the primer extension product with a sequencing ladder generated from the pDPG668 genomic clone with the PE-1 primer indicated that the 5' end of the transcript corresponds to a position 65 base pairs upstream of the 5' end of the pDPG600 cDNA clone. There is no ATG between the 5' end of the transcript and the first ATG in the cDNA sequence, indicating that the maize anthranilate synthase transcript corresponding to pDPG600 has a 5' untranslated region (UTR) of 142 nucleotides.

Figure 2:
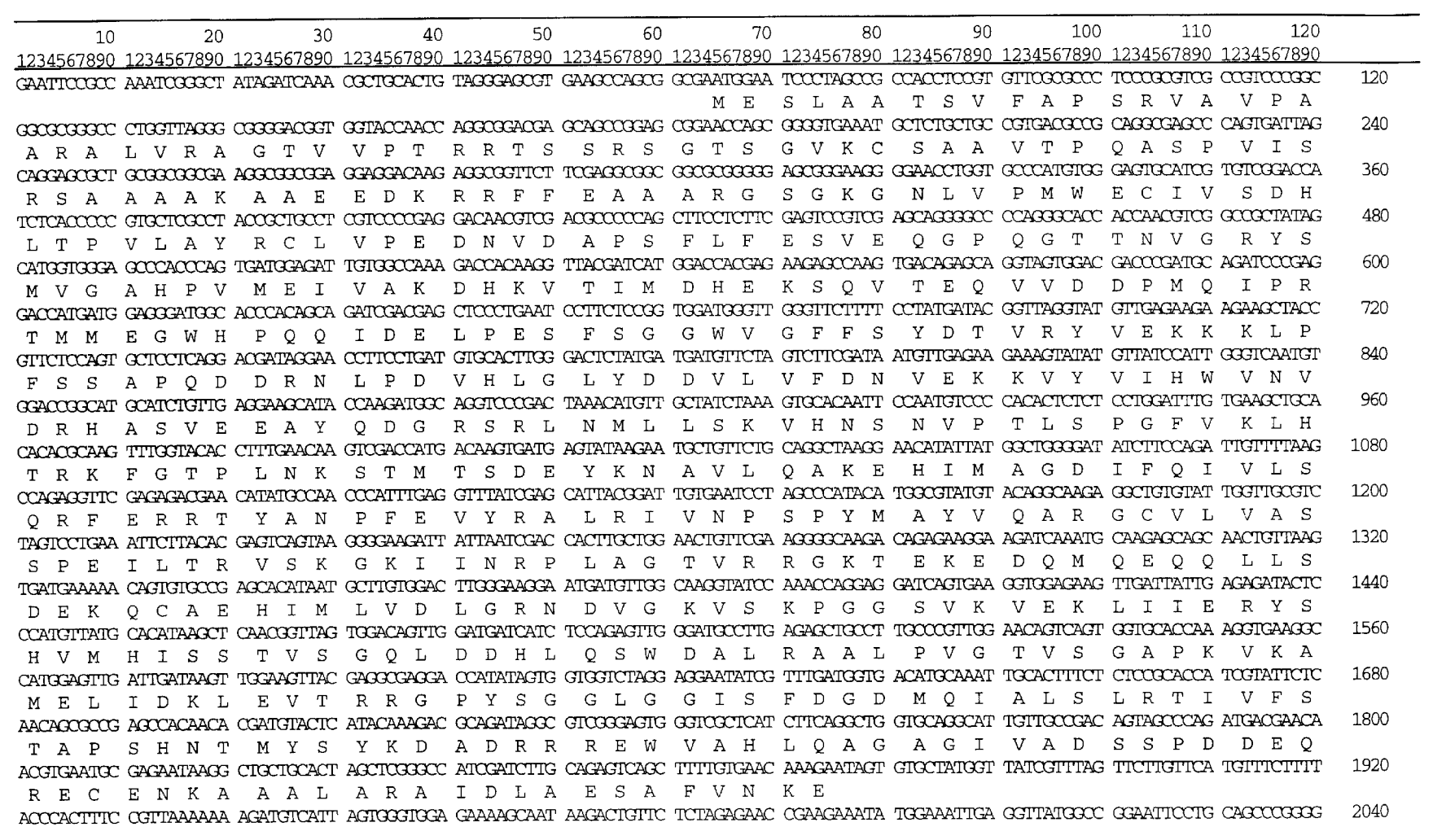

The cDNA insert in pDPG600 is 2060 base pairs in length and contains an open reading frame (ORF) of 1845 nucleotides (FIG. 2, SEQ ID NO:1). This ORF, the 5' end of which represents the initial ATG in the pDPG600 sequence, corresponds to a polypeptide of 615 amino acids with a predicted molecular mass of 67.8 kilodaltons. Previous work has indicated that most enzymes involved in biosynthesis of aromatic acids are localized in plastids (Zhao et al., *J. Biol. Chem.*, 270, 6081 (1995)). Because the genes encoding these biosynthetic enzymes are nuclear-encoded genes, the targeting of the gene product to the plastid is through the presence of a transit peptide at the 5' end of the coding sequence. The predicted polypeptide encoded by pDPG600 (SEQ ID NO:2) contains a putative transit peptide cleavage sequence (VKC▼S) at amino acid residues 44–47, which is consistent with the consensus transit peptide cleavage signal of (VII)X(A/C)▼A as described by Gavel and Von Heijne, *FEBS Lett.*, 261, 455 (1990)). The actual amino acid sequence at the N-terminus of the maize anthranilate synthase enzyme has not yet been determined. If amino acid residues 1–46 function as a transit peptide, and if this sequence is removed during transport into the plastid, a polypeptide of 569 amino acids with molecular mass of 63.2 kilodaltons would be expected.

To determine the size of the mature anthranilate synthase alpha-subunit encoded by clone pDPG600, polyclonal antibodies were generated to a portion of the polypeptide encoded by the pDPG600 cDNA sequence. An EcoRV/XbaI restriction fragment from pDPG600, corresponding to nucleotide positions 1093 to 2017 of the pDPG600 sequence, was inserted into the protein expression vector pProEx-1 (BRL) which had been cleaved with StuI and XbaI, restriction enzymes which have recognition sites in the multiple cloning site of the vector. Both EcoRV and StuI generate blunt ends. This resulted in a clone that contained codons 344 through 615 of pDPG600 3' to the pProEx-1 leader sequence containing the 6xHis tag sequence. This clone contains 3' to the pDPG600 sequence a termination codon and a 103 base pair UTR. This clone was transformed into DHα5. Expression of the recombinant fusion protein was induced by 0.6 mN isopropyl-β-D-thiogalactoside. The presence of the 6xHis tag in the recombinant fusion protein allowed for affinity purification of the recombinant fusion protein using a nickel nitrilo-tri-acetic acid resin as recommended by the manufacturer, BRL (see Dobeli et al., U.S. Pat. No. 5,284,933, issued Feb. 8, 1994, incorporated by reference herein).

A total of 7.8 mg of the 33.5 kD recombinant fusion protein, estimated to be approximately 95% pure by SDS-PAGE analysis was obtained. A total of 4 mg of this protein was provided to HTI Bio Products, Inc. (Ramona, Calif.) for production of polyclonal antibodies in rabbits. Analysis of maize protein extracts by SDS-PAGE and immunoblotting with this polyclonal rabbit sera revealed the presence of a 63 kD polypeptide in these extracts. This data strongly suggests that the mature maize anthranilate synthase enzyme has a molecular mass consistent with the cleavage of a ca. 4 kilodalton transit peptide sequence.

The amino acid sequence predicted from the pDPG600 nucleotide sequence exhibits a significant amount of homology to sequences of other isolated genes encoding anthranilate synthase, particularly to those of Arabidopsis (FIG. 3). The maize anthranilate synthase predicted amino acid sequence exhibits 63% identity to each of the Arabidopsis anthranilate synthase alpha subunits encoded by the ASA1 (SEQ. ID NO:3) and ASA2 (SEQ. ID NO:4) genes. As shown in FIG. 3, similarity between the maize and the Arabidopsis ASA2 sequences is apparent after amino acid position 101 in the pDPG600 predicted amino acid sequence. These similarities clearly indicate that pDPG600 corresponds to a maize homologue of the Arabidopsis anthranilate synthase gene ASA2.

EXAMPLE 4

Identification of a Single Base-Pair Difference in Anthranilate Synthase cDNA Sequences Obtained from Maize Plants Homozygous for the 5-MT Resistance Trait As described above, the maize anthranilate synthase gene represented by pDPG600 maps to the same region of the genome as does the 5-MT resistance trait, strongly suggesting that modification of this gene in the C28 cell line led to decreased sensitivity with respect to tryptophan feedback inhibition. Analysis of *S. typhurium* anthranilate synthase mutants in the subunit encoded by the TrpE gene (Caligiuri and Bauerle, *J. Biol. Chem.* 266, 8328 (1991)) identified two regions of the anthranilate synthase polypeptide involved in feedback inhibition. Although most of these mutant polypeptides exhibited a decreased affinity for tryptophan with no change in substrate or catalytic activity, an 18 amino acid region of TrpE was identified that is important for tryptophan regulation. This region was chosen for analysis of anthranilate synthase sequences from 5-MT resistant plants.

Nucleotide sequence information from pDPG600 was used to design a set of primers, A21-8 (SEQ ID NO:10) and A21-9 (SEQ ID NO:11), which would amplify a significant portion of the gene, including the 18 amino acid region identified by TrpE mutant analysis. These primers were used in reverse transcriptase-PCR (RT-PCR) assays of RNA obtained from 5-MT resistant plants (leaves, developing embryos, developing endosperm, and germinating embryos). The RT-PCR assays were performed using the reagents supplied by Perkin-Elmer Cetus in the GeneAmp RNA PCR Kit as follows: 1 µg of RNA was subjected to a 20 µl reverse transcription reaction containing 1 mM each dATP, dCTP, dGTP, and dTTP, 5 mM $MgCl_2$, 50 mM KCl, 10 mM Tris-HCl, pH 8.3, 50U MMLV reverse transcriptase, and 2.5 µM oligo $d(T)_{16}$. Reactions were performed at 42° C. for 15 minutes followed by a 5 minute incubation at 99° C. Samples were then subjected to PCR in 100 µl reactions containing 0.25 µM of each primer A21-8 and A21-9, 200 µM each dATP, dCTP, dGTP, and dTTP, 1 mM $MgCl_2$, 50 mM KCl, 10 mM Tris-HCl, pH 8.3, and 2.5U Taq DNA polymerase. Reactions were performed in the wells of microtiter plates in an MJ Research thermal cycler (Model PTC-100) with a 96 well plate block. Thermal cycling conditions were as follows: initial denaturation at 97° C. for 2 minutes; 3 cycles of 97° C. for 1 minute, 56° C. for 1 minute, and 72° C. for 1 minute; 33 cycles of 94° C. for 1 minute, 56° C. for 1 minute, and 72° C. for 1 minute; and a final extension of 72° C. for 4 minutes. All samples assayed yielded the expected size band of 700 base pairs as predicted from the pDPG600 sequence.

To insert these sequences into a plasmid vector, the "TA" cloning technique, which takes advantage of the fact that the Taq polymerase used during PCR amplification adds a single dA residue onto the 5' ends of amplification products (Holton and Graham, *NAR,* 19, 1156 (1991)), was used. The plasmid vector pBSK was cleaved with EcoRV to generate blunt ends and subsequently modified by the addition of a single dT residue to each resultant 3' end through the action of terminal deoxynucleotide transferase. Ligation of the RT-PCR products to the T-tailed vector was achieved through association of the 5' A overhang in the amplification products with the 3' T overhang on the vector and the activity of T4 DNA ligase. Ligation reactions were used to transform competent bacteria. DNA from individual bacterial clones was then subjected to sequence analysis to examine the region corresponding to the residues implicated in 5-MT resistance. Both strands of four clones, each from a different RNA source, were sequenced. Each of these clones (from leaf, 24 DAP endosperm, 24 DAP embryo, or 2 day germinating embryo from homozygous C28 plants) were identical in sequence, and each of these four clones contained a single base substitution (T to A) corresponding to position 1161 in the pDPG600 sequence. This nucleotide substitution results in a methionine to lysine residue substitution at codon position 366 relative to the initiator methionine codon. This residue is one which is implicated in feedback inhibition through *S. typhimurium* TrpE mutant analysis. Other residues in the TrpE gene have been implicated as being involved in tryptophan feedback regulation, as indicated in the maize and Arabidopsis sequences shown in FIG. 3. It is likely that amino acid substitutions at these other residues will also result in a modification of tryptophan feedback sensitivity of an anthranilate synthase.

To generate cDNA clones containing the entire protein coding region of maize anthranilate synthase with the met to lys substitution at codon position 377, a region from one of the RT-PCR-amplified clones (pcASA2m4) with the 5-MT resistance allele was substituted for the corresponding region of the wild-type pcASA2 1-1 clone. This was accomplished by cleaving both pDPG600 and pcASA2m4 with the restriction enzymes Nsi1 and Van91I to generate a 403 base pair NsiI/Van91I fragment with the C28 mutation (SEQ. ID NO:12) and a 351 base pair Van91I fragment, and, in the case of pDPG600, a 4258 base pair Nsi1/Van91I fragment which contains the 5' region upstream of the Nsi1 site and the 3' region downstream from the second Van91I site fused to the pBSK vector. The 403 base pair Nsi1/Van91I fragment from pcASA2m4 was isolated and used in a three-way ligation reaction which also contained the 351 base pair Van91I fragment and the 4258 base pair Nsi1/Van91I fragment from pDPG600. Because the five residues within the two Van91I recognition sites of pDPG600 are different from each other, the only recombinant DNA molecules which could be obtained from such a three-way ligation are those that reconstruct the original sequences within the Van91I sites. A total of 10 clones obtained from this three-way ligation were selected and screened for the presence of the Nsi1 site and the two Van91I sites. All 10 clones contained each of these sites. Two clones were selected for nucleotide sequence analysis with the oligonucleotide primer A21-8 (SEQ ID NO:10), and both clones were found to contain the T to A substitution at position 1161. This confirmed that a recombinant DNA clone corresponding to a full-length anthranilate synthase cDNA clone, but which differed from the wild type sequence by a single nucleotide and which changed the codon at position 366 from a methionine codon to a lysine codon (SEQ ID NO:16), had been obtained. This clone was designated pDPG602(SEQ ID NO:12).

EXAMPLE 5

Generation and Identification of Maize Transformants Containing the Modified Anthranilate Synthase Sequence The anthranilate synthase sequence from pDPG602 was placed under control of the 35S CaMV promoter to determine if expression of this modified anthranilate synthase sequence was capable of conferring 5-MT or 6-MA resistance, and/or the tryptophan overproduction trait, to maize cell cultures. To generate the appropriate gene constructs with the 35S promoter, the plasmid pDPG165 was cleaved with restriction enzymes XbaI and KpnI, isolating the fragment containing the 35S CaMV promoter and the Tr7 terminator fused to the pUC19 plasmid backbone, and ligating this fragment to the 82 base pair XbaI/KpnI fragment from the multiple cloning site of the cloning vector pBSK to generate pDPG603.

pDPG602 was cleaved with restrictions enzymes BamHI and ClaI, which cleave sequences present in the multiple cloning sites flanking the cDNA fragment. The resultant 2107 base pair fragment was ligated into the BamHI and ClaI sites present in the multiple cloning site of pDPG603 to generate a construct designated 35S/ASA2C28. The orientation of the recombinant plasmid obtained from this ligation is such that the modified anthranilate synthase cDNA sequence will be 3' to the 35S CaMV promoter and 5' to the Tr7 terminator sequence, thus placing the modified anthranilate synthase sequence under the transcriptional control of these two regulatory sequences such that a functional transcript encoding the modified anthranilate synthase enzyme would be produced in plant cells. A similar construct, using the wild type anthranilate synthase sequence from pDPG600, was prepared using the same strategy as that described for generation of 35S/ASA2C28. The wild-type construct, in which the wild type anthranilate synthase sequence is under control of the 35S and Tr7 sequences, was designated 35S/ASA2.

To evaluate expression of the anthranilate synthase sequences contained in 35S/ASA2C28 and 35S/ASA2 with respect to their ability to confer 5-MT or 6-MA resistance, or the trait of tryptophan overproduction, to maize cells, these gene constructs were used in transformation experiments. These experiments involved co-transformation of either 35S/ASA2C28 or 35S/ASA2 along with the plasmid pDPG165 (35S/bar/Tr7), which allows for selection of transformants on bialaphos-containing media. Ears from the crosses AB80(R1)xCW and CWxAB80(R1) were harvested 10 days post-pollination and the immature embryos were excised and plated on Medium 2365 (Medium 2366 with 2% sucrose, see Table 2) at 10 embryos per plate. Most of the embryos ranged in length from 1.2–1.7 mm with a few smaller than 1.2 mm. Embryos were arranged in concentric circles on the osmotic adjustment Medium 2366 (see Table 2) at 30 embryos per plate 4 days after isolation.

Approximately four hours later, the embryos were bombarded using a helium gun (see Davis et al., PCT publication WO 95/06128, Mar. 2, 1995). One of two plasmid combinations, 35S/ASA2+pDPG165 or 35S/ASA2C28+pDPG165, was used for each plate in order to obtain transformants. After a 2-day recovery period, preselection was started on Medium 2377 (see Table 2) with 8–10 embryos per plate. After 15 days in medium 2377, the embryos were moved to selection media, either Medium 2066 (see Table 2) or Medium 2071, at one embryo per plate in order to eliminate cross-feeding between embryos. Transformants were identified after 12 weeks of incubation on bialaphos selection media.

To identify those bialaphos-resistant transformants which carried either the 35S/ASA2C28 or 35S/ASA2 constructs, individual cultures were assayed by PCR analyses. DNA was extracted from 100–200 mg of callus tissue using the Puregene D-5500A Kit (Gentra Systems Inc.) and resuspended in 150 $\mu$l of $H_2O$. Five $\mu$l of each sample was then subjected to a PCR in a 50 $\mu$l final volume containing 0.25 $\mu$M of each primer A21-8 (SEQ. ID NO:10) and A21-9 (SEQ. ID NO:11), 3.0 mM $MgCl_2$, 20% glycerol, 200 $\mu$M each dATP, dCTP, dGTP, and dTTP, 50 mM KCl, 10 mM Tris-HCl, pH 8.3, and 1.25U Taq DNA polymerase. Reactions were performed in the wells of microtiter plates in an MJ Research thermal cycler (Model PTC-100) with a 96 well plate block. Thermal cycling conditions were as follows: initial denaturation at 97° C. for 2 minutes; 3 cycles of 97° C. for 1 minute, 56° C. for 1 minute, and 72° C. for 1 minute; 33 cycles of 94° C. for 45 seconds, 56° C. for 45 seconds, and 72° C. for 45 seconds; and a final extension of 72° C. for 4 minutes. Reaction products were analyzed by agarose gel electrophoresis for the presence of a 700 base pair product.

TABLE 2

| Media No. | Basal Medium | Sucrose | pH | Other Components (Amount/L) |
|---|---|---|---|---|
| 2366 | N6 | 12% | 5.8 | 1 mg 2,4-D 17 mg $AgNO_3$, 1 mg thiamineHCl, 0.5 mg nicotinic acid, 0.5 mg pyridoxine HCl, 2.9 g proline, 100 mg casamino acids, 2 mg glycine, 1.8 g phytagel |
| 2377 | N6 | 2% | 5.8 | 1 mg 2,4-D, 1 mg bialaphos, 17 mg $AgNO_3$, 1 mg thiamine HCl, 0.5 mg nicotinic acid, 0.5 mg pyridoxine HCl, 2.9 g proline, 100 mg casamino acids, 2 mg glycine, 1.8 g phytagel |
| 2066 | N6 | 2% | 5.8 | 1.5 mg 2,4-D, 3 mg bialaphos, 1 mg thiamine HCl, 0.5 mg nicotinic acid, 0.5 mg pyridoxine HCl, 690 mg proline, 200 mg casamino acids, 2 mg glycine, 2.5 g phytagel |
| 2071 | N6 | 2% | 5.8 | 1 mg 2,4-D, 3 mg bialaphos, 1 mg thiamine HCl, 0.5 mg nicotinic acid, 0.5 mg pyridoxine HCl, 2.9 g proline, 100 mg, casamino acids, 2 mg glycine, 1.8 g phytagel |

TABLE 2-continued

| Media No. | Basal Medium | Sucrose | pH | Other Components (Amount/L) |
|---|---|---|---|---|
| 211V | N6 | 2% | 5.8 | 1 mg 2,4-D, 17 mg AgNO$_3$, 1 mg thiamine HCl, 690 mg proline, 900 mg asparagine, 100 mg casamino acids, 500 mg MES |
| 211SV | N6 | 12% | 5.8 | 1 mg 2,4-D, 17 mg AgNO$_3$, 1 mg thiamine HCl, 690 mg proline, 900 mg asparagine, 100 mg casamino acids, 500 mg MES |
| 207D | N6 | 2% | 5.8 | 1.5 mg 2,4-D, 200 mg casamino acids, 3 mg bialaphos |

N6 medium is described in Chu et al., ScientiaSinica, 18, 659 (1975).

EXAMPLE 6

Analysis of Maize Transformants Containing the Gene Construct 35S/ASA2C28 for 5-methyltryptophan Resistance and for Tryptophan Overproduction A total of 15 transformants with 35S/ASA2C28 and pDPG165, or pDPG165 alone, that had been selected on bialaphos-containing medium, were evaluated for their ability to grow on 5-MT-supplemented media. Of these, 10 were PCR-positive for 35S/ASA2C28 and five contained only the pDPG165 construct. Of the 10 35S/ASA2C28-containing transformants, seven exhibited vigorous growth after four weeks on media supplemented with 5-MT at concentrations of 33 $\mu$M or 100 $\mu$M. Samples were scored for growth using an arbitrary scale, with a rating of "0" indicating little or no growth on 100 $\mu$M 5-MT media, a rating of "1" indicating some growth on 100 $\mu$m 5-MT media but not as much as on control media, and a rating of "2" indicating no difference in growth between control and 100 $\mu$M 5-MT media. The five controls exhibited little or no growth on 100 $\mu$M 5-MT media.

In another experiment, a total of 29 bialaphos-resistant transformants, 17 of which were PCR-positive for 35S/ASA2C28, 1 of which was PCR-positive for 35S/ASA2, and 11 of which contained neither construct, were transferred to 207D media supplemented with 100 $\mu$M 5-MT, 200 $\mu$M 5-MT, 100 $\mu$M 6-MA, or 200 $\mu$M 6-MA. Five transformants carrying the 35S/ASA2C28 construct grew equally well on all of the media tested, four showed some inhibition of growth on either 100 $\mu$M or 200 $\mu$M 6-MA media but not on either concentration of the 5-MT media, and one showed reduced growth in the presence of both concentrations of 6-MA and 200 $\mu$M 5-MT, but not on 100 $\mu$M 5-MT. Another eight lines exhibited little or no growth on either 5-MT or 6-MA media, suggesting that the transgene was not expressed in those lines. Most of the untransformed lines exhibited little or no growth on either 6-MA or 5-MT media, and the single 35S/ASA2 transformant tested did not grow on either type of supplemented media. Thus, it appears that 6-MA is a more potent inhibitor of growth than is 5-MT at equimolar concentrations. These data indicate that cells transformed with the 35S/ASA2C28 construct express the 5-Mtr trait and can exhibit vigorous growth at concentrations of 5-MT or 6-MA up to 200 $\mu$M.

To determine if the presence of the 35S/ASA2C28 construct in these transformants is associated with tryptophan overproduction, the levels of free tryptophan in these callus cultures were evaluated using a modification of the procedure described by Jones et al. (*Analyst*, 106, 968 (1981)). A weighed sample of callus tissue was ground with a Polytron (Brinkmann Instruments) for 1 minute in extraction buffer (25% acetonitrile, 10 mM sodium acetate buffer, pH 7.0) at a ratio of 5 ml buffer to 1 gram of tissue. Samples were shaken at about 4° C. for 2 hours and then centrifuged at 3500×g for 10 minutes followed by filtration through a 0.5 micron filter. The resultant supernatant was analyzed by HPLC using a reverse phase, C-18 column (4.5×25 cm), fluorescence detection (excitation 254 nm, emission 320 nm) and isocratic elution (25 mM sodium acetate buffer, pH 3.8:methanol, 3:1 vol/vol) at a flow rate of 1 ml/minute and a temperature of 50° C. Twenty $\mu$l of sample was injected for each run. Analysis of peaks was performed using MAXIMA software (Waters Instruments) with further data processing in an EXCEL (Microsoft) spreadsheet.

Results of tryptophan analyses of these lines are shown in Table 3 and Table 4. Of the lines assayed, two (TRPA030 and TRPB044) contained substantially elevated levels of tryptophan relative to controls. These levels were in the range of 60 to 102 ppm free tryptophan. Most of the other 35S/ASA2C28 lines contained levels in the range of 20 to 30 ppm free tryptophan, while levels in most of the controls were 6 to 11 ppm. The level of tryptophan in line TRPA030 is similar to that of the original C28 callus line that is resistant to 5-MT. These data indicate that maize cells containing the gene construct 35S/ASA2C28 are capable of tryptophan overproduction in comparison to maize cells that do not contain this construct.

TABLE 3

| TRANSFORMANT | 35S/ASA2 C28 | Trp (ppm) | Growth Rating |
|---|---|---|---|
| TRPA 030 | + | 101.6 | 2 |
| TRPA 015 | + | 28.8 | 2 |
| TRPA 032 | + | 27.0 | 1 |
| TRPA 027 | + | 26.3 | 2 |
| TRPA 016 | + | 16.8 | 2 |
| TRPA 011 | + | 14.7 | 2 |
| TRPA 033 | + | 14.4 | 1 |
| TRPA 013 | − | 15.6 | 0 |
| TRPA 019 | − | 10.1 | 0 |

TABLE 4

| Transformant | Transgene | 207D | +100 $\mu$M 5-MT | +200 $\mu$M 5-MT | +100 $\mu$M 6-MA | +200 $\mu$M 6-MA | TRP (ppm) |
|---|---|---|---|---|---|---|---|
| TRPB 044 | p605 | 2 | 2 | 2 | 2 | 2 | 62.5 |
| TRPB 043 | p605 | 2 | 2 | 2 | 2 | 2 | 25.3 |
| TRPB 048 | p605 | 2 | 2 | 2 | 2 | 2 | 24.98 |

TABLE 4-continued

| Transformant | Transgene | 207D | +100 µM 5-MT | +200 µM 5-MT | +100 µM 6-MA | +200 µM 6-MA | TRP (ppm) |
|---|---|---|---|---|---|---|---|
| TRPB 049 | p605 | 2 | 2 | 2 | 2 | 2 | 22.41 |
| TRPB 019 | p605 | 2 | 2 | 1 | 1 | 1 | 20.7 |
| TRPB 042 | p605 | 2 | 2 | 2 | 2 | 2 | 20.7 |
| TRPB 051 | p605 | 2 | 2 | 2 | 1 | 1 | 15.02 |
| TRPB 011 | p605 | 2 | 2 | 2 | 2 | 1 | 12.56 |
| TRPB 050 | p605 | 2 | 2 | 2 | 1 | 1 | 10.49 |
| TRPB 017 | p605 | 2 | 1 | 0 | 0 | 0 | |
| TRPB 022 | p605 | 2 | 0 | 0 | 0 | 0 | |
| TRPB 025 | p605 | 2 | 0 | 0 | 0 | 0 | |
| TRPB 031 | p605 | 2 | 2 | 1 | 1 | 0 | |
| TRPB 038 | p605 | 2 | 0 | 0 | 0 | 0 | |
| TRPB 040 | p605 | 2 | 0 | 0 | 0 | 0 | |
| TRPB 046 | p605 | 2 | 1 | 1 | 1 | 0 | |
| TRPB 021 | p605 | 2 | 2 | 1 | 1 | 0 | |
| TRPB 033 | p604 | 2 | 0 | 0 | 0 | 0 | 6.31 |
| TRPB 029 | — | 2 | 2 | 2 | 1 | 1 | 21.68 |
| TRPB 014 | — | 2 | 0 | 0 | 0 | 0 | 11.07 |
| TRPB 037 | — | 2 | 0 | 0 | 0 | 0 | 10.79 |
| TRPB 028 | — | 2 | 1 | 1 | 1 | 1 | 10.42 |
| TRPB 020 | — | 2 | 0 | 0 | 0 | 0 | 7.77 |
| TRPB 015 | — | 2 | 1 | 0 | 0 | 0 | |
| TRPB 018 | — | 2 | 0 | 0 | 0 | 0 | |
| TRPB 024 | — | 2 | 1 | 1 | 1 | 0 | |
| TRPB 039 | — | 2 | 1 | 0 | 0 | 0 | |
| TRPB 041 | — | 2 | 0 | 0 | 0 | 0 | |
| TRPB 047 | — | 2 | 1 | 0 | 0 | 0 | |

EXAMPLE 7

Analysis of Maize Transformants Containing the Gene Construct 3SS/ASA2C28 for Anthranilate Synthase Activity Exhibiting Reduced Sensitivity to Tryptophan Feedback Inhibition To determine whether maize transformants carrying the 35S/ASA2C28 gene construct contained anthranilate synthase activity which was less sensitive to tryptophan feedback inhibition than the anthranilate synthase present in control cells, anthranilate synthase enzyme assays were performed on selected transformed cell lines. Anthranilate synthase assays were performed essentially as described by Widholm (*Biochimica et Biophysica Acta,* 279, 48 (1972)). Five grams of callus tissue was ground with a Polytron (Brinkmann Instruments) for 1 minute with an equal volume of extraction buffer (100 mM HEPES, pH 7.5, 0.4 mM β-mercaptoethanol, 0.2 mM EDTA, 1 mM MgSO$_4$, 100 µM glutamine, 40% glycerol). The resultant homogenate was centrifuged at 6000×g for 20 minutes and the supernatant was de-salted on a Biorad P6-DS column (12 ml bed volume, 4 ml sample applied). The enzyme assay was run at 30° C. and the production of anthranilate was continuously measured spectrofluorometrically at a 340 nm excitation wavelength and a 400 nm emission wavelength (slit widths 5 and 10 nm, respectively). The final 1 ml reaction mixture contained up to 250 µl of enzyme extract and 8 µmoles of MgSO$_4$, 40 µmoles of L-glutamine and 1 µmole of chorismate. Reactions were run in the presence of 0 to 15 µM tryptophan. Protein content of samples was determined by the standard Bradford assay. Anthranilate standards were used to quantify emission readings.

Figure 4:
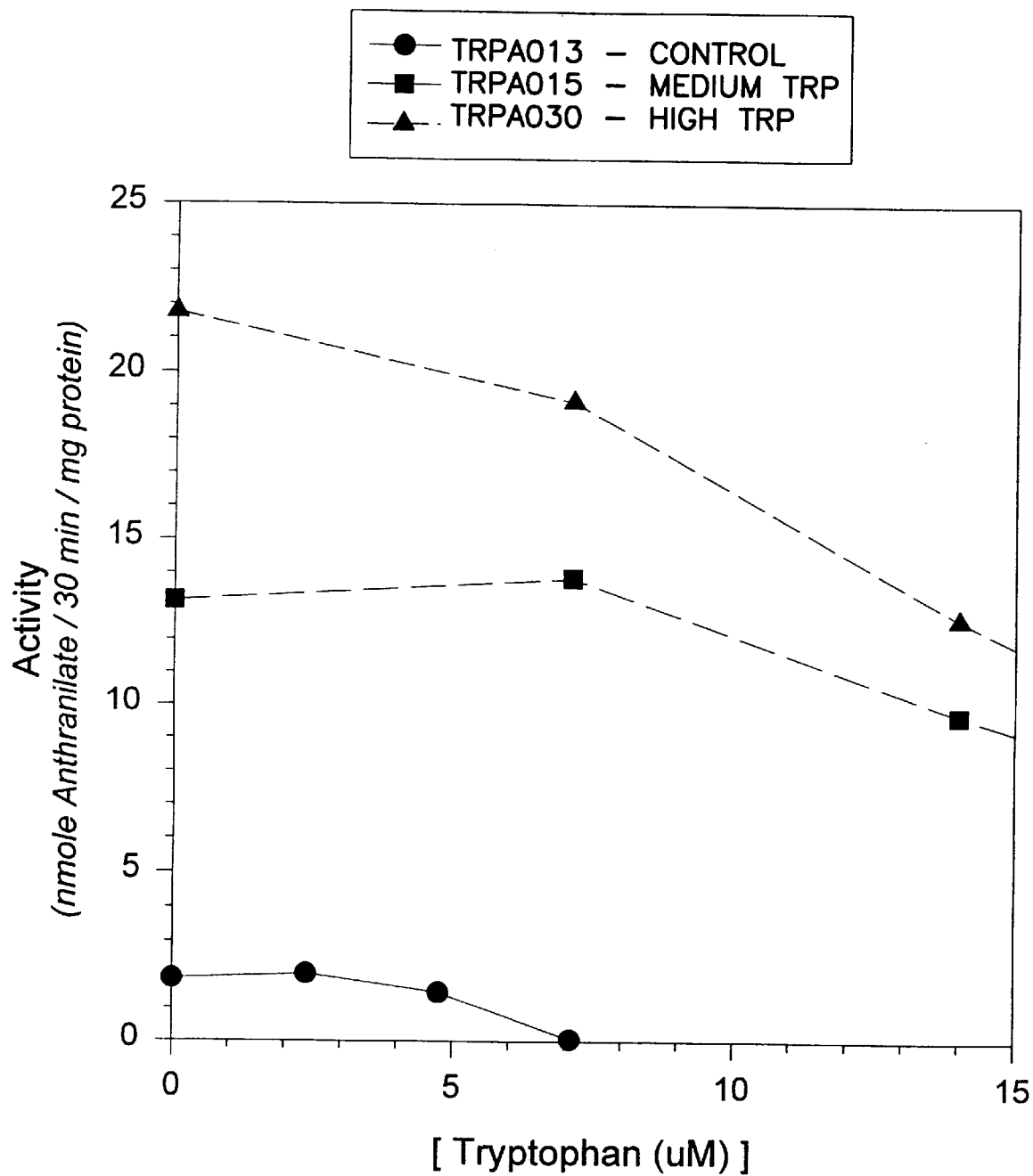
FIG. 4 is a graph of the activity (nmole anthranilate/30 minutes/mg protein) versus tryptophan concentration ($\mu$M) for 3 transformants (TRPA015, TRPA030, and TRPA013).

As can be seen in FIG. 4, the cell lines TRPA030 and TRPA015, both of which contain the 35S/ASA2C28 gene construct, exhibited ability to grow on 100 µM 5-MT, contained higher tryptophan levels relative to tryptophan levels in controls, and exhibited levels of anthranilate synthase activity higher than those of the control cell line TRPA013, which does not contain the 35S/ASA2C28 construct. The anthranilate synthase activity in the 35S/ASA2C28 lines also exhibited greater tolerance to tryptophan inhibition than did the control.

EXAMPLE 8

Characterization of the Transcriptional Promoter Region from the Maize ASA2 Gene To evaluate the utility of the 5' regulatory sequence of the maize anthranilate synthase gene ASA2 in directing gene expression in maize cells, a fragment from the clone pDPG668 was inserted 5' to a GUS reporter gene. This was done by restriction mapping pDPG668, which allowed the identification of an Xba/PvuII fragment that contains 12 base pairs of 5'UTR (including the PvuII site) and about 1100 base pairs of 5' flanking sequence. The Xba/PvuII fragment from pDPG668 was isolated, the Xba overhang filled in with the Klenow fragment of DNA polymerase, and the resultant blunt-ended fragment was substituted for the 35S promoter in pDPG126 (35S/GUS/TR7) by cleaving that plasmid with BamH1 and HindIII to remove the 35S promoter fragment, filling in with Klenow fragment of DNA polymerase I to generate blunt ends, treating with alkaline phosphatase, then ligating this linear vector to the pDPG668 blunt end fragment to generate pDPG671 (Asa2/GUS/Tr7). The pDPG671 construct was introduced into immature maize embryos by particle bombardment as follows: embryos were excised at 10 days post-pollination, maintained on 211V (Table 2) solid medium for two days at 27° C., then transferred to 211SV (Table 2) medium four hours prior to bombardment (see Davis et al., PCT publication WO 95/06128, Mar. 2, 1995). Embryos remained on 211SV for two days post-bombardment, at which time they were transferred to histochemical GUS assay buffer (0.1 M sodium phosphate, pH 7.0, 5 mM potassium ferricyanide, 1 mM EDTA, 1% Triton X-100, 0.3% X-glucuronide). A limited number of blue-staining spots was observed after 24 hours of staining, indicating that the Xba/PvuII fragment from pDPG668 was capable of directing expression of the GUS reporter gene in maize cells. The insert was subjected to nucleotide sequencing analysis. The 1200 nucleotides 5' to the putative translational start site are shown in FIG. 5 (SEQ ID NO:14).

EXAMPLE 9

Procedures that Facilitate Identification of Plants Carrying Either the ASA2 C28 Allele or for Plants Expressing the Transgene Present in the 35S/ASA2C28 Gene Construct As indicated above, the biological nature of 5-MT resistance in the proprietary C28 maize line is due to a mutation in a gene encoding the enzyme anthranilate synthase. The mutation results in a reduction in sensitivity of the enzyme to tryptophan feedback inhibition, therefore allowing for tryptophan overproduction in the cell. This modified enzyme could exhibit a similar tolerance to other tryptophan analogues that exert phytotoxic effects via the tryptophan pathway. The use of one such analogue, 6-MA, was evaluated in assays designed to distinguish plants carrying the maize ASA2 C28 allele from those containing only wild type alleles at this locus.

Spray trials were conducted in which 7-to-10 day-old seedlings of C28/C28 and wild-type sources were sprayed with a solution of 10 mM 6-MA, 10% glycerol, 0.5% Tween-20. Five days after spraying, the wild type plants exhibited chlorosis, particularly between leaf veins, while the C28 plants appeared normal. This indicated that this 6-MA formulation was toxic to wild-type plants but not to C28/C28 plants. The effects of 5-MT and 6-MA on wild type and C28 plants was then compared. This experiment consisted of treating plants representing a variety of genetic backgrounds in which the C28 allele was segregating in a 1:1 ratio. Rows of 20 kernels each, representing eight different C28 backcross conversion populations, were planted in two identical flats. One flat was sprayed with 5-MT and the other with 6-MA (both at a concentration of 10 mM in a solution containing 10% glycerol and 0.5% Tween-20). Plants were sprayed 8 days after planting. Spray treatments were evaluated both 6 and 10 days after spraying. In all cases, clear segregation for resistance to both 5-MT and 6-MA were apparent, and in some cases the effects were more dramatic than in others. In all cases, the 6-MA treatment resulted in a much clearer separation of resistant and sensitive plants.

Given the dramatic effects of 6-MA on sprayed seedlings, it was decided to evaluate the germination ability of seeds carrying the C28 allele in the presence of 6-MA. Previous work with 5-MT, as described in U.S. Pat. No. 4,581,847, indicated that 5-MT inhibited germination in excised embryos. Seeds from seven segregating C28 backcross populations, in addition to C28/C28 and wild type control sources, were germinated between filter paper saturated with a solution of 100 μM 6-MA. After six days incubation, individual seedlings were scored for length of the primary root. All of the C28/C28 seedlings exhibited roots which were greater than 8 cm in length, and root length in all of the control wild type sources was less than 3 cm. In those samples segregating for the C28 allele, plants scored as sensitive were those with roots less than 5 cm in length, and those scored as positive had roots greater than 7 cm in length. This experiment clearly demonstrates that 6-MA at a concentration of 100 μM can be used to identify plants carrying the C28 allele of ASA2 in a seed germination assay.

The reliability of both the seedling spray assay and the seed germination assay involving 6-MA treatment for the identification of plants carrying the ASA2 C28 allele was verified through the use of a molecular marker which physically defines the C28 allele of the ASA2 gene. As described above, the modification in the C28 allele involves a T to A substitution at position 1161 in the pDPG600 nucleotide sequence. This substitution occurs in the context CATG, which is the recognition sequence for the restriction enzyme NlaIII. The T to A substitution present in the ASA2 C28 allele results in a change of sequence from CATG to CAAG, and therefore also results in the loss of the NlaIII recognition sequence at this position. The absence of this site therefore serves as a diagnostic molecular marker for the C28 ASA2 allele. Thus, by amplifying a 500 base pair fragment in a PCR using primers A21-15 (SEQ ID NO:13) and A21-16 (SEQ ID NO:15), which flank this site, and digesting the product with NlaIII, the uncleaved product (500 base pairs) from the C28 allele is easily distinguished from the cleavage products of wild type alleles (400+100 base pair) by agarose gel electrophoresis. This marker has been used to identify the presence of the C28 allele in individuals from populations segregating both 6-MA and 5-MT resistance.

EXAMPLE 10

Analysis of Transgenic Plants Transformed with 35S/ASA2C28

Transgenic plants were regenerated from callus cultures containing 35S/ASA2C28. These plants were used as male or female parents in crosses with plants of elite inbred lines. Kernel progeny from these plants were evaluated for their ability to germinate in the presence of 6-MA and for grain tryptophan content by employing methods described above (Example 9 and Example 6, respectively). Since the transformation process is expected to generate plants hemizygous for a transgene, the kernel progeny in which a transgenic plant is used as one of the parents are expected to segregate 1:1 for the presence of the transgene: half of the progeny will be hemizygous for the transgene and half will be wildtype. The results of an assay in which the ability of kernel progeny from several 35S/ASA2C28 transformants to germinate in the presence of 6-MA was evaluated are shown in Table 5. Progeny from three of these transformants, including TRPA 030, exhibited segregation ratios for 6-MA resistance at ratios close to 1:1. Three other transformants, which exhibited ability to grow on 6-MA media as callus cultures (Table 4), did not produce kernel progeny which were capable of germinating in the presence of 6-MA. This is likely due to differences in the level of expression of the 35S/ASA2C28 transgene in callus cultures and in seed of these specific transformants. These data indicate that transformant TRPA 030, which contains exceptionally high levels of tryptophan in callus cultures (Table 3), exhibits the ability to germinate in the presence of 6-MA.

TABLE 5

| Female parent | Male parent | Number | Number | Root length |
|---|---|---|---|---|
| TRPA 030 | CV | 4 | 6 | 21 cm |
| TRPB 049 | AW | 3 | 7 | 10 cm |
| AW | TRPB 050 | 5 | 5 | 22 cm |
| TRPA 016 | AW | 0 | 10 | <3 cm |
| TRPB 042 03 | AW | 0 | 10 | <3 cm |
| ZY | TRPB 043 | 0 | 10 | <3 cm |

To evaluate the effect of 35S/ASA2C28 transgene expression on tryptophan overproduction in the grain, tryptophan levels in individual kernels from an ear in which transformant TRPA 030 was used as a female parent were determined. As a control, tryptophan levels in kernel progeny from an ear in which transformant TRPB 039, which carries only the selectable marker bar transgene, and not the 35S/ASA2C28 transgene, was used as a female parent. None of the TRPB 039 kernel progeny contained tryptophan levels over 22.8 ppm (range 16.0 to 22.8 ppm), while half of the TRPA 030 progeny exhibited tryptophan levels in the 62–98.9 ppm range and the other half exhibited levels in the 16.5–30.4 ppm range (Table 6). These data clearly demonstrate that kernel progeny resulting from crosses in which TRPA 030 is used as a parent contain levels of tryptophan that are significantly higher than those of transgenic plants that do not carry the 35S/ASA2C28 transgene.

TABLE 6

| Sample | Trp | EAR NAME |
|---|---|---|
| 1 | 19.5 | TRPB 039 X CV |
| 2 | 19.2 | TRPB 039 X CV |
| 3 | 21.7 | TRPB 039 X CV |
| 4 | 17.8 | TRPB 039 X CV |
| 5 | 17.2 | TRPB 039 X CV |
| 6 | 20.6 | TRPB 039 X CV |
| 7 | 21.1 | TRPB 039 X CV |
| 8 | 17.6 | TRPB 039 X CV |
| 9 | 19.3 | TRPB 039 X CV |
| 10 | 22.2 | TRPB 039 X CV |
| 11 | 16.0 | TRPB 039 X CV |
| 12 | 18.7 | TRPB 039 X CV |
| 13 | 16.6 | TRPB 039 X CV |
| 14 | 16.9 | TRPB 039 X CV |
| 15 | 22.8 | TRPB 039 X CV |
| 16 | 21.6 | TRPB 039 X CV |
| 17 | 51.4 | TRPA 030 X CV |
| 18 | 21.2 | TRPA 030 X CV |
| 19 | 62.4 | TRPA 030 X CV |
| 20 | 63.1 | TRPA 030 X CV |
| 21 | 72.9 | TRPA 030 X CV |
| 22 | 98.9 | TRPA 030 X CV |
| 23 | 65.3 | TRPA 030 X CV |
| 24 | 18.1 | TRPA 030 X CV |
| 25 | 62.0 | TRPA 030 X CV |
| 26 | 71.0 | TRPA 030 X CV |
| 27 | 30.4 | TRPA 030 X CV |
| 28 | 18.8 | TRPA 030 X CV |
| 29 | 22.4 | TRPA 030 X CV |
| 30 | 16.5 | TRPA 030 X CV |
| 31 | 25.7 | TRPA 030 X CV |
| 32 | 27.3 | TRPA 030 X CV |

EXAMPLE 11

Use of 35S/ASA2C28 as a Selectable Marker for Plant Transformation

Since the 35S/ASA2C28 construct was found to confer resistance to 5-MT or 6-MA in maize cells (Example 6), the usefulness of this construct as a selectable marker was evaluated in a series of transformation experiments. These experiments were conducted in a manner similar to those described in Example 5 above in that immature maize embryos were bombarded with either plasmid combination 35S/ASA2C28 +pDPG165 or combination 35S/ASA2+pDPG165. However, rather than selecting for transformants on bialaphos-containing media, the selection process was performed on media containing 6-MA, as follows: two days post-bombardment, preselection was initiated with 8–10 embryos per plate on Medium 211VW (Medium 211V from Table 2 supplemented with 6-MA to 33 uM). After 15 days on Medium 211VW, the embryos were transferred to the selection Medium 211VW (Medium 211V minus silver nitrate and supplemented with 6-MA to 100 uM) at one embryo per plate. Transformants bombarded with the 35S/ASA2C28+pDPG165 combination were identified after 12 weeks of selection on the 100 uM 6-MA selection medium. No transformants were obtained from embryos bombarded with the 35S/ASA2+pDPG165 combination. The number of transformants obtained with the 35S/ASA2C28+pDPG165 combination by way of 6-MA selection is similar to that obtained by way of bialaphos selection. This clearly demonstrates that use of the 35S/ASA2C28 construct and 6-MA selection allows for identification of transformants in a manner similar to that in which pDPG165 and bialaphos selection is used for identification of transformants.

All publications and patents are incorporated by reference herein, as though individually incorporated by reference. The invention is not limited to the exact details shown and described, for it should be understood that many variations and modifications may be made while remaining within the spirit and scope of the invention defined by the claims.

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 2073 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GAATTCCGCC AAATCGGGCT ATAGATCAAA CGCTGCACTG TAGGGAGCGT GAAGCCAGCG      60

GCGAATGGAA TCCCTAGCCG CCACCTCCGT GTTCGCGCCC TCCCGCGTCG CCGTCCCGGC     120

GGCGCGGGCC CTGGTTAGGG CGGGGACGGT GGTACCAACC AGGCGGACGA GCAGCCGGAG     180

CGGAACCAGC GGGGTGAAAT GCTCTGCTGC CGTGACGCCG CAGGCGAGCC CAGTGATTAG     240

CAGGAGCGCT GCGGCGGCGA AGGCGGCGGA GGAGGACAAG AGGCGGTTCT TCGAGGCGGC     300

GGCGCGGGGG AGCGGGAAGG GGAACCTGGT GCCCATGTGG GAGTGCATCA AGGGGAACCT     360

GGTGCCCATG TGGGAGTGCA TCGTGTCGGA CCATCTCACC CCCGTGCTCG CCTACCGCTG     420

CCTCGTCCCC GAGGACAACG TCGACGCCCC CAGCTTCCTC TTCGAGTCCG TCGAGCAGGG     480

GCCCCAGGGC ACCACCAACG TCGGCCGCTA TAGCATGGTG GGAGCCCACC CAGTGATGGA     540

GATTGTGGCC AAAGACCACA AGGTTACGAT CATGGACCAC GAGAAGAGCC AAGTGACAGA     600

GCAGGTAGTG GACGACCCGA TGCAGATCCC GAGGACCATG ATGGAGGGAT GGCACCCACA     660

GCAGATCGAC GAGCTCCCTG AATCCTTCTC CGGTGGATGG GTTGGGTTCT TTTCCTATGA     720

TACGGTTAGG TATGTTGAGA AGAAGAAGCT ACCGTTCTCC AGTGCTCCTC AGGACGATAG     780

GAACCTTCCT GATGTGCACT TGGGACTCTA TGATGATGTT CTAGTCTTCG ATAATGTTGA     840

GAAGAAAGTA TATGTTATCC ATTGGGTCAA TGTGGACCGG CATGCATCTG TTGAGGAAGC     900

ATACCAAGAT GGCAGGTCCC GACTAAACAT GTTGCTATCT AAAGTGCACA ATTCCAATGT     960

CCCCACACTC TCTCCTGGAT TTGTGAAGCT GCACACACGC AAGTTTGGTA CACCTTTGAA    1020

CAAGTCGACC ATGACAAGTG ATGAGTATAA GAATGCTGTT CTGCAGGCTA AGGAACATAT    1080

TATGGCTGGG GATATCTTCC AGATTGTTTT AAGCCAGAGG TTCGAGAGAC GAACATATGC    1140

CAACCCATTT GAGGTTTATC GAGCATTACG GATTGTGAAT CCTAGCCCAT ACATGGCGTA    1200

TGTACAGGCA AGAGGCTGTG TATTGGTTGC GTCTAGTCCT GAAATTCTTA CACGAGTCAG    1260

TAAGGGGAAG ATTATTAATC GACCACTTGC TGGAACTGTT CGAAGGGGCA AGACAGAGAA    1320

GGAAGATCAA ATGCAAGAGC AGCAACTGTT AAGTGATGAA AAACAGTGTG CCGAGCACAT    1380

AATGCTTGTG GACTTGGGAA GGAATGATGT TGGCAAGGTA TCCAAACCAG GAGGATCAGT    1440

GAAGGTGGAG AAGTTGATTA TTGAGAGATA CTCCCATGTT ATGCACATAA GCTCAACGGT    1500

TAGTGGACAG TTGGATGATC ATCTCCAGAG TTGGGATGCC TTGAGAGCTG CCTTGCCCGT    1560

TGGAACAGTC AGTGGTGCAC CAAAGGTGAA GGCCATGGAG TTGATTGATA AGTTGGAAGT    1620

TACGAGGCGA GGACCATATA GTGGTGGTCT AGGAGGAATA TCGTTTGATG GTGACATGCA    1680

AATTGCACTT TCTCTCCGCA CCATCGTATT CTCAACAGCG CCGAGCCACA ACACGATGTA    1740

CTCATACAAA GACGCAGATA GGCGTCGGGA GTGGGTCGCT CATCTTCAGG CTGGTGCAGG    1800

CATTGTTGCC GACAGTAGCC CAGATGACGA ACAACGTGAA TGCGAGAATA AGGCTGCTGC    1860

ACTAGCTCGG GCCATCGATC TTGCAGAGTC AGCTTTTGTG AACAAAGAAT AGTGTGCTAT    1920

GGTTATCGTT TAGTTCTTGT TCATGTTTCT TTTACCCACT TTCCGTTAAA AAAGATGTC     1980

ATTAGTGGGT GGAGAAAAGC AATAAGACTG TTCTCTAGAG AACCGAAGAA ATATGGAAAT    2040

TGAGGTTATG GCCGGAATTC CTGCAGCCCG GGG                                 2073
```

(2) INFORMATION FOR SEQ ID NO:2:

(i) SEQUENCE CHARACTERISTICS:
        (A) LENGTH: 615 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Ser Leu Ala Ala Thr Ser Val Phe Ala Pro Ser Arg Val Ala
 1               5                  10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala Lys Ala Ala Glu Glu Asp Lys Arg Arg Phe Phe Glu Ala Ala Ala
65                  70                  75                  80

Arg Gly Ser Gly Lys Gly Asn Leu Val Pro Met Trp Glu Cys Ile Lys
                85                  90                  95

Gly Asn Leu Val Pro Met Trp Glu Cys Ile Val Ser Asp His Leu Thr
            100                 105                 110

Pro Val Leu Ala Tyr Arg Cys Leu Val Pro Glu Asp Asn Val Asp Ala
        115                 120                 125

Pro Ser Phe Leu Phe Glu Ser Val Glu Gln Gly Pro Gln Gly Thr Thr
    130                 135                 140

Asn Val Gly Arg Tyr Ser Met Val Gly Ala His Pro Val Met Glu Ile
145                 150                 155                 160

Val Ala Lys Asp His Lys Val Thr Ile Met Asp His Glu Lys Ser Gln
                165                 170                 175

Val Thr Glu Gln Val Val Asp Asp Pro Met Gln Ile Pro Arg Thr Met
            180                 185                 190

Met Glu Gly Trp His Pro Gln Gln Ile Asp Glu Leu Pro Glu Ser Phe
        195                 200                 205

Ser Gly Gly Trp Val Gly Phe Phe Ser Tyr Asp Thr Val Arg Tyr Val
    210                 215                 220

Glu Lys Lys Lys Leu Pro Phe Ser Ser Ala Pro Gln Asp Asp Arg Asn
225                 230                 235                 240

Leu Pro Asp Val His Leu Gly Leu Tyr Asp Asp Val Leu Val Phe Asp
                245                 250                 255

Asn Val Glu Lys Lys Val Tyr Val Ile His Trp Val Asn Val Asp Arg
            260                 265                 270

His Ala Ser Val Glu Glu Ala Tyr Gln Asp Gly Arg Ser Arg Leu Asn
        275                 280                 285

Met Leu Leu Ser Lys Val His Asn Ser Asn Val Pro Thr Leu Ser Pro
    290                 295                 300

Gly Phe Val Lys Leu His Thr Arg Lys Phe Gly Thr Pro Leu Asn Lys
305                 310                 315                 320

Ser Thr Met Thr Ser Asp Glu Tyr Lys Asn Ala Val Leu Gln Ala Lys
                325                 330                 335

Glu His Ile Met Ala Gly Asp Ile Phe Gln Ile Val Leu Ser Gln Arg
            340                 345                 350

Phe Glu Arg Arg Thr Tyr Ala Asn Pro Phe Glu Val Tyr Arg Ala Leu
        355                 360                 365

Arg Ile Val Asn Pro Ser Pro Tyr Met Ala Tyr Val Gln Ala Arg Gly
    370                 375                 380

Cys Val Leu Val Ala Ser Ser Pro Glu Ile Leu Thr Arg Val Ser Lys
385                 390                 395                 400
```

```
Gly Lys Ile Ile Asn Arg Pro Leu Ala Gly Thr Val Arg Gly Lys
            405                 410                 415

Thr Glu Lys Glu Asp Gln Met Gln Glu Gln Gln Leu Leu Ser Asp Glu
            420                 425                 430

Lys Gln Cys Ala Glu His Ile Met Leu Val Asp Leu Gly Arg Asn Asp
            435                 440                 445

Val Gly Lys Val Ser Lys Pro Gly Gly Ser Val Lys Val Glu Lys Leu
    450                 455                 460

Ile Ile Glu Arg Tyr Ser His Val Met His Ile Ser Ser Thr Val Ser
465                 470                 475                 480

Gly Gln Leu Asp Asp His Leu Gln Ser Trp Asp Ala Leu Arg Ala Ala
                485                 490                 495

Leu Pro Val Gly Thr Val Ser Gly Ala Pro Lys Val Lys Ala Met Glu
            500                 505                 510

Leu Ile Asp Lys Leu Glu Val Thr Arg Arg Gly Pro Tyr Ser Gly Gly
            515                 520                 525

Leu Gly Gly Ile Ser Phe Asp Gly Asp Met Gln Ile Ala Leu Ser Leu
    530                 535                 540

Arg Thr Ile Val Phe Ser Thr Ala Pro Ser His Asn Thr Met Tyr Ser
545                 550                 555                 560

Tyr Lys Asp Ala Asp Arg Arg Glu Trp Val Ala His Leu Gln Ala
                565                 570                 575

Gly Ala Gly Ile Val Ala Asp Ser Ser Pro Asp Asp Glu Gln Arg Glu
            580                 585                 590

Cys Glu Asn Lys Ala Ala Ala Leu Ala Arg Ala Ile Asp Leu Ala Glu
            595                 600                 605

Ser Ala Phe Val Asn Lys Glu
    610                 615

(2) INFORMATION FOR SEQ ID NO:3:

(i) SEQUENCE CHARACTERISTICS:
          (A) LENGTH: 595 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:3:

Met Ser Ser Met Asn Val Ala Thr Met Gln Ala Leu Thr Phe Ser
1               5                   10                  15

Arg Arg Leu Leu Pro Ser Val Ala Ser Arg Tyr Leu Ser Ser Ser
            20                  25                  30

Val Thr Val Thr Gly Tyr Ser Gly Arg Ser Ser Ala Tyr Ala Pro Ser
    35                  40                  45

Phe Arg Ser Ile Lys Cys Val Ser Val Ser Pro Glu Ala Ser Ile Val
    50                  55                  60

Ser Asp Thr Lys Lys Leu Ala Asp Ala Ser Lys Ser Thr Asn Leu Ile
65                  70                  75                  80

Pro Ile Tyr Arg Cys Ile Phe Ser Asp Gln Leu Thr Pro Val Leu Ala
                85                  90                  95

Tyr Arg Cys Leu Val Lys Glu Asp Asp Arg Glu Ala Pro Ser Phe Leu
            100                 105                 110

Phe Glu Ser Val Glu Pro Gly Ser Gln Met Ser Ser Val Gly Arg Tyr
            115                 120                 125
```

```
Ser Val Val Gly Ala Gln Pro Ala Met Glu Ile Val Ala Lys Glu Asn
130                 135                 140

Lys Val Ile Val Met Asp His Asn Asn Glu Thr Met Thr Glu Glu Phe
145                 150                 155                 160

Val Glu Asp Pro Met Glu Ile Pro Arg Lys Ile Ser Glu Lys Trp Asn
                165                 170                 175

Pro Asp Pro Gln Leu Val Gln Asp Leu Pro Asp Ala Phe Cys Gly Gly
            180                 185                 190

Trp Val Gly Phe Phe Ser Tyr Asp Thr Val Arg Tyr Val Glu Lys Arg
        195                 200                 205

Lys Leu Pro Phe Ser Lys Ala Pro Glu Asp Asp Arg Asn Leu Pro Asp
210                 215                 220

Met His Leu Gly Leu Tyr Asp Asp Val Val Phe Asp His Val Glu
225                 230                 235                 240

Lys Lys Ala Tyr Val Ile His Trp Ile Arg Leu Asp Gly Ser Leu Pro
                245                 250                 255

Tyr Glu Lys Ala Tyr Ser Asn Gly Met Gln His Leu Glu Asn Leu Val
            260                 265                 270

Ala Lys Leu His Asp Ile Glu Pro Pro Lys Leu Ala Ala Gly Asn Val
        275                 280                 285

Asn Leu Gln Thr Arg Gln Phe Gly Pro Ser Leu Asp Asn Ser Asn Val
    290                 295                 300

Thr Cys Glu Glu Tyr Lys Glu Ala Val Val Lys Ala Lys Glu His Ile
305                 310                 315                 320

Leu Ala Gly Asp Ile Phe Gln Ile Val Leu Ser Gln Arg Phe Glu Arg
                325                 330                 335

Arg Thr Phe Ala Asp Pro Phe Glu Val Tyr Arg Ala Leu Arg Val Val
            340                 345                 350

Asn Pro Ser Pro Tyr Met Gly Tyr Leu Gln Ala Arg Gly Cys Ile Leu
        355                 360                 365

Val Ala Ser Ser Pro Glu Ile Leu Thr Lys Val Lys Gln Asn Lys Ile
370                 375                 380

Val Asn Arg Pro Leu Ala Gly Thr Ser Lys Arg Gly Lys Asn Glu Val
385                 390                 395                 400

Glu Asp Lys Arg Leu Glu Lys Glu Leu Leu Glu Asn Glu Lys Gln Cys
                405                 410                 415

Ala Glu His Ile Met Leu Val Asp Leu Gly Arg Asn Asp Val Gly Lys
            420                 425                 430

Val Thr Lys Tyr Gly Ser Val Lys Val Glu Lys Leu Met Asn Ile Glu
        435                 440                 445

Arg Tyr Ser His Val Met His Ile Ser Ser Thr Val Thr Gly Glu Leu
450                 455                 460

Gln Asp Gly Leu Thr Cys Trp Asp Val Leu Arg Ala Ala Leu Pro Val
465                 470                 475                 480

Gly Thr Val Ser Gly Ala Pro Lys Val Lys Ala Met Glu Leu Ile Asp
                485                 490                 495

Glu Leu Glu Pro Thr Arg Arg Gly Pro Tyr Ser Gly Gly Phe Gly Gly
            500                 505                 510

Val Ser Phe Thr Gly Asp Met Asp Ile Ala Leu Ser Leu Arg Thr Ile
        515                 520                 525

Val Phe Pro Thr Ala Cys Gln Tyr Asn Thr Met Tyr Ser Tyr Lys Asp
530                 535                 540
```

-continued

```
Ala Asn Lys Arg Arg Glu Trp Val Ala Tyr Leu Gln Ala Gly Ala Gly
545                 550                 555                 560

Val Val Ala Asp Ser Asp Pro Gln Asp Glu His Cys Glu Cys Gln Asn
                565                 570                 575

Lys Ala Ala Gly Leu Ala Arg Ala Ile Asp Leu Ala Glu Ser Ala Phe
                580                 585                 590

Val Lys Lys
        595
```

(2) INFORMATION FOR SEQ ID NO:4:

(i) SEQUENCE CHARACTERISTICS:
        (A) LENGTH: 621 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ser Ala Val Ser Ile Ser Ala Val Lys Ser Asp Phe Phe Thr Val
1                   5                   10                  15

Glu Ala Ile Ala Val Thr His His Arg Thr Pro His Pro Pro His Phe
                20                  25                  30

Pro Ser Leu Arg Phe Pro Leu Ser Leu Lys Ser Pro Pro Ala Thr Ser
            35                  40                  45

Leu Asn Leu Val Ala Gly Ser Lys Leu Leu His Phe Ser Arg Arg Leu
50                  55                  60

Pro Ser Ile Lys Cys Ser Tyr Thr Pro Ser Leu Asp Leu Ser Glu Glu
65                  70                  75                  80

Gln Phe Thr Lys Phe Lys Ala Ser Glu Lys Gly Asn Leu Val Pro
                85                  90                  95

Leu Phe Arg Cys Val Phe Ser Asp His Leu Thr Pro Ile Leu Ala Tyr
            100                 105                 110

Arg Cys Leu Val Lys Glu Asp Asp Arg Asp Ala Pro Ser Phe Leu Phe
            115                 120                 125

Glu Ser Val Glu Pro Gly Ser Gln Ser Ser Asn Ile Gly Arg Tyr Ser
130                 135                 140

Val Val Gly Ala Gln Pro Thr Ile Glu Ile Val Ala Lys Gly Asn Val
145                 150                 155                 160

Val Thr Val Met Asp His Gly Ala Ser Leu Arg Thr Glu Glu Val
                165                 170                 175

Asp Asp Pro Met Met Val Pro Gln Lys Ile Met Glu Glu Trp Asn Pro
            180                 185                 190

Gln Gly Ile Asp Glu Leu Pro Glu Ala Phe Cys Gly Gly Trp Val Gly
            195                 200                 205

Tyr Phe Ser Tyr Asp Thr Val Arg Tyr Val Glu Lys Lys Lys Leu Pro
            210                 215                 220

Phe Ser Asn Ala Pro Glu Asp Asp Arg Ser Leu Pro Asp Val Asn Leu
225                 230                 235                 240

Gly Leu Tyr Asp Asp Val Ile Val Phe Asp His Val Glu Lys Lys Ala
            245                 250                 255

Tyr Val Ile His Trp Val Arg Ile Asp Lys Asp Arg Ser Val Glu Glu
            260                 265                 270

Asn Phe Arg Glu Gly Met Asn Arg Leu Glu Ser Leu Thr Ser Arg Ile
            275                 280                 285
```

```
Gln Asp Gln Lys Pro Pro Lys Met Pro Thr Gly Phe Ile Lys Leu Arg
    290                 295                 300

Thr Gln Leu Phe Gly Pro Lys Leu Glu Lys Ser Thr Met Thr Ser Glu
305                 310                 315                 320

Ala Tyr Lys Glu Ala Val Val Glu Ala Lys Glu His Ile Leu Ala Gly
                325                 330                 335

Asp Ile Phe Gln Ile Val Leu Ser Gln Arg Phe Glu Arg Arg Thr Phe
            340                 345                 350

Ala Asp Pro Phe Glu Ile Tyr Arg Ala Leu Arg Ile Val Asn Pro Ser
        355                 360                 365

Pro Tyr Met Ala Tyr Leu Gln Val Arg Gly Cys Ile Leu Val Ala Ser
    370                 375                 380

Ser Pro Glu Ile Leu Leu Arg Ser Lys Asn Arg Lys Ile Thr Asn Arg
385                 390                 395                 400

Pro Leu Ala Gly Thr Val Arg Arg Gly Lys Thr Pro Lys Glu Asp Leu
                405                 410                 415

Met Leu Glu Lys Glu Leu Leu Ser Asp Lys Gln Cys Ala Glu His
            420                 425                 430

Ile Met Leu Val Asp Leu Gly Arg Asn Asp Val Gly Lys Val Ser Lys
            435                 440                 445

Pro Gly Ser Val Glu Val Lys Lys Leu Lys Asp Ile Glu Trp Phe Ser
    450                 455                 460

His Val Met His Ile Ser Ser Thr Val Val Gly Glu Leu Leu Asp His
465                 470                 475                 480

Leu Thr Ser Trp Asp Ala Leu Arg Ala Val Leu Pro Val Gly Thr Val
                485                 490                 495

Ser Gly Ala Pro Lys Val Lys Ala Met Glu Leu Ile Asp Glu Leu Glu
                500                 505                 510

Val Thr Arg Arg Gly Pro Tyr Ser Gly Gly Phe Gly Gly Ile Ser Phe
            515                 520                 525

Asn Gly Asp Met Asp Ile Ala Leu Ala Leu Arg Thr Met Val Phe Pro
530                 535                 540

Thr Asn Thr Arg Tyr Asp Thr Leu Tyr Ser Tyr Lys His Pro Gln Arg
545                 550                 555                 560

Arg Arg Glu Trp Ile Ala His Ile Gln Ala Gly Ala Gly Ile Val Ala
                565                 570                 575

Asp Ser Asn Pro Asp Asp Glu His Arg Glu Cys Glu Asn Lys Ala Ala
            580                 585                 590

Ala Leu Ala Arg Ala Ile Asp Leu Ala Glu Ser Ser Phe Leu Glu Ala
            595                 600                 605

Pro Glu Phe Thr Thr Ile Thr Pro His Ile Asn Asn Ile
    610                 615                 620

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

AAGAAGATCT AATGCTGGAA AAA                                              23
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GATATTGTTG ATGTGAGGTG TGA                                           23
```

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TGCATTGGAG AGGCATTTGG ATGAAAGATT ATCCGTGCTC                          40
```

(2) INFORMATION FOR SEQ ID NO:8:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TTGCCAAACC CTTTTACTGC TGCGAGGTAC CACAGCTTGG TCATTGAGCA AGAAACCTTC    60
CCACATGATG CTTTGGAGGC TACTGCATGG ACTGAAGATG GACTTATCAT GGCTGCTCGC   120
CACAAGAATA CAAACACATC CAGGGTGTCC AATTCCACCC GGAGAGCA               168
```

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GTACCACCGT CCCCGCCCTA ACCAG                                          25
```

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GAACAGTTCC AGCAAGTG                                                  18
```

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
GTGACAGAGC AGGTAGTG                                                    18
```

(2) INFORMATION FOR SEQ ID NO:12:

(i) SEQUENCE CHARACTERISTICS:
        (A) LENGTH: 2073 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GAATTCCGCC AAATCGGGCT ATAGATCAAA CGCTGCACTG TAGGGAGCGT GAAGCCAGCG    60

GCGAATGGAA TCCCTAGCCG CCACCTCCGT GTTCGCGCCC TCCCGCGTCG CCGTCCCGGC   120

GGCGCGGGCC CTGGTTAGGG CGGGGACGGT GGTACCAACC AGGCGGACGA GCAGCCGGAG   180

CGGAACCAGC GGGGTGAAAT GCTCTGCTGC CGTGACGCCG CAGGCGAGCC CAGTGATTAG   240

CAGGAGCGCT GCGGCGGCGA AGGCGGCGGA GGAGGACAAG AGGCGGTTCT TCGAGGCGGC   300

GGCGCGGGGG AGCGGGAAGG GGAACCTGGT GCCCATGTGG GAGTGCATCA AGGGGAACCT   360

GGTGCCCATG TGGGAGTGCA TCGTGTCGGA CCATCTCACC CCCGTGCTCG CCTACCGCTG   420

CCTCGTCCCC GAGGACAACG TCGACGCCCC CAGCTTCCTC TTCGAGTCCG TCGAGCAGGG   480

GCCCCAGGGC ACCACCAACG TCGGCCGCTA TAGCATGGTG GGAGCCCACC CAGTGATGGA   540

GATTGTGGCC AAAGACCACA AGGTTACGAT CATGGACCAC GAGAAGAGCC AAGTGACAGA   600

GCAGGTAGTG GACGACCCGA TGCAGATCCC GAGGACCATG ATGGAGGGAT GGCACCCACA   660

GCAGATCGAC GAGCTCCCTG AATCCTTCTC CGGTGGATGG GTTGGGTTCT TTTCCTATGA   720

TACGGTTAGG TATGTTGAGA GAAGAAGCT ACCGTTCTCC AGTGCTCCTC AGGACGATAG   780

GAACCTTCCT GATGTGCACT TGGGACTCTA TGATGATGTT CTAGTCTTCG ATAATGTTGA   840

GAAGAAAGTA TATGTTATCC ATTGGGTCAA TGTGGACCGG CATGCATCTG TTGAGGAAGC   900

ATACCAAGAT GGCAGGTCCC GACTAAACAT GTTGCTATCT AAAGTGCACA ATTCCAATGT   960

CCCCACACTC TCTCCTGGAT TTGTGAAGCT GCACACACGC AAGTTTGGTA CACCTTTGAA  1020

CAAGTCGACC ATGACAAGTG ATGAGTATAA GAATGCTGTT CTGCAGGCTA AGGAACATAT  1080

TATGGCTGGG GATATCTTCC AGATTGTTTT AAGCCAGAGG TTCGAGAGAC GAACATATGC  1140

CAACCCATTT GAGGTTTATC GAGCATTACG GATTGTGAAT CCTAGCCCAT ACAAGGCGTA  1200

TGTACAGGCA AGAGGCTGTG TATTGGTTGC GTCTAGTCCT GAAATTCTTA CACGAGTCAG  1260

TAAGGGGAAG ATTATTAATC GACCACTTGC TGGAACTGTT CGAAGGGGCA AGACAGAGAA  1320

GGAAGATCAA ATGCAAGAGC AGCAACTGTT AAGTGATGAA AAACAGTGTG CCGAGCACAT  1380

AATGCTTGTG GACTTGGGAA GGAATGATGT TGGCAAGGTA TCCAAACCAG GAGGATCAGT  1440

GAAGGTGGAG AAGTTGATTA TTGAGAGATA CTCCCATGTT ATGCACATAA GCTCAACGGT  1500

TAGTGGACAG TTGGATGATC ATCTCCAGAG TTGGGATGCC TTGAGAGCTG CCTTGCCCGT  1560
```

```
TGGAACAGTC AGTGGTGCAC CAAAGGTGAA GGCCATGGAG TTGATTGATA AGTTGGAAGT    1620

TACGAGGCGA GGACCATATA GTGGTGGTCT AGGAGGAATA TCGTTTGATG GTGACATGCA    1680

AATTGCACTT TCTCTCCGCA CCATCGTATT CTCAACAGCG CCGAGCCACA ACACGATGTA    1740

CTCATACAAA GACGCAGATA GGCGTCGGGA GTGGGTCGCT CATCTTCAGG CTGGTGCAGG    1800

CATTGTTGCC GACAGTAGCC CAGATGACGA ACAACGTGAA TGCGAGAATA AGGCTGCTGC    1860

ACTAGCTCGG GCCATCGATC TTGCAGAGTC AGCTTTTGTG AACAAAGAAT AGTGTGCTAT    1920

GGTTATCGTT TAGTTCTTGT TCATGTTTCT TTTACCCACT TTCCGTTAAA AAAAGATGTC    1980

ATTAGTGGGT GGAGAAAAGC AATAAGACTG TTCTCTAGAG AACCGAAGAA ATATGGAAAT    2040

TGAGGTTATG GCCGGAATTC CTGCAGCCCG GGG                                 2073

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TTTTAAGCCA GAGGTTCG                                                     18

(2) INFORMATION FOR SEQ ID NO:14:

(i) SEQUENCE CHARACTERISTICS:
        (A) LENGTH: 1084 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TCTAGATATT TTTTGTTTGG TTGTTACTAG CTAGTTTTTT TTAATATGT CTAATCTATC       60

TTTAACAGTC CCCACCCACC CCACACGAGG ACACAATTCA CTGTGGCTCC ATGCTGTGGC     120

ACCAACGGCC ACGGTTGGTG GGTGCCTTGG TGTGGGGACC AGACACCGGG ATTTTTCGCT    180

GCAAACAACT TGCAGCTAAT TTGGCCCCTG TCTTACTGTC TAAGATACGA TAAGGTTACC    240

ACGCAAGCGG TCGACAGACT GTACCTCCTG TGTCCAGTGT CCAAAAAATA AGAATTATTT    300

TTTCAAAAAT TTCAATGTTA ATATCTTCAA TGAAGTTTGT TAGGAAATCA TATCCACAAA    360

CAATATAATA ATACACATTA TTTACTATAT ATTTAGTTGA TTTATTTCGA GATGAAAGAG    420

TAATATTATT ATATTTTTTG ACAAGTACTG TCTCGTCAGG CTGGCTCCAG CAAGGTTCGG    480

CAAAGCTTCC TGTACCCTAA ATATAGAGAA TCAAACAATC ATCTATGCTC TCTAGCAGCA    540

TTTTCTGAAC GGTCCTCTAA ATTTAGATGA CGCTGCTGGA TTCTTTATAT ATAGAATTTC    600

TCTAAATGAT CCTCTATCTA TTTGATACCT TTAAATAATC GGTTTAGCAA AACCTAAAAT    660

ATGTATAATA CATTTGAGGG TATTGATAAA TACATAGGTA AAAAAATAAA AAATAAAAAT    720

ATCTTTAATA TAAATATTTA CGTATTAGGA GACGTGATTT AAAGGACGCT GTTGGAGAGA    780

AAGTAGATAT AAAGGATAAA TTTTTTTAGA GAAGATAGTA AAGAAAGTAT ATAAATGATG    840

ATATAAATTA CATTGATTGA GACAGCCTCA CCCATCATCA ATCAGGAAAG CGACGGTGGC    900

TTCTTCCTCC CCCTTCACCG TACCGAGACC CAAACCAAGC CGCCTCGCCA GCACCCAGCA    960

GCCCGCATAA CTCGTCTCCA TTAAAATCGG TTTTCTCCTT GGAAATCTGC TGGCGAGTCC   1020
```

```
CAGGACCCGA ATGCCCCACT CTTATTACCT GCTAATTTTG AATTTCCTAA TCGGGTTGCA    1080

GCTG                                                                 1084
```

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
CCCAAGTCCA CAAGCATT                                                    18
```

(2) INFORMATION FOR SEQ ID NO:16:

(i) SEQUENCE CHARACTERISTICS:
        (A) LENGTH: 615 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Met Glu Ser Leu Ala Ala Thr Ser Val Phe Ala Pro Ser Arg Val Ala
 1               5                  10                  15

Val Pro Ala Ala Arg Ala Leu Val Arg Ala Gly Thr Val Val Pro Thr
             20                  25                  30

Arg Arg Thr Ser Ser Arg Ser Gly Thr Ser Gly Val Lys Cys Ser Ala
         35                  40                  45

Ala Val Thr Pro Gln Ala Ser Pro Val Ile Ser Arg Ser Ala Ala Ala
     50                  55                  60

Ala Lys Ala Ala Glu Glu Asp Lys Arg Arg Phe Phe Glu Ala Ala Ala
65                  70                  75                  80

Arg Gly Ser Gly Lys Gly Asn Leu Val Pro Met Trp Glu Cys Ile Lys
                 85                  90                  95

Gly Asn Leu Val Pro Met Trp Glu Cys Ile Val Ser Asp His Leu Thr
            100                 105                 110

Pro Val Leu Ala Tyr Arg Cys Leu Val Pro Glu Asp Asn Val Asp Ala
        115                 120                 125

Pro Ser Phe Leu Phe Glu Ser Val Glu Gln Gly Pro Gln Gly Thr Thr
    130                 135                 140

Asn Val Gly Arg Tyr Ser Met Val Gly Ala His Pro Val Met Glu Ile
145                 150                 155                 160

Val Ala Lys Asp His Lys Val Thr Ile Met Asp His Glu Lys Ser Gln
                165                 170                 175

Val Thr Glu Gln Val Val Asp Asp Pro Met Gln Ile Pro Arg Thr Met
            180                 185                 190

Met Glu Gly Trp His Pro Gln Gln Ile Asp Glu Leu Pro Glu Ser Phe
        195                 200                 205

Ser Gly Gly Trp Val Gly Phe Phe Ser Tyr Asp Thr Val Arg Tyr Val
    210                 215                 220

Glu Lys Lys Lys Leu Pro Phe Ser Ser Ala Pro Gln Asp Asp Arg Asn
225                 230                 235                 240

Leu Pro Asp Val His Leu Gly Leu Tyr Asp Asp Val Leu Val Phe Asp
```

-continued

```
                        245                 250                 255
Asn Val Glu Lys Lys Val Tyr Val Ile His Trp Val Asn Val Asp Arg
                260                 265                 270

His Ala Ser Val Glu Glu Ala Tyr Gln Asp Gly Arg Ser Arg Leu Asn
                275                 280                 285

Met Leu Leu Ser Lys Val His Asn Ser Asn Val Pro Thr Leu Ser Pro
        290                 295                 300

Gly Phe Val Lys Leu His Thr Arg Lys Phe Gly Thr Pro Leu Asn Lys
305                 310                 315                 320

Ser Thr Met Thr Ser Asp Glu Tyr Lys Asn Ala Val Leu Gln Ala Lys
                325                 330                 335

Glu His Ile Met Ala Gly Asp Ile Phe Gln Ile Val Leu Ser Gln Arg
                340                 345                 350

Phe Glu Arg Arg Thr Tyr Ala Asn Pro Phe Glu Val Tyr Arg Ala Leu
        355                 360                 365

Arg Ile Val Asn Pro Ser Pro Tyr Lys Ala Tyr Val Gln Ala Arg Gly
        370                 375                 380

Cys Val Leu Val Ala Ser Ser Pro Glu Ile Leu Thr Arg Val Ser Lys
385                 390                 395                 400

Gly Lys Ile Ile Asn Arg Pro Leu Ala Gly Thr Val Arg Arg Gly Lys
                405                 410                 415

Thr Glu Lys Glu Asp Gln Met Gln Glu Gln Gln Leu Leu Ser Asp Glu
                420                 425                 430

Lys Gln Cys Ala Glu His Ile Met Leu Val Asp Leu Gly Arg Asn Asp
                435                 440                 445

Val Gly Lys Val Ser Lys Pro Gly Gly Ser Val Lys Val Glu Lys Leu
        450                 455                 460

Ile Ile Glu Arg Tyr Ser His Val Met His Ile Ser Ser Thr Val Ser
465                 470                 475                 480

Gly Gln Leu Asp Asp His Leu Gln Ser Trp Asp Ala Leu Arg Ala Ala
                485                 490                 495

Leu Pro Val Gly Thr Val Ser Gly Ala Pro Lys Val Lys Ala Met Glu
                500                 505                 510

Leu Ile Asp Lys Leu Glu Val Thr Arg Arg Gly Pro Tyr Ser Gly Gly
        515                 520                 525

Leu Gly Gly Ile Ser Phe Asp Gly Asp Met Gln Ile Ala Leu Ser Leu
        530                 535                 540

Arg Thr Ile Val Phe Ser Thr Ala Pro Ser His Asn Thr Met Tyr Ser
545                 550                 555                 560

Tyr Lys Asp Ala Asp Arg Arg Arg Glu Trp Val Ala His Leu Gln Ala
                565                 570                 575

Gly Ala Gly Ile Val Ala Asp Ser Ser Pro Asp Asp Glu Gln Arg Glu
                580                 585                 590

Cys Glu Asn Lys Ala Ala Ala Leu Ala Arg Ala Ile Asp Leu Ala Glu
                595                 600                 605

Ser Ala Phe Val Asn Lys Glu
        610                 615
```

What is claimed is:

1. A method of imparting tolerance to an amino acid analog of tryptophan to a maize plant cell comprising:
(a) introducing an expression cassette comprising a first DNA segment encoding an exogenous anthranilate synthase operably linked to a promoter other than a native anthranilate synthase promoter functional in a maize plant cell into cells of a susceptible plant to yield transformed plant cells, wherein the anthranilate synthase is substantially resistant to inhibition by free L-tryptophan or an amino acid analog of tryptophan; and (b) expressing the anthranilate synthase encoded by the first DNA segment in the plant cells so as to yield an amount of said anthranilate synthase effective to render the transformed plant cells substantially tolerant to an amount of free L-tryptophan or an amino acid analog of tryptophan that inhibits the growth of the untransformed cells of the susceptible plant.

2. The method according to claim 1 wherein the expression of the first DNA segment is inducible.

3. The method according to claim 1 wherein the expression cassette further comprises plasmid DNA.

4. The method according to claim 1 wherein the first DNA segment encoding the anthranilate synthase is introduced into plant cells by a method selected from the group consisting of electroporation, microinjection, protoplast transformation, microprojectile bombardment, Agrobacterium-mediated transformation, and liposomal encapsulation.

5. A method of selecting transformed maize plant cells, comprising:
   (a) introducing into a maize plant cell an expression cassette comprising a first DNA segment encoding an exogenous anthranilate synthase operably linked to a promoter other than a native anthranilate synthase promoter which is substantially resistant to inhibition by free L-tryptophan or an amino acid analog of tryptophan to yield a transformed plant cell; and
   (b) culturing the transformed plant cell in an amount of free L-tryptophan or an amino acid analog of tryptophan that inhibits the growth of a plant cell which does not contain the first DNA segment.

6. The method according to claim 5 wherein the plant anthranilate synthase is a maize anthranilate synthase.

7. The method according to claim 6 wherein the maize anthranilate synthase has SEQ ID NO:16.

8. The method according to claim 1 wherein the first DNA segment consists essentially of SEQ ID NO:12.

9. The method according to claim 1 wherein the plant cells comprise cells of callus, embryos, meristematic tissue, gametic tissue, or cultured cells in suspension.

10. The method according to claim 1 wherein the amino acid analog is 5-methyltryptophan.

11. A method for altering the tryptophan content in a maize plant comprising:
   (a) introducing into the cells of a susceptible maize plant an expression cassette comprising a first DNA segment encoding an exogenous anthranilate synthase operably linked to a promoter other than a native anthranilate synthase promoter functional in a maize plant cell to yield transformed plant cells, wherein the first DNA segment encodes an anthranilate synthase which is substantially resistant to inhibition by free L-tryptophan or an amino acid analog of tryptophan; and
   (b) regenerating a differentiated plant from said transformed plant cells wherein the cells of the differentiated plant express the anthranilate synthase encoded by the first DNA segment in an amount effective to increase the tryptophan content in the cells of the differentiated plant relative to the tryptophan content in the cells of the untransformed susceptible plant.

12. The method according to claim 1 wherein the amino acid analog is 6-methylanthranilate.

13. A transformed plant regenerated from the transformed plant cells obtained by the method of claim 1.

14. A transformed seed of the transformed plant of claim 13.

15. The method according to claim 11 wherein the tryptophan content of the transformed plant cells is about 1.1- to 50-fold higher than that of the tryptophan content of the susceptible plant cells of step (a).

16. The method according to claim 1, 11 or 5 wherein the anthranilate synthase is a plant anthranilate synthase.

17. The method according to claim 1, 11 or 5 wherein the expression cassette further comprises a second DNA segment encoding an amino terminal chloroplast transit peptide, which is operably linked to the first DNA segment.

18. The method of claim 1, 11 or 5 wherein the promoter comprises a CaMV 35S, CaMV 19S, nos, Adh, sucrose synthase, α-tubulin, actin, cab, PEPCase, or R gene complex promoter.

* * * * *

UNITED STATES PATENT AND TRADEMARK OFFICE
CERTIFICATE OF CORRECTION

PATENT NO.    : 6,118,047
DATED         : September 12, 2000
INVENTOR(S)   : Paul C. Anderson et al.

It is certified that error appears in the above-identified patent and that said Letters Patent is hereby corrected as shown below:

Title page,
Item [73], Assignee, delete "Genetic" and insert -- Genetics -- therefor.

Column 10,
Line 7, delete "(RUBISCO)" and insert -- (RuBISCO) -- therefor.

Column 30,
Line 27, delete "(VII)" and insert -- (V/I) -- therefor.

Column 32,
Line 38, delete "377" and insert -- 366 -- therefor.

Column 65,
Line 32, delete "5" and insert -- 16 -- therefor.

UNITED STATES PATENT AND TRADEMARK OFFICE
CERTIFICATE OF CORRECTION

PATENT NO. : 6,118,047
DATED : September 12, 2000
INVENTOR(S) : Paul C. Anderson et al.

It is certified that error appears in the above-identified patent and that said Letters Patent is hereby corrected as shown below:

<u>Columns 41-44,</u>
In the SEQUENCE LISTING, delete the information in section (2) INFORMATION FOR SEQ ID NO: 1 in (2)(i), (2)(ii), and (2)(xi) and insert --

```
(2) INFORMATION FOR SEQ ID NO:1:

(i) SEQUENCE CHARACTERISTICS:
       (A) LENGTH: 2040 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

GAATTCCGCC AAATCGGGCT ATAGATCAAA CGCTGCACTG TAGGGAGCGT GAAGCCAGCG   60
GCGAATGGAA TCCCTAGCCG CCACCTCCGT GTTCGCGCCC TCCCGCGTCG CCGTCCCGGC  120
GGCGCGGGCC CTGGTTAGGG CGGGGACGGT GGTACCAACC AGGCGGACGA GCAGCCGGAG  180
CGGAACCAGC GGGGTGAAAT GCTCTGCTGC CGTGACGCCG CAGGCGAGCC CAGTGATTAG  240
CAGGAGCGCT GCGGCGGCGA AGGCGGCGGA GGAGGACAAG AGGCGGTTCT TCGAGGCGGC  300
GGCGCGGGGG AGCGGGAAGG GGAACCTGGT GCCCATGTGG GAGTGCATCG TGTCGGACCA  360
TCTCACCCCC GTGCTCGCCT ACCGCTGCCT CGTCCCCGAG GACAACGTCG ACGCCCCAG   420
CTTCCTCTTC GAGTCCGTCG AGCAGGGGCC CCAGGGCACC ACCAACGTCG GCCGCTATAG  480
CATGGTGGGA GCCCACCCAG TGATGGAGAT TGTGGCCAAA GACCACAAGG TTACGATCAT  540

GGACCACGAG AAGAGCCAAG TGACAGAGCA GGTAGTGGAC GACCCGATGC AGATCCCGAG  600
GACCATGATG GAGGGATGGC ACCCACAGCA GATCGACGAG CTCCCTGAAT CCTTCTCCGG  660
TGGATGGGTT GGGTTCTTTT CCTATGATAC GGTTAGGTAT GTTGAGAAGA AGAAGCTACC  720
GTTCTCCAGT GCTCCTCAGG ACGATAGGAA CCTTCCTGAT GTGCACTTGG GACTCTATGA  780
TGATGTTCTA GTCTTCGATA ATGTTGAGAA GAAAGTATAT GTTATCCATT GGGTCAATGT  840
GGACCGGCAT GCATCTGTTG AGGAAGCATA CCAAGATGGC AGGTCCCGAC TAAACATGTT  900
GCTATCTAAA GTGCACAATT CCAATGTCCC CACACTCTCT CCTGGATTTG TGAAGCTGCA  960
CACACGCAAG TTTGGTACAC CTTTGAACAA GTCGACCATG ACAAGTGATG AGTATAAGAA 1020
TGCTGTTCTG CAGGCTAAGG AACATATTAT GGCTGGGGAT ATCTTCCAGA TTGTTTTAAG 1080
CCAGAGGTTC GAGAGACGAA CATATGCCAA CCCATTTGAG GTTTATCGAG CATTACGGAT 1140
TGTGAATCCT AGCCCATACA TGGCGTATGT ACAGGCAAGA GGCTGTGTAT TGGTTGCGTC 1200
TAGTCCTGAA ATTCTTACAC GAGTCAGTAA GGGGAAGATT ATTAATCGAC CACTTGCTGG 1260
AACTGTTCGA AGGGGCAAGA CAGAGAAGGA AGATCAAATG CAAGAGCAGC AACTGTTAAG 1320
TGATGAAAAA CAGTGTGCCG AGCACATAAT GCTTGTGGAC TTGGGAAGGA ATGATGTTGG 1380
CAAGGTATCC AAACCAGGAG GATCAGTGAA GGTGGAGAAG TTGATTATTG AGAGATACTC 1440
CCATGTTATG CACATAAGCT CAACGGTTAG TGGACAGTTG GATGATCATC TCCAGAGTTG 1500
GGATGCCTTG AGAGCTGCCT TGCCCGTTGG AACAGTCAGT GGTGCACCAA AGGTGAAGGC 1560
CATGGAGTTG ATTGATAAGT TGGAAGTTAC GAGGCGAGGA CCATATAGTG GTGGTCTAGG 1620
AGGAATATCG TTTGATGGTG ACATGCAAAT TGCACTTTCT CTCCGCACCA TCGTATTCTC 1680
AACAGCGCCG AGCCACAACA CGATGTACTC ATACAAAGAC GCAGATAGGC GTCGGGAGTG 1740
GGTCGCTCAT CTTCAGGCTG GTGCAGGCAT TGTTGCCGAC AGTAGCCCAG ATGACGAACA 1800
ACGTGAATGC GAGAATAAGG CTGCTGCACT AGCTCGGGCC ATCGATCTTG CAGAGTCAGC 1860
TTTTGTGAAC AAAGAATAGT GTGCTATGGT TATCGTTTAG TTCTTGTTCA TGTTTCTTTT 1920
ACCCACTTTC CGTTAAAAAA AGATGTCATT AGTGGGTGGA GAAAGCAAT  AAGACTGTTC 1980
TCTAGAGAAC CGAAGAAATA TGGAAATTGA GGTTATGGCC GGAATTCCTG CAGCCCGGGG 2040
```

--

UNITED STATES PATENT AND TRADEMARK OFFICE
CERTIFICATE OF CORRECTION

PATENT NO.   : 6,118,047
DATED        : September 12, 2000
INVENTOR(S)  : Paul C. Anderson et al.

It is certified that error appears in the above-identified patent and that said Letters Patent is hereby corrected as shown below:

therefor.

<u>Columns 44-48,</u>
In the SEQUENCE LISTING, delete the information in section (2) INFORMATION FOR SEQ ID NO:2 in (2)(i), (2)(ii), and (2)(xi) and insert --

```
(2) INFORMATION FOR SEQ ID NO:2:

(i) SEQUENCE CHARACTERISTICS:
       (A) LENGTH: 604 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:
```

| | | | | | | | | | | | | | |
|---|---|---|---|---|---|---|---|---|---|---|---|---|---|
| Met | Glu | Ser | Leu | Ala | Ala | Thr | Ser | Val | Phe | Ala | Pro | Ser | Arg | Val | Ala |
| 1 | | | | 5 | | | | | 10 | | | | | 15 |
| Val | Pro | Ala | Ala | Arg | Ala | Leu | Val | Arg | Ala | Gly | Thr | Val | Val | Pro | Thr |
| | | | 20 | | | | | 25 | | | | | 30 |
| Arg | Arg | Thr | Ser | Ser | Arg | Ser | Gly | Thr | Ser | Gly | Val | Lys | Cys | Ser | Ala |
| | | 35 | | | | | 40 | | | | | 45 |
| Ala | Val | Thr | Pro | Gln | Ala | Ser | Pro | Val | Ile | Ser | Arg | Ser | Ala | Ala | Ala |
| | 50 | | | | | 55 | | | | | 60 |
| Ala | Lys | Ala | Ala | Glu | Glu | Asp | Lys | Arg | Arg | Phe | Phe | Glu | Ala | Ala | Ala |
| 65 | | | | | 70 | | | | | 75 | | | | | 80 |
| Arg | Gly | Ser | Gly | Lys | Gly | Asn | Leu | Val | Pro | Met | Trp | Glu | Cys | Ile | Val |
| | | | | 85 | | | | | 90 | | | | | 95 |
| Ser | Asp | His | Leu | Thr | Pro | Val | Leu | Ala | Tyr | Arg | Cys | Leu | Val | Pro | Glu |
| | | | 100 | | | | | 105 | | | | | 110 |
| Asp | Asn | Val | Asp | Ala | Pro | Ser | Phe | Leu | Phe | Glu | Ser | Val | Glu | Gln | Gly |
| | | | 115 | | | | | 120 | | | | | 125 |
| Pro | Gln | Gly | Thr | Thr | Asn | Val | Gly | Arg | Tyr | Ser | Met | Val | Gly | Ala | His |
| | | | 130 | | | | | 135 | | | | | 140 |
| Pro | Val | Met | Glu | Ile | Val | Ala | Lys | Asp | His | Lys | Val | Thr | Ile | Met | Asp |
| 145 | | | | | 150 | | | | | 155 | | | | | 160 |
| His | Glu | Lys | Ser | Gln | Val | Thr | Glu | Gln | Val | Val | Asp | Asp | Pro | Met | Gln |
| | | | | 165 | | | | | 170 | | | | | 175 |

UNITED STATES PATENT AND TRADEMARK OFFICE
CERTIFICATE OF CORRECTION

PATENT NO.    : 6,118,047
DATED         : September 12, 2000
INVENTOR(S)   : Paul C. Anderson et al.

It is certified that error appears in the above-identified patent and that said Letters Patent is hereby corrected as shown below:

```
Ile Pro Arg Thr Met Met Glu Gly Trp His Pro Gln Gln Ile Asp Glu
            180                 185                 190
Leu Pro Glu Ser Phe Ser Gly Gly Trp Val Gly Phe Phe Ser Tyr Asp
            195                 200                 205
Thr Val Arg Tyr Val Glu Lys Lys Lys Leu Pro Phe Ser Ser Ala Pro
            210                 215                 220
Gln Asp Asp Arg Asn Leu Pro Asp Val His Leu Gly Leu Tyr Asp Asp
225                     230                 235                 240
Val Leu Val Phe Asp Asn Val Glu Lys Lys Val Tyr Val Ile His Trp
                245                 250                 255
Val Asn Val Asp Arg His Ala Ser Val Glu Glu Ala Tyr Gln Asp Gly
                260                 265                 270
Arg Ser Arg Leu Asn Met Leu Leu Ser Lys Val His Asn Ser Asn Val
            275                 280                 285
Pro Thr Leu Ser Pro Gly Phe Val Lys Leu His Thr Arg Lys Phe Gly
            290                 295                 300
Thr Pro Leu Asn Lys Ser Thr Met Thr Ser Asp Glu Tyr Lys Asn Ala
305                     310                 315                 320
Val Leu Gln Ala Lys Glu His Ile Met Ala Gly Asp Ile Phe Gln Ile
                325                 330                 335
Val Leu Ser Gln Arg Phe Glu Arg Arg Thr Tyr Ala Asn Pro Phe Glu
                340                 345                 350
Val Tyr Arg Ala Leu Arg Ile Val Asn Pro Ser Pro Tyr Met Ala Tyr
                355                 360                 365
Val Gln Ala Arg Gly Cys Val Leu Val Ala Ser Ser Pro Glu Ile Leu
            370                 375                 380
Thr Arg Val Ser Lys Gly Lys Ile Ile Asn Arg Pro Leu Ala Gly Thr
385                     390                 395                 400
Val Arg Arg Gly Lys Thr Glu Lys Glu Asp Gln Met Gln Glu Gln Gln
                405                 410                 415
Leu Leu Ser Asp Glu Lys Gln Cys Ala Glu His Ile Met Leu Val Asp
            420                 425                 430
```

Page 4 of 9

UNITED STATES PATENT AND TRADEMARK OFFICE
CERTIFICATE OF CORRECTION

PATENT NO.   : 6,118,047                                              Page 5 of 9
DATED        : September 12, 2000
INVENTOR(S)  : Paul C. Anderson et al.

It is certified that error appears in the above-identified patent and that said Letters Patent is hereby corrected as shown below:

```
Leu Gly Arg Asn Asp Val Gly Lys Val Ser Lys Pro Gly Gly Ser Val
        435                 440                 445
Lys Val Glu Lys Leu Ile Ile Glu Arg Tyr Ser His Val Met His Ile
    450                 455                 460
Ser Ser Thr Val Ser Gly Gln Leu Asp Asp His Leu Gln Ser Trp Asp
465                 470                 475                 480
Ala Leu Arg Ala Ala Leu Pro Val Gly Thr Val Ser Gly Ala Pro Lys
                485                 490                 495
Val Lys Ala Met Glu Leu Ile Asp Lys Leu Glu Val Thr Arg Arg Gly
            500                 505                 510
Pro Tyr Ser Gly Gly Leu Gly Gly Ile Ser Phe Asp Gly Asp Met Gln
        515                 520                 525
Ile Ala Leu Ser Leu Arg Thr Ile Val Phe Ser Thr Ala Pro Ser His
    530                 535                 540
Asn Thr Met Tyr Ser Tyr Lys Asp Ala Asp Arg Arg Arg Glu Trp Val
545                 550                 555                 560
Ala His Leu Gln Ala Gly Ala Gly Ile Val Ala Asp Ser Ser Pro Asp
                565                 570                 575
Asp Glu Gln Arg Glu Cys Glu Asn Lys Ala Ala Ala Leu Ala Arg Ala
            580                 585                 590
Ile Asp Leu Ala Glu Ser Ala Phe Val Asn Lys Glu
        595                 600
```

-- therefor.

<u>Columns 57-60,</u>
In the SEQUENCE LISTING, delete the information in section (2) INFORMATION FOR SEQ ID NO:12 in (2)(i), (2)(ii) and (2)(xi) and insert --

UNITED STATES PATENT AND TRADEMARK OFFICE
CERTIFICATE OF CORRECTION

PATENT NO. : 6,118,047
DATED : September 12, 2000
INVENTOR(S) : Paul C. Anderson et al.

It is certified that error appears in the above-identified patent and that said Letters Patent is hereby corrected as shown below:

```
(2) INFORMATION FOR SEQ ID NO:12:

(i) SEQUENCE CHARACTERISTICS:
       (A) LENGTH: 2040 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:12:

GAATTCCGCC AAATCGGGCT ATAGATCAAA CGCTGCACTG TAGGGAGCGT GAAGCCAGCG 60
GCGAATGGAA TCCCTAGCCG CCACCTCCGT GTTCGCGCCC TCCCGCGTCG CCGTCCCGGC 120
GGCGCGGGCC CTGGTTAGGG CGGGGACGGT GGTACCAACC AGGCGGACGA GCAGCCGGAG 180
CGGAACCAGC GGGGTGAAAT GCTCTGCTGC CGTGACGCCG CAGGCGAGCC CAGTGATTAG 240
CAGGAGCGCT GCGGCGGCGA AGGCGGCGGA GGAGGACAAG AGGCGGTTCT TCGAGGCGGC 300
GGCGCGGGGG AGCGGGAAGG GGAACCTGGT GCCCATGTGG GAGTGCATCG TGTCGGACCA 360
TCTCACCCCC GTGCTCGCCT ACCGCTGCCT CGTCCCCGAG GACAACGTCG ACGCCCCCAG 420
CTTCCTCTTC GAGTCCGTCG AGCAGGGGCC CCAGGGCACC ACCAACGTCG GCCGCTATAG 480
CATGGTGGGA GCCCACCCAG TGATGGAGAT TGTGGCCAAA GACCACAAGG TTACGATCAT 540
GGACCACGAG AAGAGCCAAG TGACAGAGCA GGTAGTGGAC GACCCGATGC AGATCCCGAG 600
GACCATGATG GAGGGATGGC ACCCACAGCA GATCGACGAG CTCCCTGAAT CCTTCTCCGG 660
TGGATGGGTT GGGTTCTTTT CCTATGATAC GGTTAGGTAT GTTGAGAAGA AGAAGCTACC 720
GTTCTCCAGT GCTCCTCAGG ACGATAGGAA CCTTCCTGAT GTGCACTTGG GACTCTATGA 780
TGATGTTCTA GTCTTCGATA ATGTTGAGAA GAAAGTATAT GTTATCCATT GGGTCAATGT 840
GGACCGGCAT GCATCTGTTG AGGAAGCATA CCAAGATGGC AGGTCCCGAC TAAACATGTT 900
GCTATCTAAA GTGCACAATT CCAATGTCCC CACACTCTCT CCTGGATTTG TGAAGCTGCA 960
CACACGCAAG TTTGGTACAC CTTTGAACAA GTCGACCATG ACAAGTGATG AGTATAAGAA 1020
TGCTGTTCTG CAGGCTAAGG AACATATTAT GGCTGGGGAT ATCTTCCAGA TTGTTTTAAG 1080
CCAGAGGTTC GAGAGACGAA CATATGCCAA CCCATTTGAG GTTTATCGAG CATTACGGAT 1140
TGTGAATCCT AGCCCATACA AGGCGTATGT ACAGGCAAGA GGCTGTGTAT TGGTTGCGTC 1200
TAGTCCTGAA ATTCTTACAC GAGTCAGTAA GGGGAAGATT ATTAATCGAC CACTTGCTGG 1260
AACTGTTCGA AGGGGCAAGA CAGAGAAGGA AGATCAAATG CAAGAGCAGC AACTGTTAAG 1320

TGATGAAAAA CAGTGTGCCG AGCACATAAT GCTTGTGGAC TTGGGAAGGA ATGATGTTGG 1380
CAAGGTATCC AAACCAGGAG GATCAGTGAA GGTGGAGAAG TTGATTATTG AGAGATACTC 1440
CCATGTTATG CACATAAGCT CAACGGTTAG TGGACAGTTG GATGATCATC TCCAGAGTTG 1500
GGATGCCTTG AGAGCTGCCT TGCCCGTTGG AACAGTCAGT GGTGCACCAA AGGTGAAGGC 1560
CATGGAGTTG ATTGATAAGT TGGAAGTTAC GAGGCGAGGA CCATATAGTG GTGGTCTAGG 1620
AGGAATATCG TTTGATGGTG ACATGCAAAT TGCACTTTCT CTCCGCACCA TCGTATTCTC 1680
AACAGCGCCG AGCCACAACA CGATGTACTC ATACAAAGAC GCAGATAGGC GTCGGGAGTG 1740
GGTCGCTCAT CTTCAGGCTG GTGCAGGCAT TGTTGCCGAC AGTAGCCCAG ATGACGAACA 1800
ACGTGAATGC GAGAATAAGG CTGCTGCACT AGCTCGGGCC ATCGATCTTG CAGAGTCAGC 1860
TTTTGTGAAC AAAGAATAGT GTGCTATGGT TATCGTTTAG TTCTTGTTCA TGTTTCTTTT 1920
ACCCACTTTC CGTTAAAAAA AGATGTCATT AGTGGGTGGA GAAAGCAAT AAGACTGTTC 1980
TCTAGAGAAC CGAAGAAATA TGGAAATTGA GGTTATGGCC GGAATTCCTG CAGCCCGGGG 2040
```

-- therefor.

UNITED STATES PATENT AND TRADEMARK OFFICE
CERTIFICATE OF CORRECTION

PATENT NO.   : 6,118,047
DATED        : September 12, 2000
INVENTOR(S)  : Paul C. Anderson et al.

It is certified that error appears in the above-identified patent and that said Letters Patent is hereby corrected as shown below:

<u>Columns 61-64,</u>
In the SEQUENCE LISTING, delete the information in section (2) INFORMATION FOR SEQ ID NO:16 in (2)(i), (2)(ii) and (2)(xi) and insert --

```
(2) INFORMATION FOR SEQ ID NO:16:

(i) SEQUENCE CHARACTERISTICS:
        (A) LENGTH: 604 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Met Glu Ser Leu Ala Ala Thr Ser Val Phe Ala Pro Ser Arg Val Ala
 1           5                  10                 15
Val Pro Ala Ala Arg Ala Leu Val Arg Ala Gly Thr Val Val Pro Thr
             20                  25                 30
Arg Arg Thr Ser Ser Arg Ser Gly Thr Ser Gly Val Lys Cys Ser Ala
             35                  40                 45
Ala Val Thr Pro Gln Ala Ser Pro Val Ile Ser Arg Ser Ala Ala Ala
         50                  55                 60
Ala Lys Ala Ala Glu Glu Asp Lys Arg Arg Phe Phe Glu Ala Ala Ala
65                   70                 75                 80
Arg Gly Ser Gly Lys Gly Asn Leu Val Pro Met Trp Glu Cys Ile Val
                     85                 90                 95
Ser Asp His Leu Thr Pro Val Leu Ala Tyr Arg Cys Leu Val Pro Glu
                 100                105                110
Asp Asn Val Asp Ala Pro Ser Phe Leu Phe Glu Ser Val Glu Gln Gly
             115                120                125
Pro Gln Gly Thr Thr Asn Val Gly Arg Tyr Ser Met Val Gly Ala His
     130                135                140
Pro Val Met Glu Ile Val Ala Lys Asp His Lys Val Thr Ile Met Asp
145                150                155                160
His Glu Lys Ser Gln Val Thr Glu Gln Val Val Asp Asp Pro Met Gln
                 165                170                175
Ile Pro Arg Thr Met Met Glu Gly Trp His Pro Gln Gln Ile Asp Glu
             180                185                190
Leu Pro Glu Ser Phe Ser Gly Gly Trp Val Gly Phe Phe Ser Tyr Asp
         195                200                205
Thr Val Arg Tyr Val Glu Lys Lys Lys Leu Pro Phe Ser Ser Ala Pro
     210                215                220
Gln Asp Asp Arg Asn Leu Pro Asp Val His Leu Gly Leu Tyr Asp Asp
225                230                235                240
Val Leu Val Phe Asp Asn Val Glu Lys Lys Val Tyr Val Ile His Trp
                 245                250                255
Val Asn Val Asp Arg His Ala Ser Val Glu Glu Ala Tyr Gln Asp Gly
             260                265                270
Arg Ser Arg Leu Asn Met Leu Leu Ser Lys Val His Asn Ser Asn Val
         275                280                285
```

UNITED STATES PATENT AND TRADEMARK OFFICE
CERTIFICATE OF CORRECTION

PATENT NO.    : 6,118,047
DATED         : September 12, 2000
INVENTOR(S)   : Paul C. Anderson et al.

Page 8 of 9

It is certified that error appears in the above-identified patent and that said Letters Patent is hereby corrected as shown below:

```
Pro Thr Leu Ser Pro Gly Phe Val Lys Leu His Thr Arg Lys Phe Gly
    290             295             300
Thr Pro Leu Asn Lys Ser Thr Met Thr Ser Asp Glu Tyr Lys Asn Ala
305             310             315             320
Val Leu Gln Ala Lys Glu His Ile Met Ala Gly Asp Ile Phe Gln Ile
            325             330             335
Val Leu Ser Gln Arg Phe Glu Arg Arg Thr Tyr Ala Asn Pro Phe Glu
            340             345             350
Val Tyr Arg Ala Leu Arg Ile Val Asn Pro Ser Pro Tyr Lys Ala Tyr
            355             360             365
Val Gln Ala Arg Gly Cys Val Leu Val Ala Ser Ser Pro Glu Ile Leu
    370             375             380
Thr Arg Val Ser Lys Gly Lys Ile Ile Asn Arg Pro Leu Ala Gly Thr
385             390             395             400
Val Arg Arg Gly Lys Thr Glu Lys Glu Asp Gln Met Gln Glu Gln Gln
            405             410             415
Leu Leu Ser Asp Glu Lys Gln Cys Ala Glu His Ile Met Leu Val Asp
            420             425             430
Leu Gly Arg Asn Asp Val Gly Lys Val Ser Lys Pro Gly Gly Ser Val
            435             440             445
Lys Val Glu Lys Leu Ile Ile Glu Arg Tyr Ser His Val Met His Ile
    450             455             460
Ser Ser Thr Val Ser Gly Gln Leu Asp Asp His Leu Gln Ser Trp Asp
465             470             475             480
Ala Leu Arg Ala Ala Leu Pro Val Gly Thr Val Ser Gly Ala Pro Lys
            485             490             495
Val Lys Ala Met Glu Leu Ile Asp Lys Leu Glu Val Thr Arg Arg Gly
            500             505             510
Pro Tyr Ser Gly Gly Leu Gly Gly Ile Ser Phe Asp Gly Asp Met Gln
            515             520             525
Ile Ala Leu Ser Leu Arg Thr Ile Val Phe Ser Thr Ala Pro Ser His
            530             535             540
Asn Thr Met Tyr Ser Tyr Lys Asp Ala Asp Arg Arg Arg Glu Trp Val
545             550             555             560
```

UNITED STATES PATENT AND TRADEMARK OFFICE
CERTIFICATE OF CORRECTION

PATENT NO.  : 6,118,047
DATED       : September 12, 2000
INVENTOR(S) : Paul C. Anderson et al.

It is certified that error appears in the above-identified patent and that said Letters Patent is hereby corrected as shown below:

```
Ala His Leu Gln Ala Gly Ala Gly Ile Val Ala Asp Ser Ser Pro Asp
            565             570                     575
Asp Glu Gln Arg Glu Cys Glu Asn Lys Ala Ala Ala Leu Ala Arg Ala
            580             585                     590
Ile Asp Leu Ala Glu Ser Ala Phe Val Asn Lys Glu
        595             600
```

-- therefor.

Signed and Sealed this

Twentieth Day of August, 2002

Attest:

JAMES E. ROGAN
Attesting Officer        Director of the United States Patent and Trademark Office